US008466263B2

(12) United States Patent
Marasco et al.

(10) Patent No.: US 8,466,263 B2
(45) Date of Patent: Jun. 18, 2013

(54) CARBONIC ANHYDRASE IX (G250) ANITBODIES

(75) Inventors: Wayne A. Marasco, Wellesley, MA (US); Agnes Lo, Boston, MA (US); Chen Xu, Beijing (CN)

(73) Assignee: Dana-Farber Cancer Institute, Inc., Boston, MA (US)

( * ) Notice: Subject to any disclaimer, the term of this patent is extended or adjusted under 35 U.S.C. 154(b) by 794 days.

(21) Appl. No.: 12/095,773

(22) PCT Filed: Dec. 4, 2006

(86) PCT No.: PCT/US2006/046350
§ 371 (c)(1),
(2), (4) Date: Nov. 3, 2008

(87) PCT Pub. No.: WO2007/065027
PCT Pub. Date: Jun. 7, 2007

(65) Prior Publication Data
US 2009/0068095 A1    Mar. 12, 2009

Related U.S. Application Data

(60) Provisional application No. 60/742,149, filed on Dec. 2, 2005.

(51) Int. Cl.
*C07K 16/40* (2006.01)
*C07K 16/00* (2006.01)
*A61K 39/395* (2006.01)

(52) U.S. Cl.
USPC ............. 530/388.26; 530/388.15; 530/388.1; 530/387.3; 530/387.1; 424/146.1; 424/141.1; 424/134.1; 435/810

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | 424/19 |
| 4,485,045 A | 11/1984 | Regen | 260/403 |
| 4,522,811 A | 6/1985 | Eppstein et al. | 514/2 |
| 4,544,545 A | 10/1985 | Ryan et al. | 424/1.1 |
| 4,676,980 A | 6/1987 | Segal et al. | 424/85 |
| 4,816,567 A | 3/1989 | Cabilly et al. | 530/387 |
| 4,946,778 A | 8/1990 | Ladner et al. | 435/69.6 |
| 5,013,556 A | 5/1991 | Woodle et al. | 424/450 |
| 5,030,719 A | 7/1991 | Umemoto et al. | 530/391 |
| 5,091,513 A | 2/1992 | Huston et al. | 530/387 |
| 5,132,405 A | 7/1992 | Huston et al. | 530/387.3 |
| 5,233,409 A | 8/1993 | Schwab | 356/402 |
| 5,545,806 A | 8/1996 | Lonberg et al. | 800/2 |
| 5,545,807 A | 8/1996 | Surani et al. | 800/2 |
| 5,569,825 A | 10/1996 | Lonberg et al. | 800/2 |
| 5,625,126 A | 4/1997 | Lonberg et al. | 800/2 |
| 5,633,425 A | 5/1997 | Lonberg et al. | 800/2 |
| 5,661,016 A | 8/1997 | Lonberg et al. | 435/172.3 |
| 5,916,771 A | 6/1999 | Hori et al. | 435/69.6 |
| 5,939,598 A | 8/1999 | Kucherlapati et al. | 800/25 |
| 5,989,838 A * | 11/1999 | Zavada et al. | 435/7.23 |

FOREIGN PATENT DOCUMENTS

| | | |
|---|---|---|
| EP | 0 003 089 | 7/1979 |
| WO | WO 91/00360 | 1/1991 |
| WO | WO 92/20373 | 11/1992 |
| WO | WO 94/02602 | 2/1994 |
| WO | WO 94/11026 | 5/1994 |
| WO | WO 95/22618 | 8/1995 |
| WO | WO 96/33735 | 10/1996 |
| WO | WO 96/34096 | 10/1996 |
| WO | WO 99/53049 | 10/1999 |
| WO | WO 02/062972 A2 | 8/2002 |
| WO | WO 03/048328 A2 | 6/2003 |
| WO | WO 2004/002526 A1 | 1/2004 |

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Wu et al. (Nature Biotechnology, Sep. 2005, 23:1137-1146).*
Lam et al. (Curr Oncol Rep. Mar. 2005;7(2):109-15).*
Balint et al., "Antibody engineering by parsimonious mutagenesis", *Gene*, 137(1):109-118 (1993).
Barbas et al., "Recombinant human Fab fragments neutralize human type 1 immunodeficiency virus in vitro", *Proc. Nat'l. Acad. Sci. U.S.A.*, 89:9339-9343 (1992).
Baselga et al., "Recombinant Humanized Anti-HER2 Antibody (Herceptin™) Enhances the Antitumor Activity of Paclitaxel and Doxorubicin Against HER2/neu Overexpressing Human Breast Cancer Xenografts", *Cancer Res.*, 58:2825-2831 (1998).
Baxevanis et al., "Targeting of tumor cells by lymphocytes engineered to express chimeric receptor genes", *Cancer Immunol. Immunother.*, 53:893-903 (2004).
Bobo et al., "Convection-enhanced delivery of macromolecules in the brain," *Proc. Nat'l. Acad. Sci. U.S.A.*, 91:2076-2080 (1994).
Brentjens et al., "Eradication of systemic B-cell tumors by genetically targeted human T lymohocytes co-stimulated by CD80 and interleukin-15", *Nat. Med.*, 9(3):279-286 (2003).
Brion et al., "Micro-Method for the Measurement of Carbonic Anhydrase Activity in Cellular Homogenates", *Anal. Biochem.*, 175(1):289-297 (1988).

(Continued)

Primary Examiner — Sharon Wen
(74) Attorney, Agent, or Firm — Mintz Levin Cohn Ferris Glovsky and Popeo, P.C.; Ivor R. Elrifi; Cynthia A. Kozakiewicz

(57) ABSTRACT

The invention provides scFv antibodies and monoclonal antibodies that bind to and decrease an activity of Carbonic Anhydrase IX (G250). Also provided are methods of treating and/or preventing cancer, such as renal clear cell cancer. Also provided are methods of identifying a carbonic anhydrase IX (G250) protein. The invention additionally provides methods of modifying immune effector cells, and the immune effector cells modified thereby.

17 Claims, 29 Drawing Sheets

OTHER PUBLICATIONS

Brouwers et al., "PET Radioimmunoscintigraphy of Renal Cell Cancer Using $^{89}$Zr-Labeled cG250 Monoclonal Antibody in Nude Rats", *Cancer Biother. Radiopharmaceuticals*, 19(2):155-163 (2004).

Carell et al., "A Novel Procedure for the Synthesis of Libraries Containing Small Organic Molecules", *Angew. Chem. Int. Ed. Engl.*, 33(20):2059-2061 (1994).

Carell et al., "A Solution-Phase Screening Procedure for the Isolation of Active Compounds from a Library of Molecules", *Angew. Chem. Int. Ed. Engl.*, 33(20):2061-2064 (1994).

Carnahan et al., "Epratuzumab, a Humanized Monoclonal Antibody Targeting CD22: Characterization of in Vitro Properties", *Clin. Cancer. Res.*, 9(Suppl.):3982s-3900s (2003).

Caron et al., "Engineered Humanized Dimeric Forms of IgG Are More Effective Antibodies", *J. Exp. Med.*, 176:1191-1195 (1992).

Cho et al., "An Unnatural Biopolymer", *Science*, 261:1303-1305 (1993).

Cole et al., "The EBV-Hybridoma Technique and its Application to Human Lung Cancer", in *Monoclonal Antibodies and Cancer Therapy*, Alan R. Liss, Inc., pp. 77-96 (1985).

"Conjugate Vaccines", in *Contributions to Microbiology and Immunology*, J. M. Cruse and R.E. Lewis, Jr. (eds), Carger Press, New York, whole book (1989).

Cote et al., "Generation of human monoclonal antibodies reactive with cellular antigens", *Proc. Nat'l. Acad. Sci. U.S.A.*, 80:2026-2030 (1983).

Cull et al., "Screening for receptor ligands using large libraries of peptides linked to the C terminus of the *lac* repressor", *Proc. Nat'l. Acad. Sci. U.S.A.*, 89:1865-1869 (1992).

Cwirla et al., "Peptides on phage: A vast library of peptides for identifying ligands", *Proc. Nat'l. Acad. Sci. U.S.A.*, 87:6378-6382 (1990).

Davidson et al., "A model system for in vivo gene transfer into the central nervous system using an adenoviral vector", *Nat: Genet.*, 3(3):219-223 (1993).

Davies et al., "Affinity improvement of single antibody VH domains: residues in all three hypervariable regions affect antigen binding", *Immunotech.* 2(3):169-179 (1996).

Davies et al., "Antibody-Antigen Complexes", *Ann. Rev. Biochem.*, 59:439-473 (1990).

De Haard et al., "A Large Non-immunized Human Fab Fragment Phage Library That Permits Rapid Isolation and Kinetic Analysis of High Affinity Antibodies", *J. Biol. Chem.*, 274(26):18218-18230 (1999).

Devlin, "Random Peptide Libraries: A Source of Specific Protein Binding Molecules", *Science*, 249:404-406 (1990).

DeWitt et al., "'Diversomers': An approach to nonpeptide, nonoligomeric chemical diversity", *Proc. Nat'l. Acad. Sci. U.S.A.*, 90:6909-6913 (1993).

Dodgson et al., "The Carbonic Anhydrases", Plenum, New-York-London, Chapters 6, 7, 8, 9, 10, 11 and 12, pp. 79-159 (1991).

Doege et al., "Complete Coding Sequence and Deduced Primary Structure of the Human Cartilage Large Aggregating Proteoglycan, Aggrecan", *J. Biol. Chem.*, 266(2):894-902 (1991).

Dürrbach et al., "Antibody-mediated endocytosis of G250 tumor-associated antigen allows targeted gene transfer to human renal cell carcinoma in vitro", *Cancer Gene Ther.*, 6(6):564-571 (1999).

Ebert et al., "Establishment and Characterization of Human Renal Cancer and Normal Kidney Cell Lines", *Cancer Res.*, 50:5531-5536 (1990).

Eppstein et al., "Biological activity of liposome-encapsulated murine interferon Y is mediated by a cell membrane receptor", *Proc. Nat'l. Acad. Sci. U.S.A.*, 82:3688-3692 (1985).

Erb et al., "Recursive deconvolution of combinatorial chemical libraries", *Proc. Nat'l. Acad. Sci. U.S.A.*, 91:11422-11426 (1994).

Felici et al., "Selection of Antibody Ligands from a Large Library of Oligopeptides Expressed on a Multivalent Exposition Vector", *J. Mol. Biol.*, 222(2):301-310 (1991).

Fishwild et al., "High-avidity human IgGx monoclonal antibodies from a novel starin of minilocus transgenic mice", *Nature Biotech.*, 14(7):845-851 (1996).

Fodor et al., "Multiplexed biochemical assays with biological chips", *Nature*, 364(6437:555-556 (1993).

Gallop et al., "Applications of Combinatorial Technologies to Drug Discovery. 1. Background and Peptide Combinatorial Libraries", *J. Med. Chem.*, 37(9):1233-1251 (1994).

Geller et al., "An HSV-1 Vector Expressing Tyrosine Hydroxylase Causes Production and Release of L-DOPA from Cultured Rat Striatal Cells", *J. Neurochem.*, 64:487-496 (1995).

Geller et al., "Infection of cultured central nervous system neurons with a defective herpes simplex virus 1 vector results in stable expression of *Escherichia coli* β-galactosidase", *Proc. Nat'l. Acad. Sci. U.S.A.*, 87:1149-1153 (1990).

Geller et al., "Long-term increases in neurotransmitter release from neuronal cells expressing a constitutively active adenylate cyclase from a herpes simplex virus type 1 vector", *Proc. Nat'l. Acad. Sci. U.S.A.*, 90:7603-7607 (1993).

Grabmaier et al., "Molecular cloning and immunogenicity of renal cell carcinoma-associated antigen G250", *Int. J. Cancer*, 85:865-870 (2000).

Griffiths et al., "Isolation of high affinity human antibodies directly from large synthetic repertoires", *EMBO J.*, 13(14):3245-3260 (1994).

Guilford, P., "E-cadherin downregulation in cancer: fuel or fire?", *Mol. Med. Today*, 5:172-177 (1999).

Hanahan et al., "Patterns and Emerging Mechanisms of the Angiogenic Switch during Tumorigenesis", *Cell*, 86:353-364 (1996).

Holt et al., "Domain antibodies: proteins for therapy", *Trends*, 21(11):484-490 (2003).

Hoogenboom et al., "By-passing Immunisation. Human Antibodies from Synthetic Repertoires of Germline $V_H$ Gene Segments Rearranged in Vitro", *J. Mol. Biol.*, 227:381 (1991).

Houghten et al., "The Use of Synthetic Peptide Combinatorial Libraries for the Identification of Bioactive Peptides", *Biotech.*, 13(2):412-421 (1992).

Hurwitz et al., "Combination Immunotherapy of Primary Prostate Cancer in a Transgenic Mouse Model Using CTLA-4 Blockade", *Cancer Res.*, 60:2444-2448 (2000).

Huse et al., "Generation of a Large Combinatorial Library of the Immunoglobulin Repertoire in Phage Lambda", *Science*, 246:1275-1281 (1989).

Huston et al., "Protein engineering of antibody binding sites: Recovery of specific activity in an anti-digoxin single-chain Fv analogue produced in *Escherichia coli*", *Proc. Nat'l. Acad. Sci. U.S.A.*, 85(16):5879-5883 (1988).

Hwang et al., "Hepatic uptake and degradation of unilamellar sphingomyelin/cholesterol liposomes: A kinetic study", *Proc. Nat'l. Acad. Sci. U.S.A.*, 77(7):4030-4034 (1980).

Ivanov et al., "Down-regulation of transmembrane carbonic anhydrases in renal cell carcinoma cell lines by wild-type Hippel-Landau transgenes", *Proc. Nat'l. Acad. Sci. U.S.A.*, 95:12596-12601 (1998).

Ivanov et al., "Expression of Hypoxia-Inducible Cell-Surface Transmembrane Carbonic Anhydrase in Human Cancer", *Am. J. Pathol.*, 158(3):905-919 (2001).

Jansen et al., "Immunotoxins: Hybrid Molecules Combining High Specificity and Potent Cytotoxicity", *Immunol. Rev.*, 62:185-216 (1982).

Kaplitt et al., "Long-term gene expression and phenotypic correction using adeno-associated virus vectors in the mammalian brain", *Nat. Genet.*, 8:148-154 (1994).

Karlsson et al., "Kinetic analysis of monoclonal antibody-antigen interactions with a new biosensor based analytical system", *J. Immunol. Meth.*, 145(1-2):229-240 (1991).

Kawai et al., "Clinical course and immune response of a renal cell carcinoma patient to adoptive transfer of autologous cytotoxic T lymphocytes", *Clin. Exp. Immunol.*, 134:264:269 (2003).

Kenanova et al., "Tailoring the Pharmacokinetics and Positron Emission Tomography Imaging Properties of Anti-Carcinoembryonic Antigen Single-Chain Fv-Fc Antibody Fragments", *Cancer Res.*, 65(2):622-630 (2005).

Killen et al., "Specific Killing of Lymphocytes That Cause Experimental Autoimmune Myasthenia Gravis by Ricin Toxin-Acetylcholine Receptor Conjugates" *J. Immunol.*, 133(5):2549-2553 (1984).

Kohler et al., "Continuous cultures of fused cells secreting antibody of predefined specificity", *Nature*, 256(5517):495-497 (1975).
Kozbor et al., "A Human Hybrid Myeloma for Production of Human Monoclonal Antibodies", *J. Immunol.*, 133(6):3001-3005 (1984).
Kozbor et al., "The production of monoclonal antibodies from human lymphocytes", *Immunol. Today*, 4(3):72-79 (1983).
Kwon et al., "Elimination of residual metastatic prostate cancer after surgery and adjunctive cytotoxic T lymphocyte-associated antigen 4 (CTLA-4) blockade immunotherapy", *Proc. Nat'l. Acad. Sci. U.S.A.*, 96(26):15074-15079 (1999).
Lam, K.S., "A new type of synthetic peptide library for identifying ligand-binding activity", *Nature*, 354(6348):82-84 (1991).
Lam, K.S., "Application of combinatorial library methods in cancer research and drug discovery", *Anti-Cancer Drug Des.*, 12(3):145-167 (1997).
Lamers et al., "Protocol for gene transduction and expansion of human T lymphocytes for clinical immunogene therapy of cancer", *Cancer Gene Ther.*, 9:613-623 (2002).
LeGal et al., "An Adenovirus Vector for Gene Transfer into Neurons and Glia in the Brain", *Science*, 259:988-990 (1993).
Liao et al., "Identification of the MN Antigen as a Diagnostic Biomarker of Cervical Intraepithelial Squamous and Glandular Neoplasia and Cervical Carcinomas", *Am. J. Pathol.*, 145(3):598-609 (1994).
Liu et al., "Anti-renal cell carcinoma chimeric antibody G250: cytokine enhancement of in vitro antibody-dependent cellular cytotoxicity", *Cancer Immunol. Immunother.*, 51(3):171-177 (2002).
Liu et al., "High Rate of Induction of Human Autologous Cytotoxic T Lymphocytes against Renal Carcinoma Cells Cultured with an Interleukin Cocktail", *Jpn. J. Cancer Res.*, 89:1195-1201b (1998).
Lonberg et al., "Antigen-specific human antibodies from mice comprising four distinct genetic modifications", *Nature*, 368(6474):856-859 (1994).
Lonberg et al., "Human Antibodies from Transgenic Mice", *Intern. Rev. Immunol.*, 13(1):65-93 (1995).
Luiten et al., "Generation of chimeric bispecific G250/anti-CD3 monoclonal antibody, a tool to combat renal cell carcinoma", *Bri. J. Cancer*, 74(5):735-744 (1996).
Maher et al., "Human T-lymphocyte cytotoxicity and proliferation directed by a single chimeric TCRζ/CD28 receptor", *Nature Biotech.*, 20(1):70-75 (2002).
Malmqvist, M., "Biospecific interaction analysis using biosensor technology," *Nature*, 361(6408)186-187 (1993).
Marasco et al., "Design, intracellular expression, and activity of a human anti-human immunodeficiency virus type 1 gp120 single-chain antibody", *Proc. Nat'l. Acad. Sci. U.S.A.*, 90:7889-7893 (1993).
Marks et al., "By-passing Immunization—Human Antibodies from V-gene Libraries displayed on Phage", *J. Mol. Biol.*, 222(3):581-597 (1991).
Marks et al., "By-Passing Immunization: Building High Affinity Human Antibodies by Chain Shuffling", *Bio/Tech.*, 10:779-783 (1992).
Martin et al., "Irreversible Coupling of Immunoglobulin Fragments to Preformed Vesicles", *J. Biol. Chem.*, 257(1):286-288 (1982).
Maxwell et al., "The tumor suppressor protein VHL targets hypoxia-inducible factors for oxygen-dependent proteolysis", *Nature*, 399:271-275 (1999).
Michael et al., "Renal-cell carcinoma: tumour markers, T-cell epitopes, and potential for new therapies", *Lancet Oncol.*, 4(4):215-223 (2003).
Mirzabekov et al., "Paramagnetic proteoliposomes containing a pure, native, and oriented seven-transmembrane segment protein, CCR5", *Nature Biotech.*, 18(6):649-654 (2000).
Morrison et al., "High-flow microinfusion: Tissue penetration and pharmacodynamics", *Am. J. Physiol.*, 266(1):R292-R305 (1994).
Morrison, "Success in specification", *Nature*, 368:812-813 (1994).
Munson et al., "LIGAND: A Versatile Computerized Approach for Characterization of Ligand-Binding Systems", *Anal. Biochem.*, 107(1):220-239 (1980).
Neuberger, M., "Generating high-avidity human Mabs in mice", *Nature Biotech.*, 14(7):826 (1996).

Nissim et al., "Antibody fragments from a 'single pot' phage display library as immunochemical reagents", *EMBO J.*, 13(3):692-698 (1994).
Ogueta et al., "Design and In Vitro Characterization of a Single Regulatory Module for Efficient Control of Gene Expression in Both Plasmid DNA and a Self-Inactivating Lentiviral Vector", *Mol. Med.*, 7(8):569-571 (2001).
Ohh et al., "The von Hipple-Lindau tumour suppressor protein: new perspectives", *Mol. Med. Today*, 5:257-263 (1999).
Oosterwijk et al., "Monoclonal Antibody G 250 Recognizes a Determinant Present in Renal-Cell Carcinoma and Absent From Normal Kidney", *Int. J. Cancer*, 38:489-494 (1986).
Parkkila et al., "Carbonic anhydrase inhibitor suppresses invasion of renal cancer cells in vitro", *Proc. Nat'l. Acad. Sci. U.S.A.*, 97(5):2220-2224 (2000).
Pastorek et al., "Cloning and characterization of MN, a human tumor-associated protein with a domain homologous to carbonic anhydrase and a putative helix-loop-helix DNA binding segment", *Oncogene*, 9(10):2877-2888 (1994).
Pastorekova et al., "A Novel Quasi-viral Agent, MaTu, is a Two-Component System", *Virology*, 187(2):620-626 (1992).
Pinthus et al., "Immuno-Gene Therapy of Established Prostate Tumors Using Chimeric Receptor-redirected Human Lymphocytes", *Cancer Res.*, 63:2470-2476 (2003).
Ramakrishnan et al., "Comparison of the Selective Cytotoxic Effects of Immunotoxins Containing Ricin A Chain or Pokeweed Antiviral Protein and Anti-Thy 1.1 Monoclonal Antibodies" *Cancer Res.*, 44:201-208 (1984).
Riviere et al., "Novel Strategies for Cancer Therapy: The Potential of Genetically Modified T Lymphocytes", *Curr. Hematol. Reports*, 3(4):290-297 (2004).
Salmon et al., "High-level transgene expression in human hematopoietic progenitors and differentiated blood lineages after transduction with improved lentiviral vectors", *Blood*, 96(10):3392-3398 (2000).
Scott et al., "Searching for Peptide Ligands with an Epitope Library", *Science*, 249:386-390 (1990).
Semenza, G.L., "Hypoxia, Clonal Selectin, and the Role of HIF-1 in Tumor Progression", Crit. Rev. Biochem. Mol. Biol., 35(2):71-103 (2000).
Sheets et al., "Efficient construction of a large nonimmune phage antibody library: The production of high-affinity human single-chain antibodies to protein antigens", *Proc. Nat'l. Acad. Sci. U.S.A.*, 95:6157-6162 (1998).
Shopes, B., "A Genetically Engineered Human IgG Mutant With Enhanced Cytolytic Activity", *J. Immunol.*, 148(9):2918-2922 (1992).
Steffens et al., "Phase I Radioimmunotherapy of Metastatic Renal Cell Carcinoma with $^{131}$I-labeled Chimeric Monoclonal Antibody G250", *Clin. Cancer Res.*, 5(Suppl.):3268s-3274s (1999).
Steffens et al., "Targeting of Renal Cell Carcinoma With Iodine-131-Labeled Chimeric Monoclonal Antibody G250", *J. Clin. Oncol.*, 15(4):1529-1537 (1997).
Stevenson et al., "A chimeric antibody with dual Fc regions (*bis*FabFc) prepared by manipulations at the IgG hinge", *Anti-Cancer Drug Design*, 3:219-230 (1989).
Sui et al., "Potent neutralization of severe acute respiratory syndrome (SARS) coronavirus by a human mAb to S1 protein that blocks receptor association", *Proc. Nat'l. Acad. Sci. U.S.A.*, 101(8):2536-2541 (2004).
Svastova et al., "Carbonic anhydrase IX reduces E-cadherin-mediated adhesion of MDCK cells via interaction with β-catenin", *Exp. Cell Res.*, 290(2):332-345 (2003).
Tsui et al., "Production of human clotting factor IX without toxicity in mice after vascular delivery of a lentiviral vector", *Nature Biotech.*, 20(1):53-57 (2002).
Vaughan et al., "Human Antibodies with Sub-nanomolar Affinities Isolated from a Large Non-immunized Phage Display Library", *Nature Biotech.*, 14(3):309-314 (1996).
Vitetta et al., "Redesigning nature's Poisons to Create Anti-Tumor Reagents", *Science*, 238:1098-1104 (1987).

Weijtens et al., "Single Chain Ig/YGene-Redirected Human T Lymphocytes Produce Cytokines, Specifically Lyse Tumor Cells, and Recycle Lytic Capacity," *J. Immunol.*, 157(2):836-843 (1996).

Yang et al., "A Randomized Trial of Bevacizumab, an Anti-Vascular Endothelial Growth Factor Antibody, for Metastatic Renal Cancer", *N. Eng'l. J. Med.*, 349(5):427-434 (2003).

Yang et al., "Cellular and Humoral Immune Responses to Viral Antigens Create barriers to Lung-Directed Gene Therapy with Recombinant Adenoviruses", *J. Virol.*, 69(4):2004-2015 (1995).

Zatovicova et al., "Monoclonal antibodies generated in carbonic anhydrase IX-deficient mice recognize different domains of tumour-associated hypoxia-induced carbonic anhydrase IX", *J. Immunol. Meth.*, 282(1-2):117-134 (2003).

Zavada et al., "Expression of MaTu-MN Protein in Human Tumor Cultures and in Clinical Specimens", Int. J. Cancer, 54:268-274(1993).

Zavada et al., "Human tumour-associated cell adhesion protein MN/CA IX: identification of M75 epitope and of the region mediating cell adhesion", *Brit. J. Cancer*, 82(11):1808-1813 (2000).

Zavada et al., "Transient transformation of mammalian cells by MN protein, a tumor-associated cell adhesion molecule with carbonic anyhdrase activity", *Int. J. Oncol.*, 10(4):857-863 (1997).

Zebedee et al., "Human combinatorial antibody libraries to hepatitis B surface antigen", *Proc. Nat'l. Acad. Sci. U.S.A.*, 89:3175-3179 (1992).

Zhu et al., "Development of constitutive and inducible self-inactivating lentiviral vectors and their application in cardiovascular gene transfer", *Gene Ther. Mol. Biol.*, 8:91-102 (2004).

Zuckermann et al., "Discovery of Nanomolar Ligands for 7-Transmembrane G-Protein-Coupled Receptors from a Diverse *N*-(Substituted)glycine Peptoid Library", *J. Med. Chem.*, 37:2678-2685 (1994).

Zufferey et al., "Self-Inactivating Lentivirus Vector for Safe and Efficient In Vivo Gene Delivery", *J. Virol.*, 72(12):9873-9880 (1998).

* cited by examiner

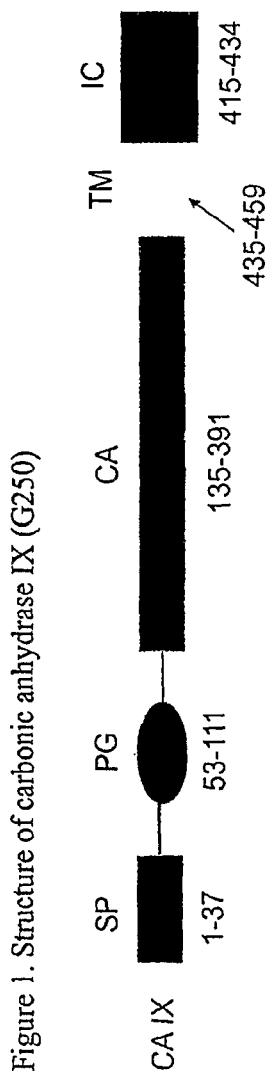

Figure 2. Multiple sequence alignment of amino acid sequences of anti-carbonic anhydrase IX (G250) single phage-scFv clones.

Figure 3. Alignment of human and mouse CA IX amino acid sequences.

```
            1         10        20        30        40        50         59
HCA IX    MAPLCPSPWLPLLIPAPAPGLTVQLLLSLLLLMPVHPQRLPRMQ-EDSPLGGGSSGEDDP
MCA IX    MASLGPSPWAPLSTPAP---TAQLLLFLLLQVSAQPQGLSGMQGEPS-LGDSSSGEDE- 61        70        80        90        100       110
HCA IX    LGEED-LPSEEDSPREE-DPPGEEDLPGEEDLPEVKPKSE---EEGSLKLEDLP
MCA IX    LGV-DVLPSEEDAP-EEADPP--D--GE-D-P-----PEVN--SEDRMEE-SLGLEDLS 120       130       140       150       160       170
HCA IX    TVEAPGDPQEP-QNNAHRD-KEGDDQSHMRYGGDPPWPRVSPACAGRFQSPVDIRPQLA-
MCA IX    TPEAP----EHSQGS-HGDEKGGGH-SHWSYGGTLLWPQVSPACAGRFQSPVDIR--LER 180       190       200       210       220       230
HCA IX    -AFCPALRPLELLGFQLPPLPELRLRNNGHSVQLTLPPGLEMALGPGREYRALQLHLHWG
MCA IX    TAFCRTLQPLELLGYELQPLPELSLSNNGHTVQLTLPPGLKMALGPGQEYRALQLHLHWG 240       250       260       270       280       290
HCA IX    AAGRPGSEHTVEGHRFPAEIHVVHLSTAFARVDEALGRPGGLAVLAAFLEEGPEENSAYE
MCA IX    TSDHPGSEHTVNGHRFPAEIHVVHLSTAFSELHEALGRPGGLAVLAAFLQESPEENSAYE 300       310       320       330       340        348
HCA IX    QLLSRLEEIAEEGS--ETQVPGLDISALLPSDFSRYFQYEGSLTTPPCAQGVIWTVFNQT
MCA IX    QLLSHLEEISEEGSKIE--IPGLDVSALLPSDFSRYYRYEGSLTTPPCSQGVIWTVFNET 360       370       380       390       400        408
HCA IX    VMLSAKQLHTLSDTLWGPGDSRLQLNFRATQPLNGRVIEASFPAGVDSSPRAAEPVQLNS
MCA IX    VKLSAKQLHTLSVSLWGPRDSRLQLNFRATQPLNGRTIEASFPAAEDSSP---EPVHVNS 420       430       440       450        459
HCA IX    CLAAGDILALVFGLLFAVTSVAFLVQMRRQHRR--GTKGGVSYRPAEVAETGA
HCA IX    CFTAGDILALVFGLLFAVTSIAFLLQLRRQHRHRSGTKDRVSYSPAEMTETGA
```

HCA IX: SEQ ID NO: 45; MCA IX: SEQ ID NO: 46.

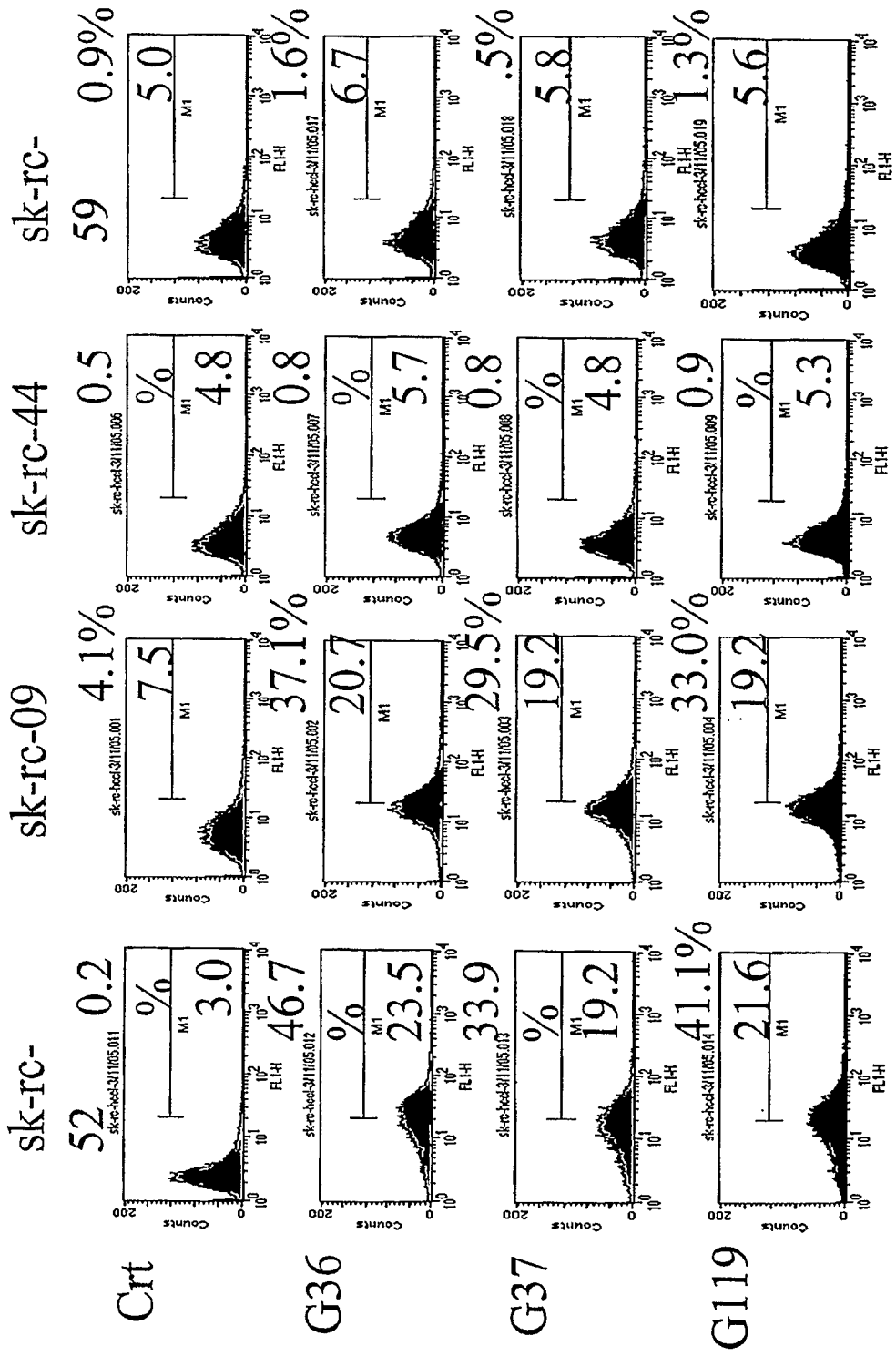
Figure 4. FACS analysis of human RCC cell lines contacted with purified anti-CA IX scFv antibodies

| ScFV | IC$_{50}$ (ug/mL) | I$_{MAX}$ | R VALUE |
|---|---|---|---|
| G45 | 1.2 | 193.4 | 0.9995 |
| G37 | 1.816 | 222.5 | 0.9907 |
| G98 | 2.04 | 193.1 | 0.9264 |
| G10 | 2.086 | 367.6 | 0.9594 |
| G40 | 3.98 | 150.2 | 0.9976 |
| G36 | 7.975 | 201.9 | 0.9706 |
| G6 | 11.09 | 326.1 | 0.9789 |
| G119 | 13.53 | 282.5 | 0.9769 |
| G39 | 15.99 | 258.2 | 0.9983 |
| G125 | 17.16 | 210.6 | 0.9928 |
| G21 | 17.43 | 287.7 | 0.9928 |
| G9 | 22.04 | 247.3 | 0.9973 |
| G27 | 27.03 | 250.9 | 0.9986 |
| G106 | 65.5 | 312.7 | 0.9758 |

| | IC50(nM) | Maxi GMFI |
|---|---|---|
| G45 | 1.2 | 351.5 |
| G40 | 2.6 | 275.47 |
| G36 | 2.6 | 376.15 |
| G119 | 2.9 | 415.23 |
| G10 | 2.9 | 367.8 |
| G106 | 3.4 | 359.54 |
| G37 | 3.9 | 401.8 |
| G39 | 5.1 | 476.23 |
| G125 | 6.4 | 252.1 |
| G98 | 16.9 | 336.88 |
| G57 | 17.6 | 422.61 |
| G27 | 30.3 | 283.94 |
| G6 | 33.3 | 238.54 |
| G21 | 151.9 | 112.67 |
| G9 | 310.5 | 160.53 |
| G104 | 478.9 | 104.75 |

| | GFP | | PE | |
|---|---|---|---|---|
| | % | MFI | % | MFI |
| Unstain | 1.20 | 18.74 | 0.37 | 20.40 |
| 2nd Ab | 1.37 | 16.38 | 2.48 | 20.95 |
| G10 | 60.83 | 761.49 | 43.13 | 140.82 |
| G39 | 61.41 | 434.25 | 38.32 | 93.27 |
| G92 | 61.37 | 782.81 | 37.47 | 133.72 |
| G98 | 56.32 | 887.72 | 27.06 | 128.88 |
| G62 | 62.01 | 779.39 | 39.55 | 124.78 |
| G36 | 55.46 | 817.95 | 27.17 | 114.36 |

Expression of Lv vector by ZsGreen
Anti-1D4 50ug/ml + anti-mouse PE

CARBONIC ANHYDRASE IX (G250) ANITBODIES

RELATED APPLICATIONS

This application is a national stage application, filed under 35 U.S.C. X371, of International Application No. PCT/US2006/046350, filed on Dec. 4, 2006 which claims the benefit of U.S. Ser. No. 60/742,149 filed Dec. 2, 2005.

GRANT SUPPORT

This invention was made with United States Government support under National Institutes of Health Grant DK072282. The United States Government may have certain rights in the invention.

INCORPORATION OF SEQUENCE LISTING

The contents of the text file named "20363_040N01_ST25.txt", which was created on Apr. 26, 2012 and is 58.0 KB in size, are hereby incorporated by reference in their entireties.

FIELD OF THE INVENTION

This invention relates generally to anti-carbonic anhydrase IX (G250) antibodies as well as to methods for use thereof.

BACKGROUND

Renal cell carcinoma (RCC) accounts for 3% of all adult malignancies and there are approximately 32,000 new cases diagnosed each year in the United States. RCC is resistant to virtually all conventional modes of treatment, such as radiotherapy and chemotherapy, reinforcing the urgent need for new therapies. RCC is a clinicopathologically heterogeneous disease, traditionally subdivided into clear cell, granular cell, papillary, chromophobe, spindle cell, cystic, and collecting duct carcinoma subtypes based on morphological features according to the WHO International Histological Classification of Kidney Tumors (Mostfi, 1998). Clear cell RCC is the most common adult renal neoplasm, representing 70% of all renal neoplasms, and is thought to originate in the proximal tubules. Clear cell RCC is mostly sporadic, unilateral, and unifocal. The main genetic alterations of clear cell RCC have been identified to be chromosome 3 alterations and Von Hippel-Landau (VHL) gene mutations (Walsh, 2003). pVHL is part of a novel multiprotein ubiquitin ligase complex, termed VBC (VHL/Elongin B/Elongin C), that recruits important cellular proteins for rapid degradation by the ubiquitin-proteasome proteolysis system. Among the cellular proteins that bind to VHL and are normally degraded under normoxic conditions is hypoxia-inducible transcription factor (HIF1). HIF1 is considered to be a master regulator gene that integrates pathways regulating physiological responses to acute and chronic hypoxia. HIF1 controls the expression of several dozen target genes, including those involved in energy metabolism (glucose transporters, glycolytic enzymes), angiogenesis [vascular endothelial growth factor (VEGF) and VEGFR-1], and surface transmembrane carbonic anhydrases (CAs) (Hanahan, 1996; Ivanov, 1998; Maxwell, 1999; Ohh, 1999; Semenza, 2000). In VHL-defective tumors, curiously enough, the two fundamental stages of tumor development occur either simultaneously or in reverse, first triggering the hypoxia-cellular response, followed by proliferation of transformed cells, consistent with the angiogenic phenotype of tumors seen in the VHL syndrome (Ivanov, 2001). RCC is one of the few tumors where spontaneous regression of metastatic disease has been documented after tumor nephrectomy, treatment with placebo in phase III trials or after inflammatory or infectious events (Bleumer, 2003; Michael, 2603). These observations have provided strong evidence of the importance of the immune system in the control of this cancer. Therefore, much attention has been focused on immunotherapeutic modalities for the treatment of RCC.

SUMMARY OF THE INVENTION

Provided herein are monoclonal antibodies which bind immunospecifically to the carbonic anhydrase IX (G250) protein. Specifically, such MAbs bind to the CA domain of the CA IX protein.

In one aspect, the invention provides an isolated antibody that immunospecifically binds to a carbonic anhydrase IX (G250) protein. The antibody binds to the carbonic anhydrase (CA) domain of carbonic anhydrase IX (G250). Optionally, the monoclonal antibody reduces carbonic anhydrase activity when contacted with CA IX. Exemplary antibodies of the invention include antibodies having a heavy chain with a CDR containing amino acids 99 to 111 of SEQ ID NO: 1 and a light chain with a CDR containing amino acids 91 to 102 of SEQ ID NO: 2. Alternatively, the antibody has a heavy chain with a CDR1 containing the amino sequence SYAMS (SEQ ID NO: 55), XYAMX (SEQ ID NO: 56), or SYXMX (SEQ ID NO: 57). The antibody has a heavy chain with a CDR2 containing an amino sequence AISXXGGXTXXADSVKG (SEQ ID NO: 58) or AISGSGGSTTTADSVKG (SEQ ID NO: 59), or the antibody has a heavy chain with a CDR3 containing an amino sequence NGNYRGSLXAFDI (SEQ ID NO: 60). The antibody has a light chain with a CDR1 containing an amino sequence TGSSSNIGAGYDVH (SEQ ID NO: 61), or the antibody has a light chain with a CDR2 containing an amino sequence GNNNRPS (SEQ ID NO: 62), or the antibody has a light chain with a CDR3 containing an amino sequence QSYDSSLSAWVV (SEQ ID NO: 63). The antibody is a monoclonal antibody or an scFv antibody or a minibody. Preferably, the binding affinity is from about $10^{-6}$ M to about $10^{-12}$ M. Exemplary scFv antibodies include scFv antibodies having a sequence of SEQ ID NO: 3-44.

In another aspect, the invention provides an antibody complex containing a first fully human monoclonal antibody that binds to a carbonic anhydrase IX (G250) protein, operably linked to a second fully human monoclonal antibody that binds to a carbonic anhydrase IX (G250) protein. Generally, the antibody complex reduces carbonic anhydrase activity. Preferably, the first and second antibodies do not bind to the same epitope.

In a further aspect, the invention provides a nucleic acid sequence containing a first nucleic acid encoding an anti-CA IX antibody or an anti-CA IX scFv antibody and second nucleic acid encoding a cytokine, such as IL-2 or the T-cell receptor or portion or subunit thereof. For example, the second nucleic acid is the zeta chain of the T-cell receptor complex. Optionally, the nucleic acid sequence contains a third nucleic acid sequence encoding a signaling region from a costimulatory protein such as CD28.

Also provided are methods for preventing or treating cancer by administering to a person at risk or suffering from cancer a therapeutically effective amount of a first antibody that is an anti-CA IX antibody. The cancer is, e.g., renal cancer such as renal clear cell cancer. In certain embodiments, the method also includes administering a second antibody that does not bind to the same epitope as the first anti-CA IX antibody. The second antibody may bind to a CA IX protein or another, non-CA IX protein. Exemplary antibodies that bind to non-CA IX proteins include Avastin, Erbitux, Humira, Xolair, Zavalin, Campath, Mylotarg, Herceptin, Remicaide, Simulect, Synagis, Zenapax, Rituxan, Panorex, ReoPro, Oncoscint, and OKT3. Optionally, the method also includes further administering a small molecule such as a neoplastic agent, or a cytokine, such as IL-2, GM-CSF, IL-12, or TNF-alpha.

The present invention also provides fusion proteins containing the antibodies of the invention. A fusion protein is, for example, an anti-CA XI antibody or a functional fragment thereof, operably linked to a cytokine or growth factor, such as an IL-2 polypeptide. Alternatively the fusion protein contains an anti-CA XI antibody or a functional fragment thereof, operably linked to an IgG molecule. In a further embodiment the fusion protein contains a an anti-CA XI antibody or a functional fragment thereof, operably linked to the T-cell receptor or fragment or subunit thereof. For example, the fusion protein contains the zeta chain of the T-cell receptor complex. Optionally, the fusion protein contains a third polypeptide which includes a signaling region from a costimulatory protein such as CD28.

Preferably, the antibody is human (i.e., the antibody does not contain any non-human antibody proteins) or humanized (i.e., the antibody is a non-human antibody such as a mouse antibody that has been modified to remove the majority of their mouse protein sequences; generally only the antigen-recognized sites, or complementarily-determining hypervariable regions (CDRs) are of non-human origin). As used herein, a minibody contains an antigen binding domain of an antibody and an immunoglobulin CH3 domain. For example, a minibody contains the binding domain of an anti-CA IX monoclonal antibody or scFv antibody, or a functional fragment thereof, and a constant region of an immunoglobulin or fragment thereof.

The invention also provides a composition containing an anti-CA IX monoclonal antibody or scFv and a carrier. Optionally, the composition contains one or more other components, such as a cytokine (e.g., IL-2) or a small molecule, such as an antineoplastic agent. The invention also provides a kit comprising, in one or more containers, these compositions.

In another aspect, the invention provides a method of quantitating the expression of a protein on or in a mammalian cell by providing a mammalian cell suspected of expressing a carbonic anhydrase IX (G250) protein, then contacting the cell with an anti-CA IX antibody or scFv antibody under conditions where the carbonic anhydrase IX (G250) protein and the antibody are capable of forming a complex, and detecting the amount of complex formation.

The invention also provides a method of modifying an immune effector cell by providing an immune effector cell obtained from a mammalian subject having renal cancer and contacting the immune effector cell with a nucleic acid encoding an anti-CA IX antibody or scFv, or a fragment thereof. The immune effector cell is a T cell. Generally, the nucleic acid comprises a vector, such as a retroviral vector. The invention also includes the modified immune effector cell educated by these methods, and the use of these modified immune effector cells to in methods of preventing or treating cancer, by administering to a person at risk or suffering from cancer (e.g. renal cancer) one or more modified immune effector cells. In such methods, one may also administer other compounds, such as anti-neoplastic agents, or cytokines such as IL-2, GM-CSF, IL-12, and TNF-alpha.

The invention also provides a method of detecting a carbonic anhydrase IX (G250) protein by providing a first detection means that includes an anti-CA IX antibody or scFv that is operably linked to a support means, contacting this first detection means with a biological sample suspected of containing a carbonic anhydrase IX (G250) protein under conditions where the carbonic anhydrase IX (G250) protein and the first detection means are capable of forming a complex, and detecting the amount of complex formation.

The invention further provides a method of detecting a carbonic anhydrase IX (G250) protein by contacting a biological sample suspected of containing a carbonic anhydrase IX (G250) protein with a first detection means containing a first fully human monoclonal antibody that binds to the carbonic anhydrase (CA) domain of a carbonic anhydrase IX (G250) protein under conditions where the carbonic anhydrase IX (G250) protein and the first detection means are capable of forming a complex, contacting the biological sample with a second detection means containing a second fully human monoclonal antibody that binds to the carbonic anhydrase (CA) domain of a carbonic anhydrase IX (G250) protein under conditions where the carbonic anhydrase IX (G250) protein and the second detection means are capable of forming a complex, and detecting the amount of complex formed between the carbonic anhydrase IX (G250) protein and the second detection means. In some embodiments, the first and second antibodies do not bind to the same epitope. Optionally, the second detection means contains a detectable moiety.

In another aspect, the invention provides a non-invasive method of detecting a tumor in a subject by administering to the subject an anti-CA IX antibody or scFv antibody linked to a detectable moiety, allowing for the localization of the antibody in the tumor, and detecting the detectable moiety. The detectable moiety comprises a radioactive element, and the detecting is performed by positron emission tomography.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 1 is a schematic illustration of the carbonic anhydrase IX (G250) polypeptide. The signal peptide (SP), proteoglycan region (PG), carbonic anhydrase domain (CA), transmembrane domain (TM) and intracellular domains (IC) are labeled. The amino acids corresponding to these regions are provided below the regions.

FIG. 2 is a multiple sequence alignment of amino acid sequences of single phage-scFv clones described herein. A consensus sequence is provided in bold above the alignments.

FIG. 3 is a sequence alignment of human (HCA IX; SEQ ID NO:45) and murine (MCA IX; SEQ ID NO: 46) CA IX amino acid sequence orthologs. Amino acids that are similar to or identical in human and murine CA IX polypeptides are shaded.

FIG. 4 is a series of graphs showing FACS analyses of human RCC cell lines (sk-rc-52, sk-rc-09, sk-rc-44, and sk-rc-59) contacted with purified anti-CA IX scFv antibodies (G36, G37 and G119; Crt is a control).

FIG. 14 is a chart showing the quantitation of binding ($IC_{50}$) of anti-CA IX (G250) scFvs to stable G250-expressing 293T cells.

FIG. 22 is a chart showing the quantitation of binding ($IC_{50}$) of anti-CA IX (G250) scFvs to stable G250-expressing 293T cells.

Figure 23:
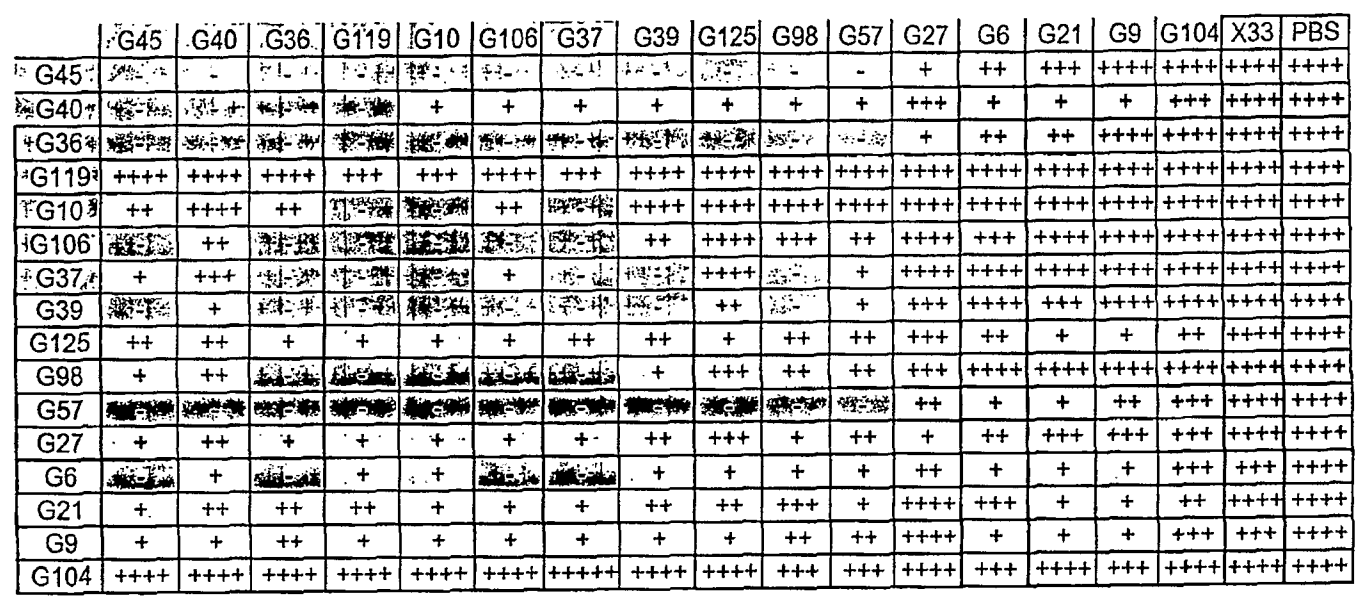

FIG. 23 is a table showing the results of cross competition of anti-G250-FCs.

FIG. 26 is a table showing expression of anti-G250scFv and C9 TCRs on 293T cell. Human primary Tcells were transduced with a self-inactivating lentiviral vector encoding clone G36 anti-CA IX(G250) chimeric T-cell receptor in cassette one and IRES driven expression of ZsGreen in cassette two. After two overnight transductions on consecutive days, the cells were stained for chimeric T-cell receptor expression using APC labeled Mab 1D4 which is directed against the C9 tag located immediately after the scFv and before the CD28 ECD. Transduction of two different human donors is shown.

DETAILED DESCRIPTION OF THE INVENTION

Figure 5:
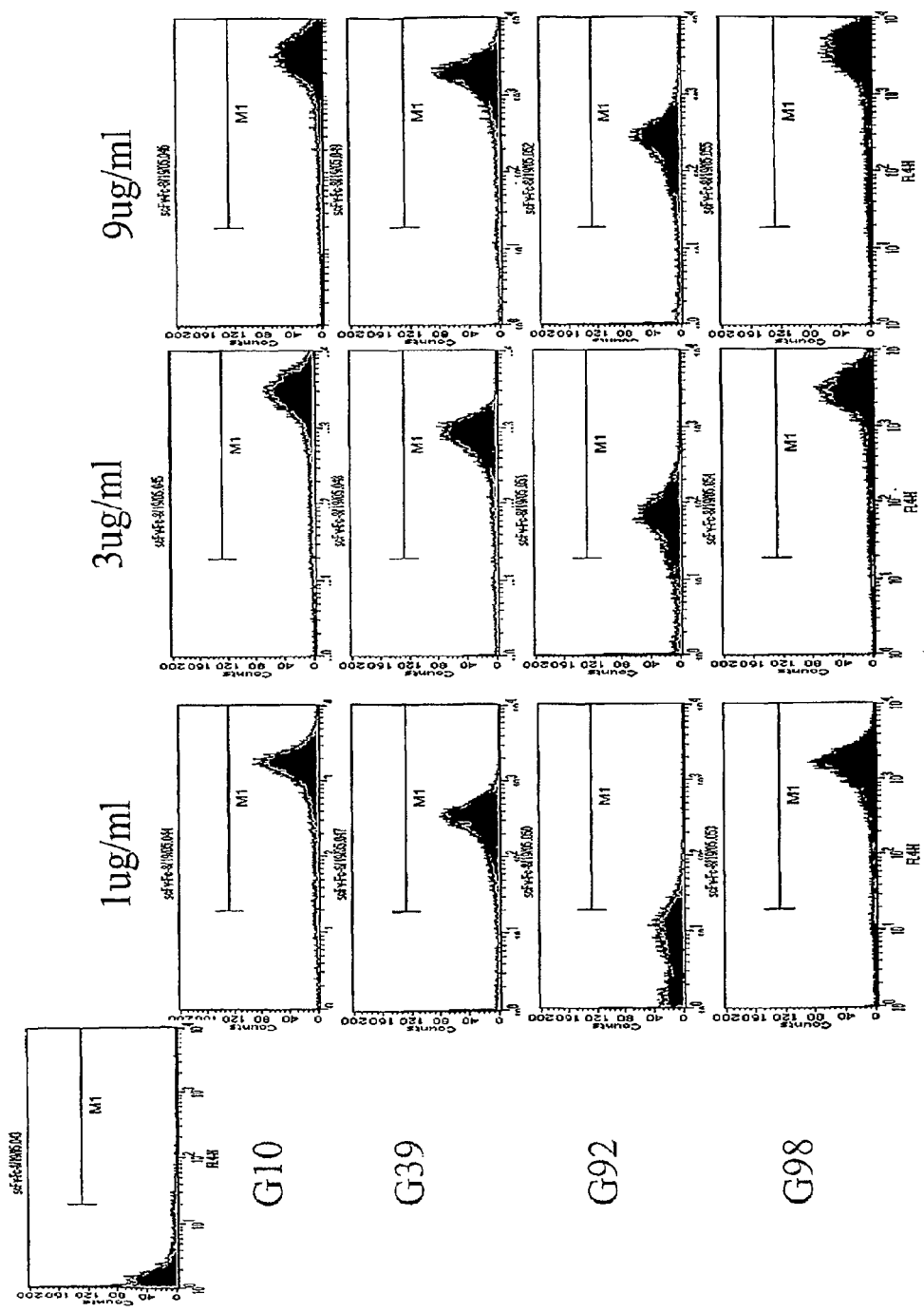
FIG. 5 is a series of graphs showing FACS analyses of a human RCC cell line (sk-rc-52) contacted with increasing concentrations of purified anti-CA IX scFv antibodies (G10, G39, G92 and G98). The control graph is shown in the upper left.

The invention is based in part on the discovery of antibodies that bind immunospecifically to carbonic anhydrase IX (CA IX).

A number of mAbs have been identified that react with surface antigens on RCC. These include mAbs that recognize differentiation and overexpressed antigens as well as mAbs that identify RCC-associated antigens not expressed in normal kidney (Michael, 2003; Yang, 2003). Of these, antibodies against the carbonic anhydrase IX (CA IX), epidermal growth factor receptor (EGFR) and VEGF are the most studied and have shown the greatest promise for treatment of RCC. The gene for CA IX, also known as G250 and MN is located on chromosomes 9p12 to 13 and encodes a transmembrane protein that binds zinc and has CA activity (Zavada, 1997; Grabmaier, 2000). In HeLa cells derived from human carcinoma of cervix uteri and in RCC cell lines, CA IX/G250/MN/ is found both at the plasma membrane and as a nuclear protein with apparent molecular weights of 58 and 54 kDa. It is N-glycosylated, and in the nonreduced state it forms oligomers (Pastorekova, 1992). Sequence analysis of the predicted CA IX protein shows that it contains a signal peptide (aa 1-37), an extracellular (EC) part (aa 38-414), a hydrophobic transmembrane region of 20 amino acids (aa 415-434) and a small C-terminus cytoplasmic portion of 25 amino acids (aa 435-459) (FIG. 1). The human and murine CA IX amino acid sequences are shown in FIG. 3. The extracellular portion is composed of two distinct domains. The region between the signal peptide and the CA domain (aa 53-111) shows significant homology (38% identity) with a keratin sulfate attachment domain of a human large aggregating proteoglycan, aggrecan (Doege, 1991). In the PG-like domain of CA IX, a hexapeptide motif with consensus E-E-D-L-P-E (SEQ ID NO: 64) is repeated 7 times. The carbonic anhydrase domain is located close to the plasma membrane (aa 135-391). The CA IX antigen appears at malignant transformation and stains positive in about 95% of clear cell RCC specimens as well as in most renal cell metastases. Results of a recent investigation focused on the genes involved in VHL-mediated carcinogenesis demonstrated down-regulation of CA IX gene expression in RCC cell lines by wild-type VHL transgenes (Ivanov, 1998). Conversely, in VHL-defective tumors, CA IX is overexpressed (Ivanov, 2001).

Epitopes expressed on the cell surface of tumor cells are superior targets for humoral anti-cancer therapy since, unlike intracellular antigens, they are accessible to circulating antibodies in vivo. In the last few years, human monoclonal antibodies (mAbs) have become a well tolerated treatment option in an increasing number of cancers. The concept of selective tumor targeting with antibodies is based on the avid interaction between the antibody and an antigen that is expressed on malignant cells, but not on normal tissues. Many mechanisms have been proposed for the ability of antibodies against tumors to mediate their effects in vivo. For example, engagement of the antibody Fc domain with effector cell FcγRs leads to antibody-dependent cell-mediated cytotoxicity (ADCC). Some (antagonist or inhibitory) antibodies can block the signaling on tumor cells and in this way may act synergistically with immune effector responses by rendering the tumor cells more susceptible to immune effector cell triggered apoptosis or lytic cell death (Baselga, 1998). Another way that antibodies can be utilized is through the construction and functional expression of chimeric-immune receptors or "T-bodies" on T-lymphocytes otherwise known as "designer T-cells". The antigen binding domain of the chimeric receptor consists of a single-chain antibody (scFv) while the intracellular signaling domain is derived from the cytoplasmic part of a membrane-bound receptor that is capable of inducing cellular activation (e.g. the FcεRI receptor γ-chain or the CD3 ζ-chain (Maher, 2002; Pinthus, 2003)). T-lymphocytes grafted with a chimeric receptor have the combined advantages of MHC-independence and antibody-based antigen binding with efficient T-cell activation upon specific binding to the receptor ligand. This activation results in the production and secretion of cytokines such as IL-2, interferon, GM-CSF and TNF-α. Antigen-specific lysis of tumor cells both in vitro and in vivo have been reported. T-lymphocytes can be permanently grafted with antigen-specific chimeric receptors by retroviral transduction of vector constructs encoding the receptor molecule of choice (reviewed by Rivière, 2004).

Identification and Characterization of scFvs and Monoclonal Antibodies

Unique anti-CA IX scFvs were identified by sequencing analysis of individual clones. The VH and VL sequences of these scFvs are shown in FIG. 2. The gene families for these scFvs were VH3 for heavy chains and VL1 or VL3 for light chains. As described herein, the CA IX (G250) antibodies are human antibodies having a high affinity, and are generally directed to the CA domain of the protein. The CA domain comprises amino acids 145-391 of the human CA IX protein. The antibody of the invention binds to 5, 10, 20, 50, 100 or more residues of the CA domain.

FACs Analysis of Anti-CA IX scFv Antibodies.

FACS analysis of several CA IX antibodies showed the specificity of these single chain antibodies for antigens present on a plurality of human RCC cell lines, as shown in FIG. 4. Titration analysis of several single chain antibodies, shown in FIG. 5, was also performed.

Epitope Characterization.

Figure 6:
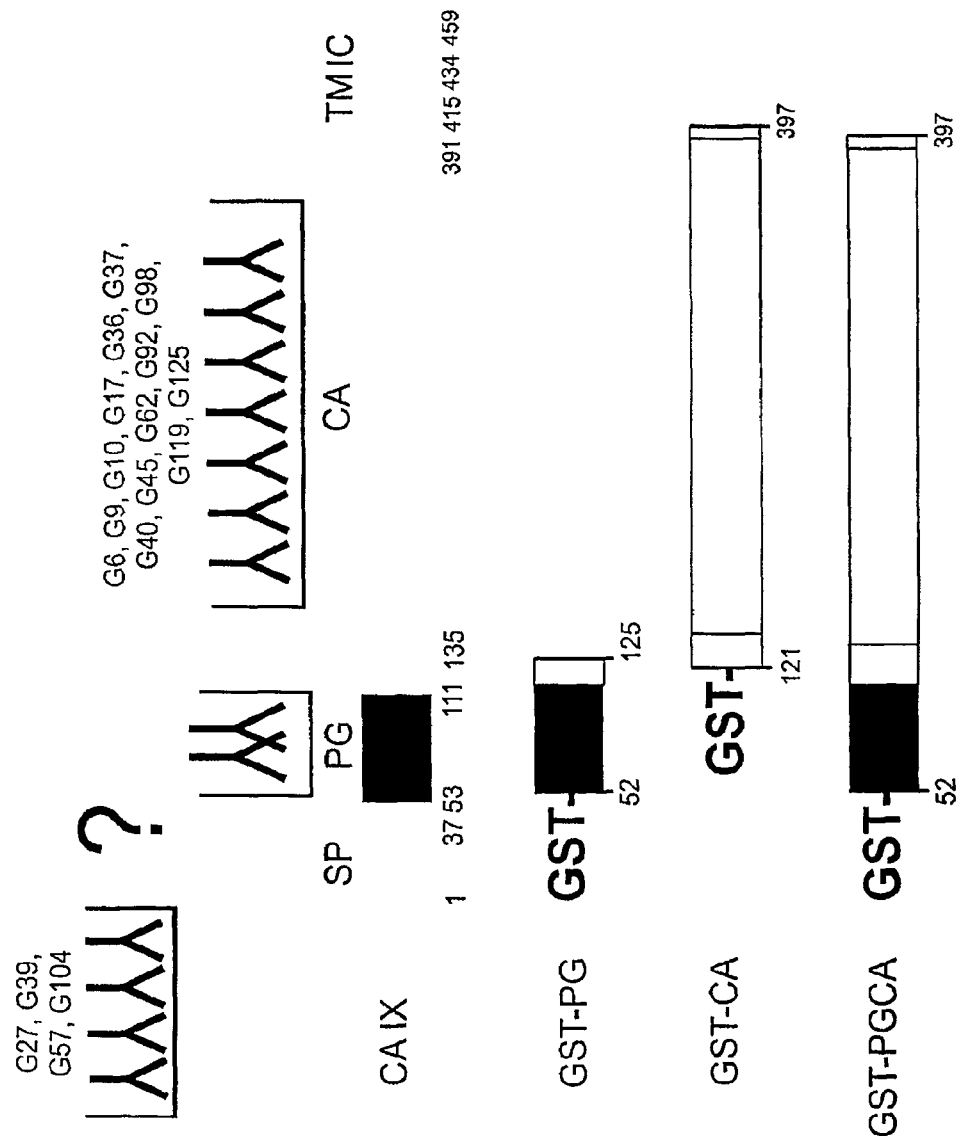
FIG. 6 is a schematic illustration showing epitope mapping of the regions of the CA IX polypeptide to which various scFv antibodies of the invention bind.
Figure 7:
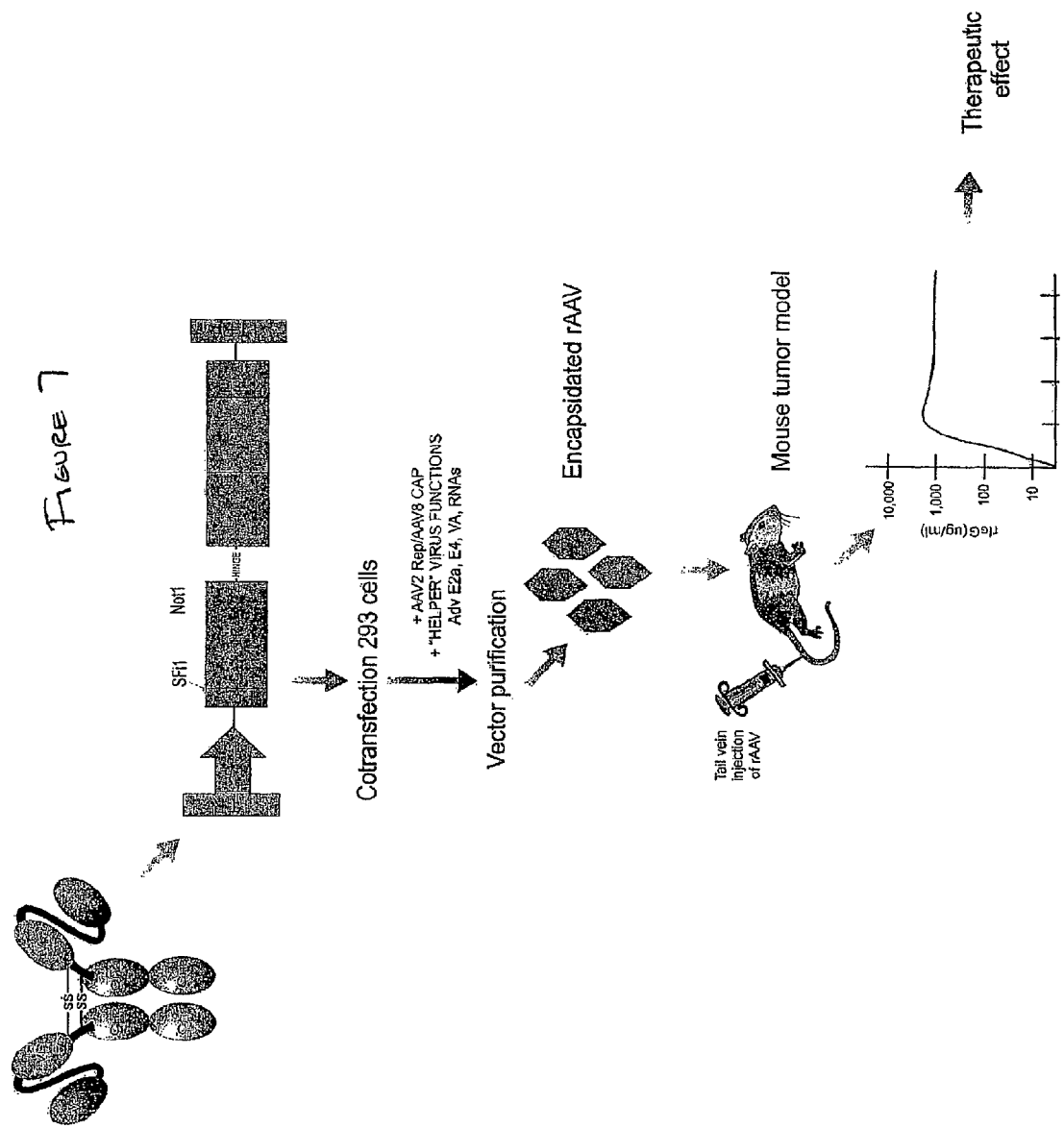
FIG. 7 is a schematic illustration showing methods for therapeutic antibody gene transfer.
Figure 8:
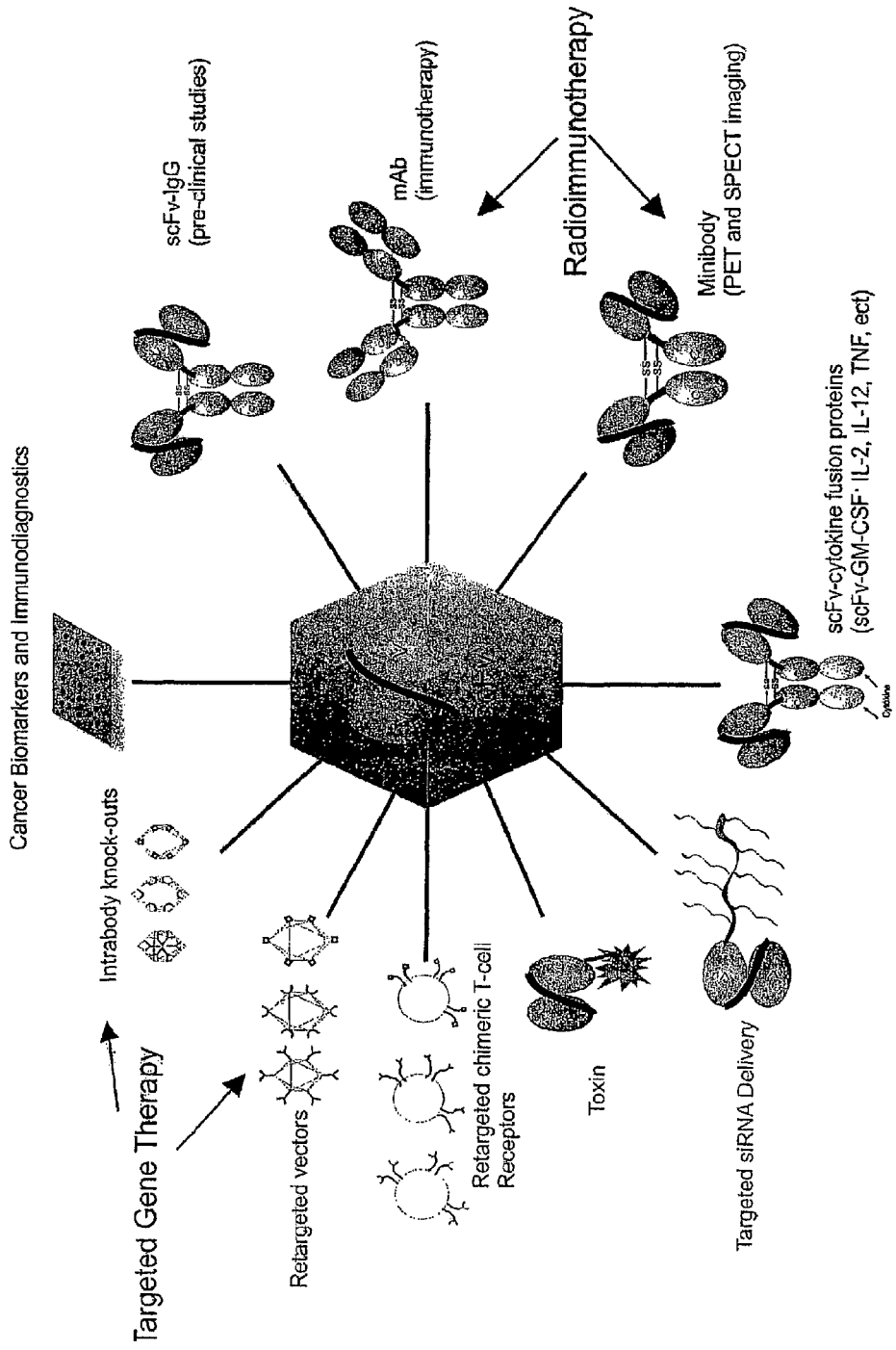
FIG. 8 is a schematic illustration showing various methods for diagnostic and therapeutic uses of the antibodies of the invention.
Figure 13:
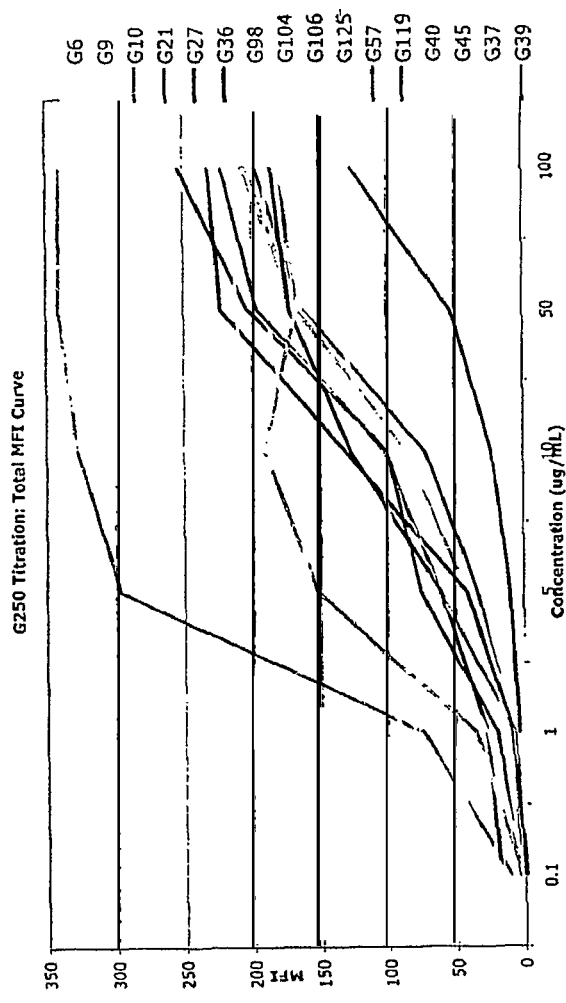
FIG. 13 is a line graph showing saturation binding of anti-CA IX (G250) scFvs to stable G250-expressing 293T cells. The vertical axis is mean fluorescence intensity (MFI) and the horizontal axis is concentration of the antibody (in µg/ml).
Figure 15:
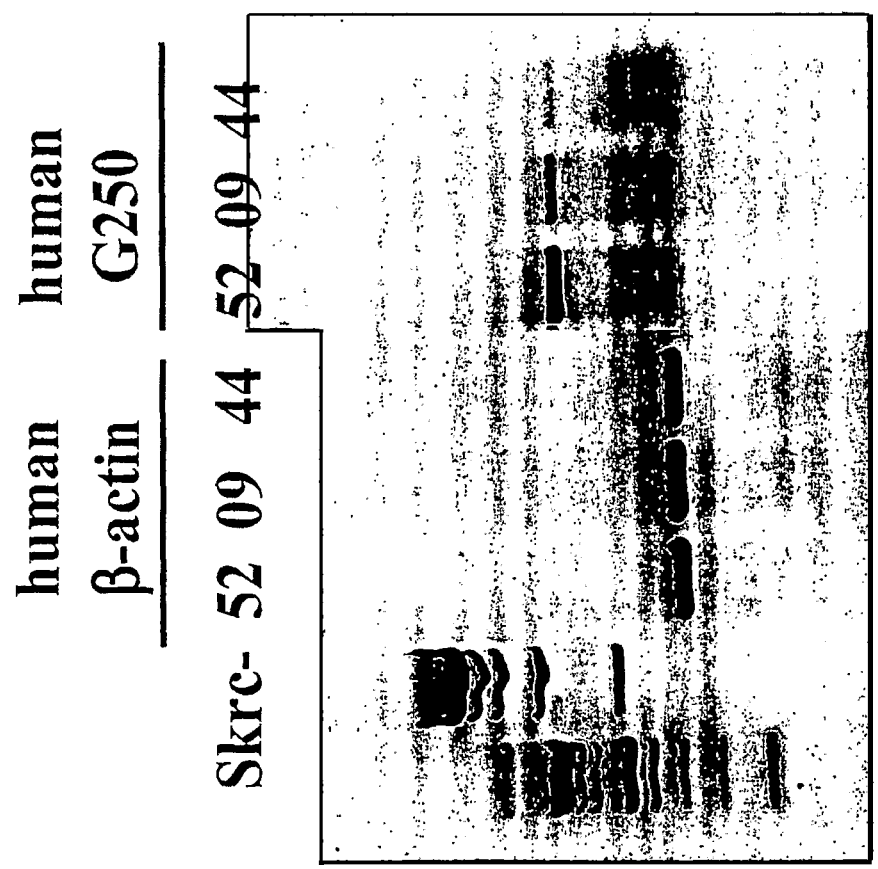
FIG. 15 is a photograph of a gel demonstrating amplification of a CA IX (G250) nucleic acid sequence from SK-RC renal cancer cell lines (sk-rc-52, -09, and -44). Beta actin is shown as a PCR control.
Figure 16:
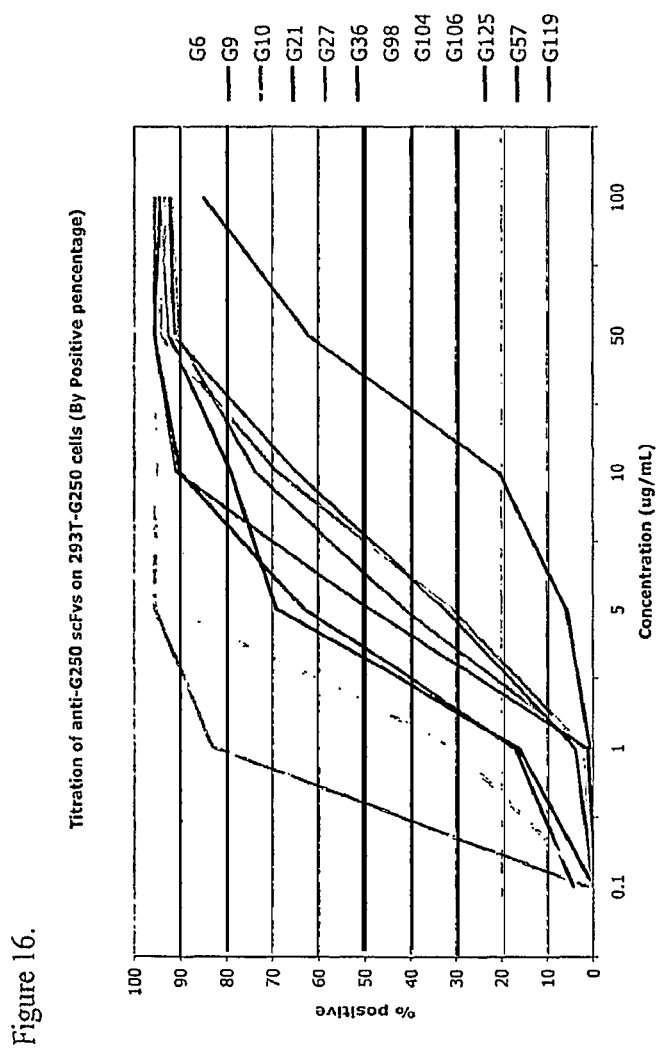
FIG. 16 is a line graph showing titration of anti-CA IX (G250) scFvs to stable G250-expressing 293T cells. The vertical axis is % of positive cells and the horizontal axis is concentration of the antibody (in µg/ml).
Figure 17:
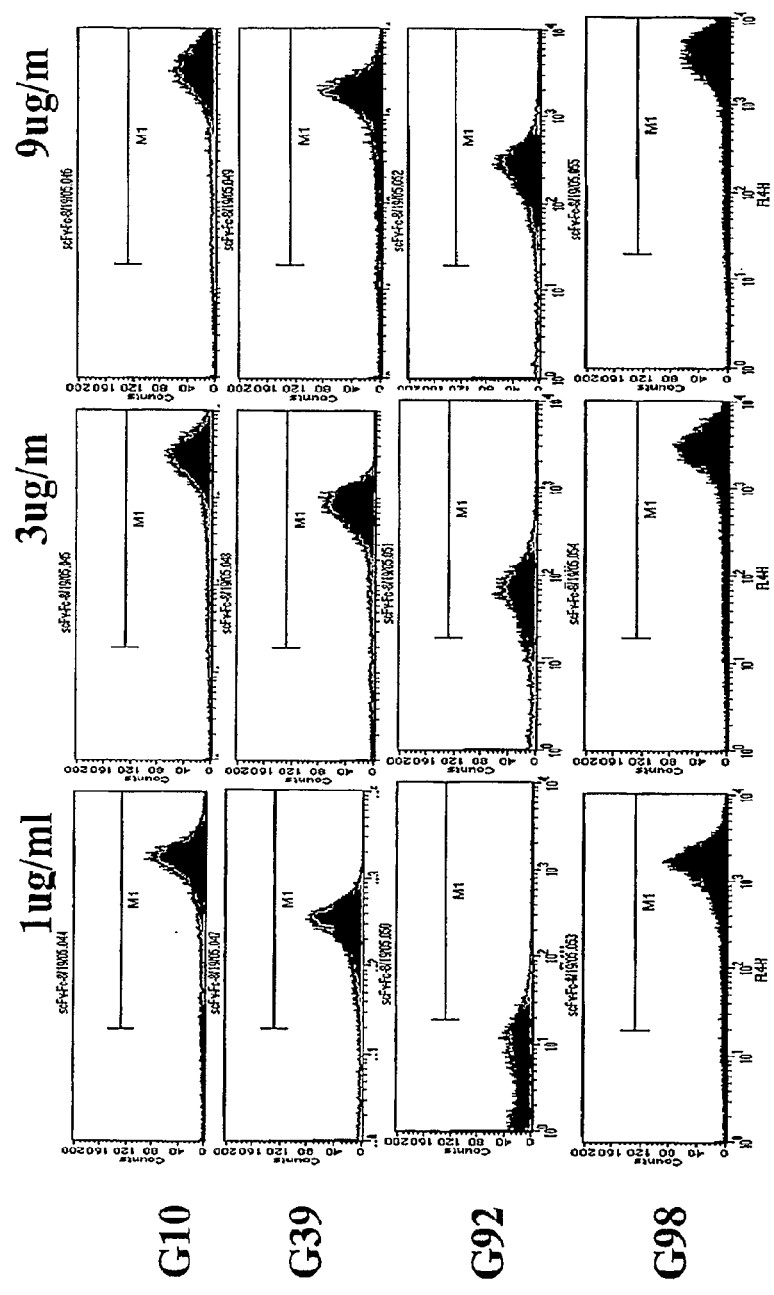
FIG. 17 is a series of graphs showing FACS analyses of a G250-positive human RCC cell line with anti-CA IX scFv-Fc fusion proteins. Compared with their monovalent counterparts, the divalent scFv-Fc fusion proteins showed more potent ability to bind to RCC cell line SK-RC-09 which expresses G250 molecule on the surface.
Figure 18:
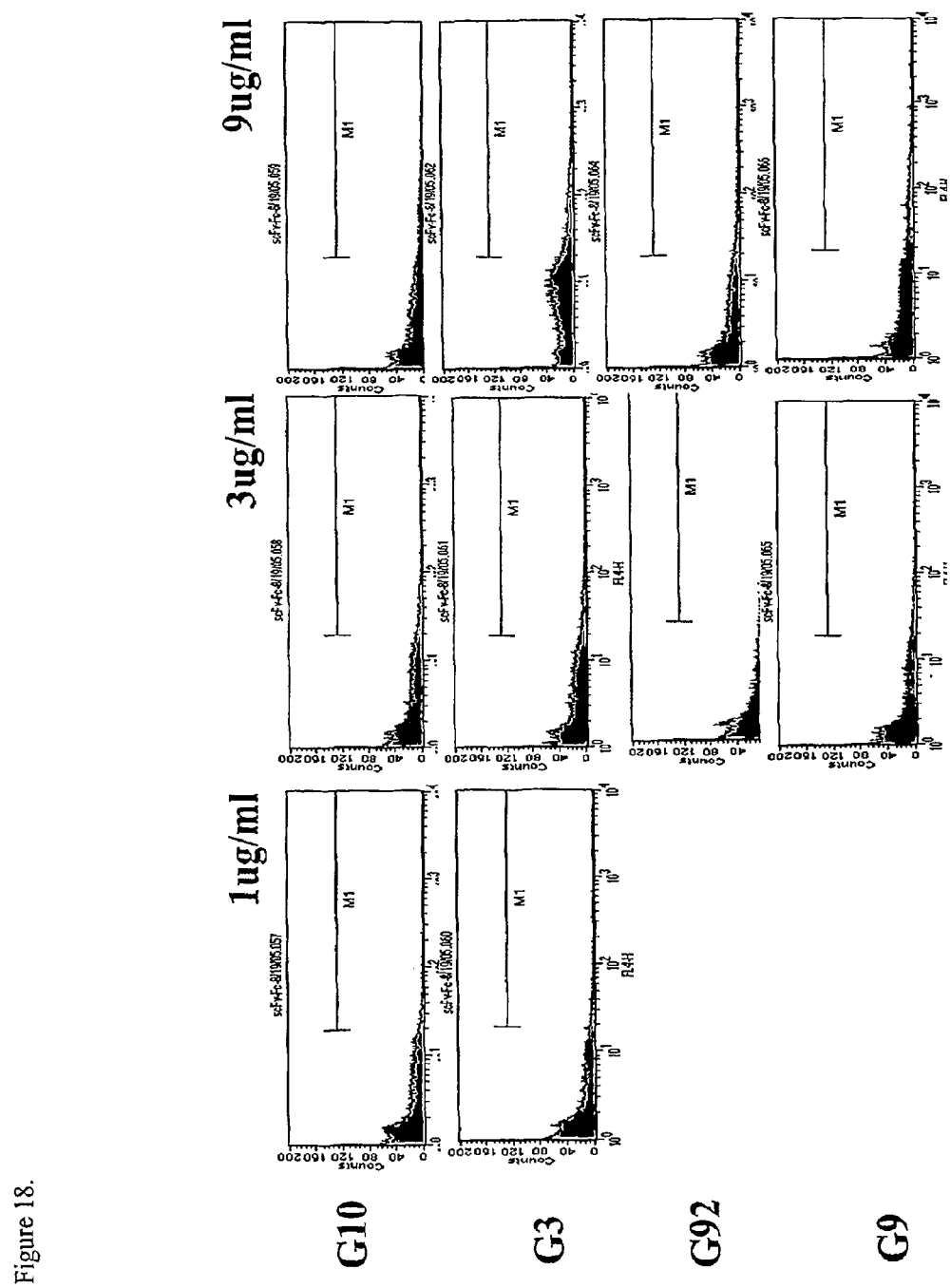
FIG. 18 is a series of graphs showing FACS analyses of a G250-negative human RCC cell line with anti-CA IX scFv-Fc fusion proteins.
Figure 19:
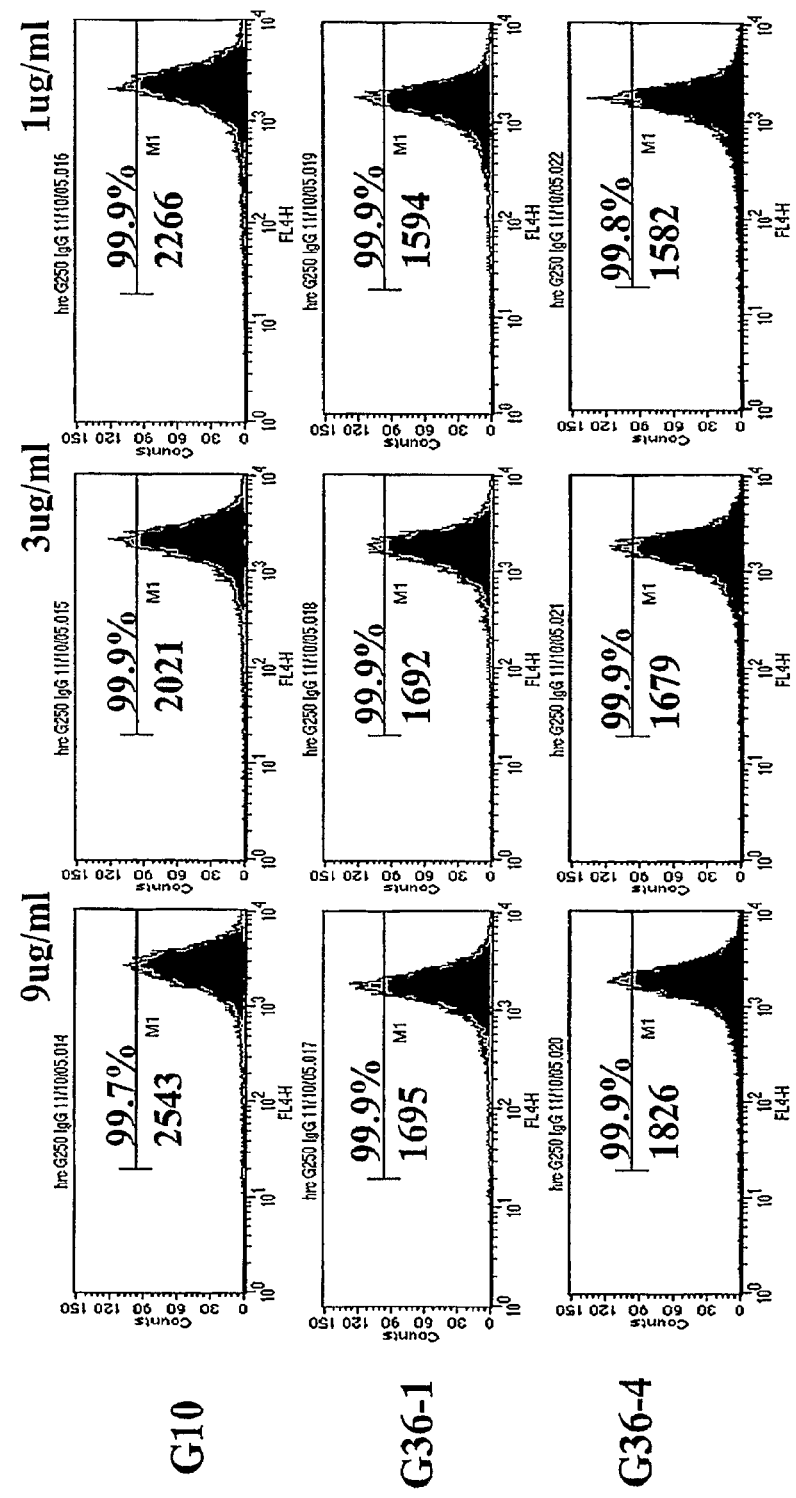
FIG. 19 is a series of graphs showing FACS analyses of a G250-positive human RCC cell line with full lengths anti-CA IX human IgG. Cell staining result indicated that full length human IgG showed much better binding to RCC cell line SK-RC-09 which expresses G250 molecule on the surface comparing with their scFvs counterparts. In each panel the upper number is the positive percentage and the lower number is MFI for each sample
Figure 20:
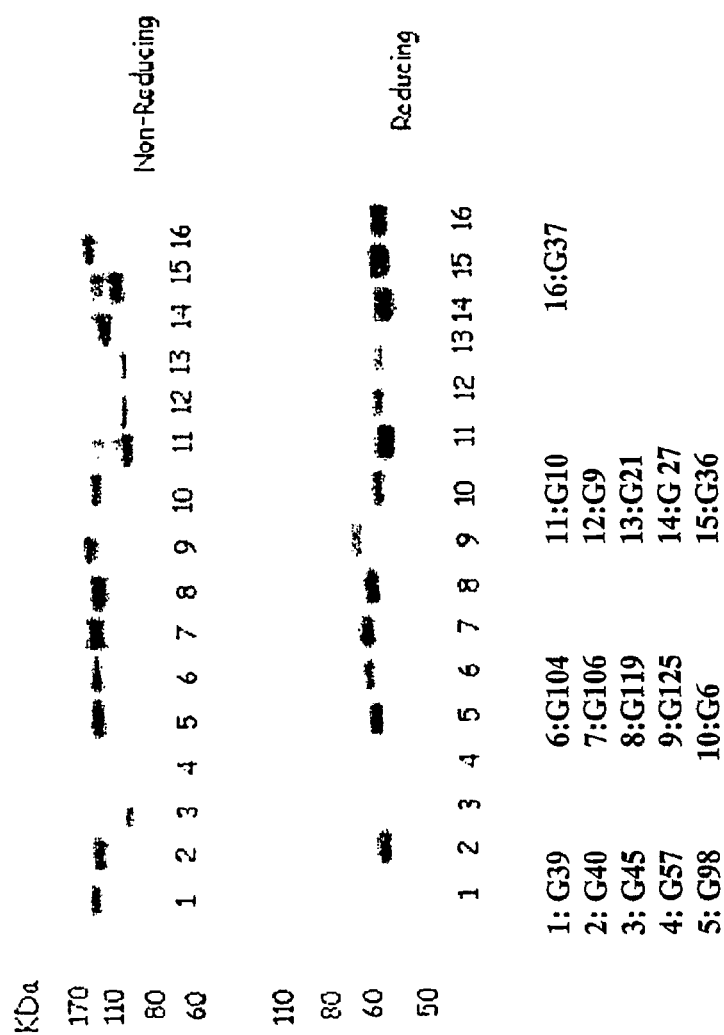
FIG. 20 is a photograph of SDS-PAGE gel of seventeen scFv-Fc antibody proteins under reducing and non-reducing conditions.
Figure 21:
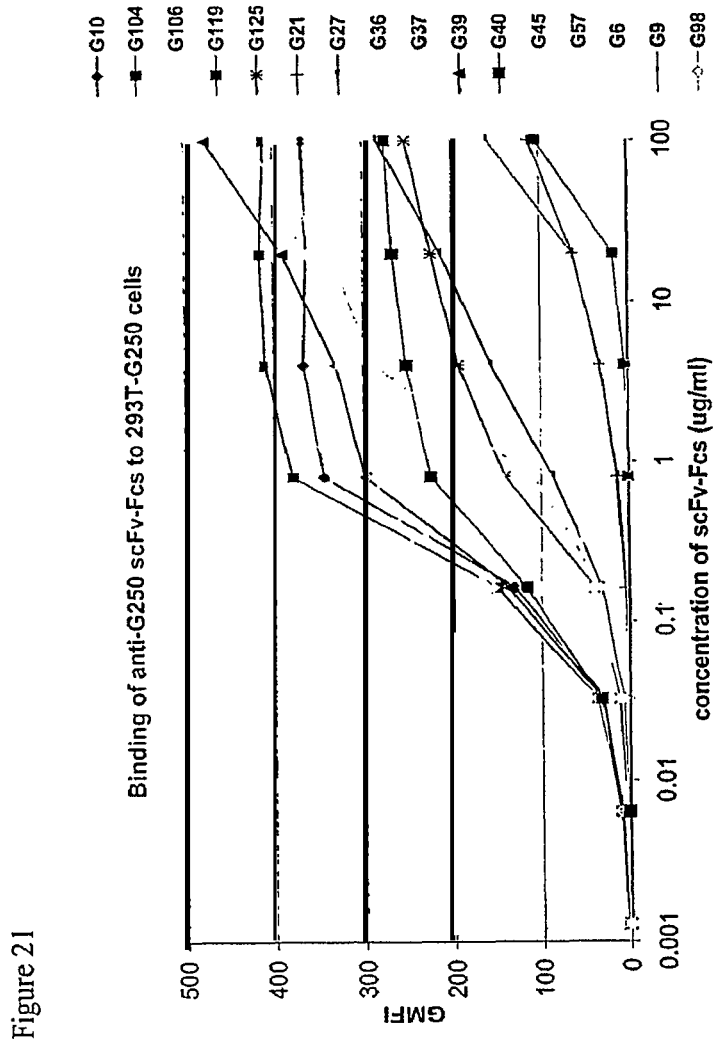
FIG. 21 is a line graph showing titration of anti-CA IX (G250) scFvs to stable G250-expressing 293T cells. The vertical axis is mean fluorescence intensity (GMFI) and the horizontal axis is concentration of the antibody (in µg/ml).

Primary epitope mapping of several single chain antibodies to the CA IX protein showed that numerous antibodies are directed to the CA domain rather than the immunodominant PC domain, as shown in FIG. 6. Specificity of binding to the CA domain for several scFvs is demonstrated in FIG. 13.

Internalization Studies.

Table 1 show the results of internalization studies of anti-CA IX scFv-Fc antibody fusion proteins into stable G250-293T cells.

TABLE 1

| Clone: | After 1 hour at 37°: | | After 1 hour at 4°: | |
|---|---|---|---|---|
| | % Positive | MFI | % Positive | MFI |
| G10-Fc | 99.98 | 2239 | 99.84 | 2017 |
| G17-Fc | 99.93 | 1260 | 99.96 | 1360 |
| G36-Fc | 99.95 | 2029 | 99.96 | 2058 |
| G39-Fc | 99.92 | 1865 | 99.97 | 1918 |
| G119-Fc | 99.95 | 2064 | 99.99 | 2285 |

MFI = mean fluorescence intensity.

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, chimeric, dAb (domain antibody), single chain, $F_{ab}$, $F_{ab'}$ and $F_{(ab')2}$ fragments, scFvs, and $F_{ab}$ expression libraries.

A single chain Fv ("scFv") polypeptide molecule is a covalently linked $V_H$::$V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." CDRs for the VH and VL regions of the scFv antibodies are shown in FIG. 2.

As used herein, the term "epitope" includes any protein determinant capable of specific binding to an immunoglobulin, an scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a CA IX epitope when the equilibrium binding constant ($K_d$) is $\leq 1$ µM, preferably $\leq 100$ nM, more preferably $\leq 10$ nM, and most preferably $\leq 100$ pM to about 1 pM, as measured by assays such as radioligand binding assays or similar assays known to those skilled in the art.

An CA IX protein of the invention, or a derivative, fragment, analog, homolog or ortholog thereof, may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to the CA domain of CA IX. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the CA IX protein, with which it is normally reactive, and then add the human monoclonal antibody being tested to determine if the human monoclonal antibody being tested is inhibited in its ability to bind the CA domain. If the human monoclonal antibody being tested is inhibited then, in all likelihood, it has the same, or functionally equivalent, epitopic specificity as the monoclonal antibody of the invention. Screening of human monoclonal antibodies of the invention, can be also carried out by utilizing CA IX and determining whether the test monoclonal antibody is able to neutralize CA IX.

Various procedures known within the art may be used for the production of polyclonal or monoclonal antibodies directed against a protein of the invention, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816, 567. DNA encoding the monoclonal antibodies of the invention can be readily isolated and sequenced using conventional procedures (e.g. by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95102140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as *orthopox* or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl Acad. Sci. USA 87:1149 (1990), Adenovirus Vectors (see LeGal LaSalle et al., Science, 259:988 (1993); Davidson, et al., Nat. Genet. 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266: 292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of CA IX in a sample. The antibody can also be used to try to bind to and disrupt a CA IX activity.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238: 1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio)propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against CA IX (G250)

Methods for the screening of antibodies that possess the desired specificity include, but are not limited to, enzyme linked immunosorbent assay (ELISA) and other immunologically mediated techniques known within the art.

Antibodies directed against a CA IX (G250) protein (or a fragment thereof) may be used in methods known within the art relating to the localization and/or quantitation of a CA IX protein (e.g., for use in measuring levels of the CA IX protein within appropriate physiological samples, for use in diagnostic methods, for use in imaging the protein, and the like). In a given embodiment, antibodies specific to a CA IX protein, or derivative, fragment, analog or homolog thereof, that contain the antibody derived antigen binding domain, are utilized as pharmacologically active compounds (referred to hereinafter as "Therapeutics").

An antibody specific for a CA IX protein of the invention can be used to isolate a CA IX polypeptide by standard techniques, such as immunoaffinity, chromatography or immunoprecipitation. Antibodies directed against a CA IX protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies of the invention, including polyclonal, monoclonal, humanized and fully human antibodies, may used as therapeutic agents. Such agents will generally be employed to treat or prevent cancer in a subject. An antibody preparation, preferably one having high specificity and high affinity for its target antigen, is administered to the subject and will generally have an effect due to its binding with the target. Administration of the antibody may abrogate or inhibit or interfere with an activity of the AC IX protein.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding a CA IX protein or a fragment thereof of the invention, as well as other molecules identified by the screening assays disclosed herein, can be administered for the treatment of cancer or other proliferative disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of CA IX (or a protein or a protein fragment thereof) in a sample. Preferably, the antibody contains a detectable label. Antibodies can be polyclonal, or more preferably, monoclonal. An intact antibody, or a fragment thereof (e.g., $F_{ab}$, scFv, or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens, antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers are physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Methods

The invention provides methods (also referred to herein as "screening assays") for identifying modulators, i.e., candidate or test compounds or agents (e.g. peptides, peptidomimetics, small molecules or other drugs) that modulate or otherwise interfere with an CA IX activity. Also provided are methods of identifying compounds useful to treat cancer. The invention also encompasses compounds identified using the screening assays described herein.

For example, the invention provides assays for screening candidate or test compounds which modulate the CA IX carbonic anhydrase activity. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37:1233.

Libraries of compounds may be presented in solution (see e.g. Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233, 409.).

In one embodiment, a candidate compound is introduced to an antibody-antigen complex and determining whether the candidate compound disrupts the antibody-antigen complex, wherein a disruption of this complex indicates that the candidate compound modulates an CA IX activity.

In another embodiment, at least one CA IX protein is provided, which is exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat cancer or a proliferative disease or disorder, particularly a renal proliferative disorder.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a CA IX neutralizing antibody. Additionally, the antigen may be a CA IX protein, or a portion thereof (e.g., the CA domain).

The screening methods disclosed herein may be performed as a cell-based assay or as a cell-free assay. In the case of cell-free assays comprising the membrane-bound forms of the CA IX proteins, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody or the antigen (e.g. the CA IX protein or the CA domain thereof) can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical) Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention can be detected by appropriate assays, e.g., conventional types of immunoassays. For example, a sandwich assay can be performed in which a CA IX protein or fragment thereof (e.g., the CA domain) is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide is subsequently incubated with a second, labeled antibody or antibody bound to a coupling agent such as biotin or avidin. This second antibody may be another anti-CA IX antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

The anti-CA IX antibodies and scFv antibodies of the invention, when joined to a detectable moiety, provides a way for detecting "cancerous tissue" or tissue subject to aberrant cell proliferation and therefore at risk for cancer. In addition to tissue that becomes cancerous due to an in situ neoplasm, for example, the antibody-detectable moiety conjugates also provides a method of detecting cancerous metastatic tissue present in distal organs and/or tissues. Thus such tissue may be detected by contacting tissue suspected of being cancerous with the antibody-detectable moiety under appropriate conditions to cause the detectable moiety to be detected in cancerous tissue, thereby detecting the presence of cancerous tissue.

The detectable moieties can be conjugated directly to the antibodies or fragments, or indirectly by using, for example, a fluorescent secondary antibody. Direct conjugation can be accomplished by standard chemical coupling of, for example, a fluorophore to the antibody or antibody fragment, or through genetic engineering. Chimeras, or fusion proteins can be constructed which contain an antibody or antibody fragment coupled to a fluorescent or bioluminescent protein. For example, Casadei, et al., describe a method of making a vector construct capable of expressing a fusion protein of aequorin and an antibody gene in mammalian cells.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject (such as a biopsy), as well as tissues, cells and fluids present within a subject. That is, the detection method of the invention can be used to detect cancer, a cancer cell, or a cancer-associated cell (such as a stromal cell associated with a tumor or cancer cell) in a biological sample in vitro as well as in vivo. For example, in vitro techniques for detection of CA IX include enzyme linked immunosorbent assays (ELISAs), Western blots, immunoprecipitations, and immunofluorescence. Furthermore, in vivo techniques for detection of CA IX include introducing into a subject a labeled anti-CA IX antibody. For example, the antibody can be labeled with a radioactive marker whose presence and location in a subject can be detected by standard imaging techniques. In embodiments, the invention provides a non-invasive method of detecting a tumor or cancer cell in a subject. The subject is administered an antibody or scFv antibody of the invention, where the antibody is linked to a detectable moiety (i.e., any moiety capable of being detected by, e.g., fluorescent, chemical, chemiluminescent, radioactive, or other means known in the art), the antibody is allowed to localize to the tumor then is detected by observation of the detectable moiety.

Localization of the detectable moiety. In the case of "targeted" conjugates, that is, conjugates which contain a targeting moiety—a molecule or feature designed to localize the conjugate within a subject or animal at a particular site or sites, localization refers to a state when an equilibrium between bound, "localized", and unbound, "free" entities within a subject has been essentially achieved. The rate at which such an equilibrium is achieved depends upon the route of administration. For example, a conjugate administered by intravenous injection to localize thrombi may achieve localization, or accumulation at the thrombi, within minutes of injection. On the other hand, a conjugate administered orally to localize an infection in the intestine may take hours to achieve localization. Alternatively, localization may simply refer to the location of the entity within the subject or animal at selected time periods after the entity is administered. By way of another example, localization is achieved when an moiety becomes distributed following administration.

In all of the above cases, a reasonable estimate of the time to achieve localization may be made by one skilled in the art. Furthermore, the state of localization as a function of time may be followed by imaging the detectable moiety (e.g., a light-emitting conjugate) according to the methods of the invention, such as with a photodetector device. The "photodetector device" used should have a high enough sensitivity to enable the imaging of faint light from within a mammal in a reasonable amount of time, and to use the signal from such a device to construct an image.

In cases where it is possible to use light-generating moieties which are extremely bright, and/or to detect light-generating fusion proteins localized near the surface of the subject or animal being imaged, a pair of "night-vision" goggles or a standard high-sensitivity video camera, such as a Silicon Intensified Tube (SIT) camera (e.g., from Hammamatsu Photonic Systems, Bridgewater, N.J.), may be used. More typically, however, a more sensitive method of light detection is required.

In extremely low light levels the photon flux per unit area becomes so low that the scene being imaged no longer appears continuous. Instead, it is represented by individual photons which are both temporally and spatially distinct form one another. Viewed on a monitor, such an image appears as scintillating points of light, each representing a single detected photon. By accumulating these detected photons in a digital image processor over time, an image can be acquired and constructed. In contrast to conventional cameras where the signal at each image point is assigned an intensity value, in photon counting imaging the amplitude of the signal carries no significance. The objective is to simply detect the presence of a signal (photon) and to count the occurrence of the signal with respect to its position over time.

At least two types of photodetector devices, described below, can detect individual photons and generate a signal which can be analyzed by an image processor. Reduced-Noise Photodetection devices achieve sensitivity by reducing the background noise in the photon detector, as opposed to amplifying the photon signal. Noise is reduced primarily by cooling the detector array. The devices include charge coupled device (CCD) cameras referred to as "backthinned", cooled CCD cameras. In the more sensitive instruments, the cooling is achieved using, for example, liquid nitrogen, which brings the temperature of the CCD array to approximately −120° C. "Backthinned" refers to an ultra-thin backplate that reduces the path length that a photon follows to be detected, thereby increasing the quantum efficiency. A particularly sensitive backthinned cryogenic CCD camera is the "TECH 512", a series 200 camera available from Photometrics, Ltd. (Tucson, Ariz.).

"Photon amplification devices" amplify photons before they hit the detection screen. This class includes CCD cameras with intensifiers, such as microchannel intensifiers. A microchannel intensifier typically contains a metal array of channels perpendicular to and co-extensive with the detection screen of the camera. The microchannel array is placed between the sample, subject, or animal to be imaged, and the camera. Most of the photons entering the channels of the array contact a side of a channel before exiting. A voltage applied across the array results in the release of many electrons from each photon collision. The electrons from such a collision exit their channel of origin in a "shotgun" pattern, and are detected by the camera.

Even greater sensitivity can be achieved by placing intensifying microchannel arrays in series, so that electrons generated in the first stage in turn result in an amplified signal of electrons at the second stage. Increases in sensitivity, however, are achieved at the expense of spatial resolution, which decreases with each additional stage of amplification. An exemplary microchannel intensifier-based single-photon detection device is the C2400 series, available from Hamamatsu.

Image processors process signals generated by photodetector devices which count photons in order to construct an image which can be, for example, displayed on a monitor or printed on a video printer. Such image processors are typically sold as part of systems which include the sensitive photon-counting cameras described above, and accordingly, are available from the same sources. The image processors are usually connected to a personal computer, such as an IBM-compatible PC or an Apple Macintosh (Apple Computer, Cupertino, Calif.), which may or may not be included as part of a purchased imaging system. Once the images are in the form of digital files, they can be manipulated by a variety of image processing programs (such as "ADOBE PHOTOSHOP", Adobe Systems, Adobe Systems, Mt. View, Calif.) and printed.

In one embodiment, the biological sample contains protein molecules from the test subject. One preferred biological sample is a peripheral blood leukocyte sample isolated by conventional means from a subject.

The invention also encompasses kits for detecting the presence of CA IX or a CA IX-expressing cell in a biological sample. For example, the kit can comprise: a labeled compound or agent capable of detecting a cancer or tumor cell (e.g., an anti-CA IX scFv or monoclonal antibody) in a biological sample; means for determining the amount of CA IX in the sample; and means for comparing the amount of CA IX in the sample with a standard. The standard is, in some embodiments, a non-cancer cell or cell extract thereof. The compound or agent can be packaged in a suitable container. The kit can further comprise instructions for using the kit to detect cancer in a sample.

Methods of Treatment

The invention provides for both prophylactic and therapeutic methods of treating a subject at risk of (or susceptible to) a cancer, or other cell proliferation-related disease or disorder. Such diseases or disorders include but are not limited to, e.g., those diseases or disorders associated with aberrant expression of CA IX. Early symptoms of renal cancer include blood in the urine (hematuria), low back pain on one side, not associated with injury, a mass or lump in the abdomen, fatigue, weight loss that is not intentional, fever that is not associated with a cold, flu, or other infection, and swelling of ankles and legs. Diagnosis of renal cancer may be performed by computed tomography scans, magnetic resonance imaging, intravenous pyelograms, ultrasonography and angiography.

Prophylactic Methods

In one aspect, the invention provides methods for preventing cancer or a cell proliferative disease or disorder in a subject by administering to the subject a monoclonal antibody or scFv antibody of the invention or an agent identified according to the methods of the invention. For example, a scFv or monoclonal antibody may be administered in therapeutically effective amounts.

Subjects at risk for cancer or cell proliferation-related diseases or disorders include patients who have a family history of cancer or a subject exposed to a known or suspected cancer-causing agent. Administration of a prophylactic agent can occur prior to the manifestation of cancer such that the disease is prevented or, alternatively, delayed in its progression.

The appropriate agent can be determined based on screening assays described herein. Alternatively, or in addition, the agent to be administered is a scFv or monoclonal antibody that prevents or inhibits cancer that has been identified according to the methods of the invention.

Therapeutic Methods

Another aspect of the invention pertains to methods of treating a cancer or cell proliferation-related disease or disorder in a patient. In one embodiment, the method involves administering an agent (e.g., an agent identified by a screening assay described herein and/or an scFv antibody or monoclonal antibody identified according to the methods of the invention), or combination of agents that inhibit an activity of CA IX.

Combinatory Methods

The invention provides treating cancer in a patient by administering two antibodies that bind to the same epitope of the CA IX protein or, alternatively, two different epitopes of the CA IX protein. Also, the cancer is treated by administering a first antibody that binds to CA IX and a second antibody that binds to a protein other than CA IX. For example, the second antibody is Avastin, Erbitux, Humira, Xolair, Zavalin, Campath, Mylotarg, Herceptin, Remicaide, Simulect, Synagis, Zenapax, Rituxan, Panorex, ReoPro, Oncoscint, or OKT3. Additionally, the invention provides administration of an antibody that binds to the CA IX protein and an antineoplastic agent, such a small molecule, a growth factor, a cytokine or other therapeutics including biomolecules such as peptides, peptidomimetics, peptoids, polynucleotides, lipid-derived mediators, small biogenic amines, hormones, neuropeptides, and proteases. Small molecules include, but are not limited to, inorganic molecules and small organic molecules. Suitable growth factors or cytokines include an IL-2, GM-CSF, IL-12, and TNF-alpha. Small molecule libraries are known in the art. (See, Lam, Anticancer Drug Des., 12:145, 1997.)

The invention will be further described in the following examples, which do not limit the scope of the invention described in the claims.

EXAMPLES

Example 1

Construction and Characterization of a 27 Billion Member Non-Immune Human Single Chain Antibody (scFv) Phase Display Libraries Two non-immune human scFv-phage display libraries containing 12 (Mehta I) and 15 (Mehta II) billion members were constructed that are used to directly isolate a broad range of high affinity human scFvs against any target protein of interest. For details of this library and a list of the human antibodies that have been isolated from this library, please see the National Foundation for Cancer Research (NFCR) website. These scFv libraries represents two of the largest human sFv-phage display libraries ever made (Nissim, 1994; Griffiths, 1994; Vaughan, 1996; Sheets, 1998, de Haard, 1999). For the studies described herein, the Mehta I and II libraries are combined to streamline the panning and selection processes. Antibody libraries of this size are reliably be used to isolate high affinity antibodies to multiple epitopes on the target proteins. Two rounds of panning were performed against CA IX-PMPLS with 27 billion member human scFv phage display library. From each round we picked out some clones and did small scale phage rescue. With those phage scFv antibody, ELISA based on both 293T-G250 cells and parental 293 Tcells (No G250 expression) was performed. The clones which only bind to G250 positive cells were identified as "specific positive" as shown in above table and forwarded into further analysis. Results of the panning screen are provided below in Table E1.

TABLE E1

| First panning | Input | Output | Specific Positive |
| --- | --- | --- | --- |
| 1st | 5 × 1012 | 2.8 × 104 | 16/96 |
| 2nd | 8 × 1012 | 7.6 × 106 | 109/192 |

Example 2

Construction of Prokaryotic and Eukaryotic CA IX Expression Plasmids

The CA IX cDNA gene was isolated from HeLa cells using RT-PCR and then cloned it into the pcDNA3.1 expression plasmid. CA IX is expressed in three different forms for panning studies; 1) carboxy terminal C9-tagged full-length protein for incorporation into paramagnetic proteoliposomes for panning (Note: C9 is a 9 amino acid tag that corresponds to a region of human rhodopsin); 2), carboxy-terminal C9-tagged extracellular domain of CA IX for expression of secreted protein for panning; and 3), fusion protein between the extracellular domain of CA IX and Fc domain of IgG1. For epitope mapping studies, a construct was generated containing the wild-type GST-CA IX fusion protein (PG and CA extracellular domains), GST-PG domain and GST-CA domain and several GST fusion proteins with serial 5' and 3' truncations of CA.

Example 3

Isolation of High Affinity Human Anti-CA IX scFvs

Preparation of Paramagnetic Proteoliposomes Containing Properly Oriented and Functional CA IX and Panning—Paramagnetic proteoliposomes containing CA IX are prepared using recently reported procedures (Mirzabekov, 2000). A schematic diagram outlining the procedure which we have used to prepare the paramagnetic proteoliposomes is shown in FIG. 14. Briefly, tosyl-activated Dynabeads are conjugated with 1D4 Mab and streptavidin and the non-covalently bound proteins are removed by washing. The efficiency of antibody and streptavidin conjugation is checked by FACS using PE-labeled anti-mouse IgG and FITC-biotin, respectively. COS-7 cells are transiently or stably transfected with CA IX expression plasmid that has been further engineered to contain a carboxy-terminal C9 tag to which the 1D4 mAb is directed. 24 hours later, cleared lysates are obtained and are then incubated with a fixed ratio of protein/1D4-streptavidin-coated beads on a rocking platform. As a final step, after washing the beads are then mixed with solubilized lipids containing biotynil-DOPE, that self-assemble around the beads producing the lipid bilayer. The inventors have previously obtained three highly purified proteolipsomes containing human CCR5, human CXCR4 and EBV LMP1 that are devoid of other cellular proteins. The orientation of CA IX in each batch of CA IX-proteoliposomes is routinely confirmed by FACS analysis using several well characterized M75 murine Mab against the EC domain and a commercially available anti-CA IX Mab (Novus-Biologicals (NB 100-417).

The CA IX proteoliposomes are used to select recombinant antibodies. Briefly, after the final panning, as determined by fold enrichment in titers during each round of selection, a minimum of 200 individual colonies (2 mictotiter plates) is infected with helper phage, and phage containing supernatants are screened using a cell based ELISA with stably transfected Cf2-CA IX+ cells (e.g., using a Tecan liquid handling robot so that thousands of colonies are evaluated). HRP-coupled rabbit anti-M13 phage is used for this purpose. Positive clones are rescreened for specificity by using Cf2 parental cell lines and several cell lines that do not express CA IX. Initial screenings are made as stringent as possible by lowering the number of cells used to coat the ELISA plate as well as using different RCC cell lines that express different amounts of surface CA IX (e.g. SK-RC-52 (high expression); SK-RC-09 (low expression) or normal kidney cell lines (no expression)) (Ebert, 1990; Liu, 2002). Only phage that bind specifically to CA IX with values >5× background are further evaluated. DNA sequence analysis is performed using a dedicated Perkin Elmer 310 Sequencer. Unique clones are entered into our scFv immunoglobulin gene database.

Example 4

Panning on Immunotube Coated Plates

Conventional panning procedures are used to isolate a panel of anti-CA IX scFvs by coating the purified recombinant CA IX C9 tagged protein (EC domain) on immunotubes. The second procedure is used to decease any epitope bias that may take place with the proteoliposome panning. Generally, the scFvs isolated from the two techniques are never the same.

Example 5

Epitope Mapping of Anti-CA IX scFvs

Studies with GST-CA IX fusion proteins. Epitope mapping studies are performed with GST-CA IX fusion proteins that are described herein. These studies are performed by coating ELISA plates with GST (control), GST-CA IX (wt), GST-CA IX (PG) or GST-CA truncation fusion proteins on the plate and then performing a phage ELISA that detects phage antibody binding by HRP-labelled rabbit anti-M13 antibody.

Studies with CA IX point and deletion mutants—For other epitope mapping and binding affinity determination studies, the anti-CA IX scFvs are evaluated as highly purified soluble proteins that are produced in *E. coli* as scFv-His6-c-myc fusion proteins. Constructed are a series of deletion and alanine scanning mutations to the EC domain of C-terminal C9-tagged CA IX used to evaluate antibody binding through Co-IP/Western blot studies. Briefly, eukaryotic expression plasmids for wt and mutant CA IX are transfected into 293T cells and the cell lysates are mixed with the purified anti-CA IX scFvs and either IP'd with anti-C9 coated sepharose beads (to assess CA IX expression levels) or with anti-c-myc sepharose (to assess co-IP with antibody) (see Sui, 2004). All of the anti-CA IX scFvs are tested for their ability to bind wt CA IX by Western blotting under reducing, non-reducing conditions and after PNGase F treatment to determine if the scFvs recognize linear or conformational epitopes or are sensitive to carbohydrate removal, respectively (Sui, 2004). The ability of the anti-CA IX scFvs to compete with WX-G250 and M75 by FACS analysis is also evaluated.

Studies that examine cross-competition among different anti-CA IX scFvs. The mapping studies include cross-competition studies using the different scFvs to determine if anti-CA IX scFvs that map to similar regions of CA IX are binding to the same epitope. For these studies, two different approaches are used. In one approach the purified scFv proteins are biotinylated using standard techniques. In FACS assays, competitive binding (blocking) assays are used to determine the ability of anti-CA IX scFvs to block the binding of any other biotinylated scFvs, the later detected using streptavidin-FITC. In the second approach, real-time Biacore analysis is used to perform multi-determinant binding experiments. In these studies, when the first scFv is saturably bound to the CA IX EC domain bound to the biosensor chip, a second scFv is added. If additional binding of the second scFv is detected, the epitopes are not overlapping. However, if additional binding of the second scFv is not detected, it can be assumed that either steric hindrance or overlapping binding sites are responsible for the lack of binding of the second scFv.

Example 6

Inhibition of Carbonic Anhydrase Activity Among Different Anti-CA IX scFvs

Anti-CA IX scFvs that are epitope mapped to the CA domain are able to block enzymatic activity. This is an important anti-tumor biological property of the antibodies that is distinct from their retargeting capacity. To evaluate the ability of anti-CA IX scFvs to block carbonic anhydrase activity, an assay is established to measure carbonic anhydrase activity of the CA IX paramagnetic proteoliposomes using established methods (Brion, 1988; Dodgson, 1991). In brief, the velocity of the reaction $CO_2+H_2O \leftrightarrow H_2CO_3$ is measured by the time required for acidification of carbonate buffer in $CO_2$ atmosphere, detected with phenol read as a pH indicator (Zavada, 1997). The reaction proceeds even in absence of the enzyme, with $t_o$=control time (this is set at 60 sec). Carbonic anhydrase reduces the time of acidification to t; one unit of the enzyme activity reduces the time to one half of control time: $t/t_o$=1. The CA IX paramagnetic proteoliposomes will be washed in PBS, resuspended in 1 mM carbonic buffer, pH 8.0. Acetazolamide (Sigma) serves as a positive control for inhibition of CA activity. Thus it is demonstrated that a purified anti-CA IX scFvs, in a dose dependent manner, blocks the CA activity of the proteoliposomes.

Example 7

Affinity Measurements

Cell binding studies—Saturation binding studies on Cf2-CA IX+ cells are performed on each of the purified anti-CA IX scFvs. The approximate affinity of each scFv for CA IX is measured by serially diluting each purified anti-CA IX scFv prior to staining Cf2-CA IX+ cells. Cells are incubated with various concentrations of highly purified sFvs, washed, incubated with anti-c-myc, washed and then treated with FITC anti-mouse IgG. After final washing, cells are fixed and analyzed by FACS. To account for variations in day-to-day staining and flow cytometer calibration, the $EC_{50}$ values for each scFv (defined as the concentration of scFv which gives half-maximal MCF value) is normalized to that observed with WX-G250 in each experiment. Also examined is the ability of the scFvs to bind to other CA IX expressing RCC cell lines that express different levels and/or conformations of CA IX.

BiaCore studies—The equilibrium dissociation constants ($K_D$) of the anti-CA IX scFvs are determined by surface plasmon resonance in a BIACORE 1000 instrument. The optimal conditions for immobilizing the CA IX EC domain to the biosensor chip is pre-determined. Association rates are measured using a constant flow of 5 ul/min and a scFv concentrations ranging from $5\times10^{-6}$ to $1\times10^{-9}$ M. $k_{on}$ is determined from a plot of ln (dR/dt)/t vs concentration (Karlsson, 1991). Dissociation rates are measured using a constant flow of 25 ul/min and a sFv concentration of $1.0\times10^{-6}$ M. $k_{off}$ is determined during the first 30 seconds of dissociation, $K_D$ is calculated as $K_{off}/K_{on}$. The binding constants of the monovalent scFvs are generally markedly improved when the binding sites are made bivalent due to an avidity effect. Therefore, cell binding and Biacore studies are performed on the bivalent scFv-Fc fusion proteins described herein.

Example 8

Antibody Induced CA IX Internalization

Anti-CA IX mediated internalization visualized by confocal microscopy. Crosslinking of membrane proteins is often a requirement for their internalization. Therefore the monovalent scFvs are converted to bivalent scFv-IgG1 fusion proteins. Constructed are eukaryotic expression vectors that contain Sfi1/Not1 cloning sites that allow the scFvs identified from the phage display vector to be directly cloned in frame between a human VH leader sequence and Fc of human IgG1. This results in the expression and secretion of bivalent scFv-IgG1 fusion proteins that is readily purified by protein A Sepharose. For these studies, each anti-CA IX scFv is cloned into the scFv-Fc expression plasmid, transiently transfected into 293T cells and the secreted scFv-Fc fusion proteins are purified by protein A sepharose. The fusion proteins are directly labeled with FITC and their binding to RCC cell lines SK-RC-52 (high CA IX expression); SK-RC-09 (low CA IX expression) or normal kidney cell lines (no expression)) are evaluated by con-focal microscopy. Cells are incubated with saturating amounts of FITC-anti-CA IX scFv-Fc at 4° C. or 37° C. for 60 minutes and then the cells are directly visualized for evidence of a change in staining from diffuse surface staining to one of capping and punctate staining of endocytic vesicles. Confocal images are recorded using an ACAS Ultima confocal microscope (Meridian Instruments, Inc.) with images representing 1-μm sections through the center of a focal plane using a 100× oil immersion objective (Carnahan, 2003).

Example 9

Quantitation of CA IX Expression and Kinetics of Antibody-Mediated CA IX Internalization for RCC Cell Lines Cell surface expression of CA IX is quantitated using anti-CA IX scFv-Fc antibodies monvalently labeled with PE (conjugated by BD Biosources). One microgram of each scFv-Fc protein is generally added to cells with the appropriate isotype controls for 30 min at 4° C. in the dark. Following washing and resuspension in FACS Lysing Solution (BD Biosciences), the cells are immediately analyzed by flow cytometry (BD FACSCalibur) The CA IX receptor numbers (determined by the binding of at least three different scFv-Fc proteins) are calculated by comparison to the standard fluorescence curve set by the QuantBRITE PE fluorescence quantitation kit (BD Biosciences) (Carnahan, 2003).

The cross-competition experiments described herein is a useful tool to quantitate antibody mediated internalization of CA IX. It is shown by FACS that adding increasing concentrations of one anti-CA IX scFv-Fc protein does not compete for binding of a different PE-labelled anti-CA IX scFv-Fc protein under investigation. This provides a means of independently measuring cell surface CA IX and internalization. To quantitate cell surface CA IX, SK-RC-52 or SK-RC-09 cells are incubated with increasing concentrations of unlabeled anti-CA IX scFv-Fc protein (range 0.01 to 100 μg/ml/ $10^6$ cells) for one hour at 37° C. Cells are then washed with cold PBS and immediately analyzed by FACS for CA IX quantitation by addition of non-cross-competing PE-labelled anti-CA IX scFv-Fc protein. The resulting surface density of CA IX is measured by comparing QuantiBRITE beads and PE-anti-CA IX scFv-Fc and are calculated as a percentage of total CA IX on untreated cells (100%). The schemata are carried out for each anti-CA IX scFv-Fc for which non-cross reactive antibodies have been identified. The kinetics of internalization are investigated by incubating saturating amounts of unlabeled scFv-Fc for varying times prior to addition of PE-labelled anti-CA IX scFv-Fc protein.

Example 10

Quantitation of CA IX Expression and Kinetics of Antibody-Mediated CA IX Internalization for Primary RCC Cells To determine if these observations can be extended to "fresh" renal cell carcinoma cells, tumor tissue is obtained from human subjects who have consented to participate in DFHCC protocol 01-130: *Collection of specimen in renal cell* carcinoma. A pathologist determines that adequate material has been reserved for clinical diagnosis. Remaining tissue is made available for research studies. A fragment of fresh tumor tissue is collected into a sterile 50 cc conical tube containing tissue culture media. The specimen is delivered fresh on wet ice. The following protocol has been optimized by the cytogenetics laboratory within the Pathology Department at Brigham & Women's Hospital. Cultures of primary renal tumors are routinely grown for clinical cytogenetics using this protocol. Cultures that have been successfully established are generally maintained for eight passages or more using these methods. Specifically, non-malignant tissue is trimmed away from the specimen. The tumor is minced using sterile instruments. 4.5 mls of media are mixed with 0.5 ml of collagenase (Collagenase Type 1A (Sigma # C-9891)) solution. The specimen is incubated in collagenase for 48 hours at 37° C. The sample is vigorously triturated to further disaggregate and transferred to a 15 cc tube. The sample is centrifuged at 1000 RPM for 10 minutes, and the cell pellet resuspended in complete media (CM) Cells are plated in complete media (CM) [DMEM medium supplemented with HEPES-buffer (10 mM), sodium pyruvate (1 mM), 20% (v/v) heat-inactivated FBS and penicillin (50 IU/ml)/streptomycin (50 µg/ml) onto tissue culture dishes or flasks. Cultures are grown in a tissue culture incubator at 37° C. with 10% humidified $CO_2$. Cultures are passaged and expanded when subconfluent. Aliquots are frozen in standard 90% FCS/10% DMSO freezing media after a few passages so that a bank of matched cells are available for future experiments. Quantitation of CA IX expression and kinetics of antibody-mediated CA IX internalization are determined for freshly prepared cells in the same manner as for the RCC cell lines.

Example 11

Evaluation of the Ability of Human T-Lymphocytes Transduced with Lentiviral Vectors Encoding a Panel of Anti-CA IX Chimeric Immune Receptors to Kill CA IX Expressing RCC Cells In Vitro and In Vivo in SCID-Beige Mice Bearing RCC Xenografts Lentiviral vectors have a distinct advantage over traditional retroviral vectors derived from oncogenic retroviruses (e.g. MMLV) in that they are able to efficiently transduce non-replicating cells. In addition, the VSV-G pseudotyped vectors can be concentrated to high levels (circa $10^9$ infectious particles/ml) and by doing so high levels of transduction of human peripheral blood T-lymphocytes are achieved. High level expansions of these transduced cells are readily achieved. This provides a method to simultaneously evaluate a number of different chimeric receptors directed against CA IX using single donor PBLs for transduction.

Figure 9:
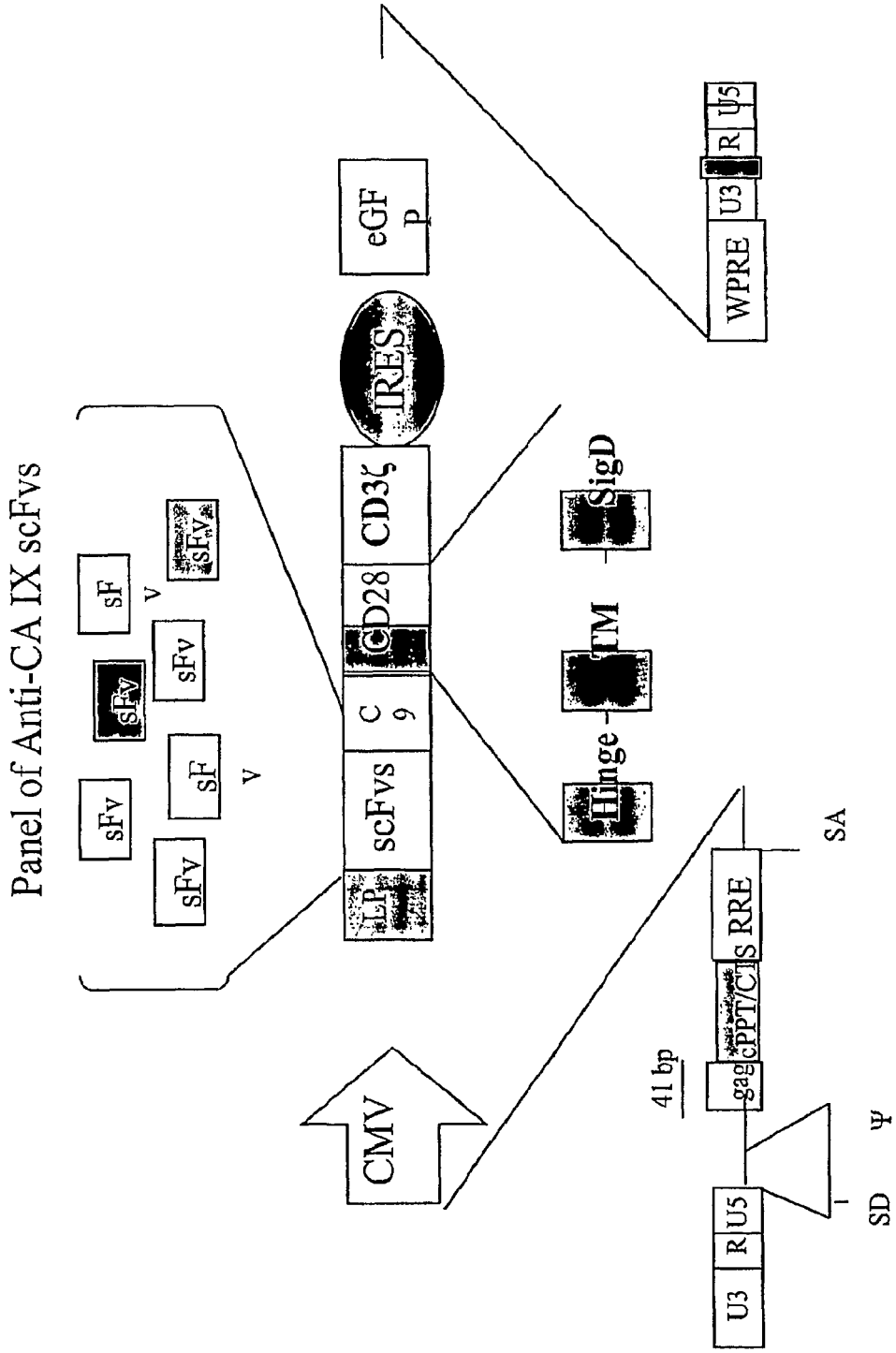
FIG. 9 is a schematic illustration showing a SIN lentiviral construct for screening anti-CA IX scFvs.
Figure 10:
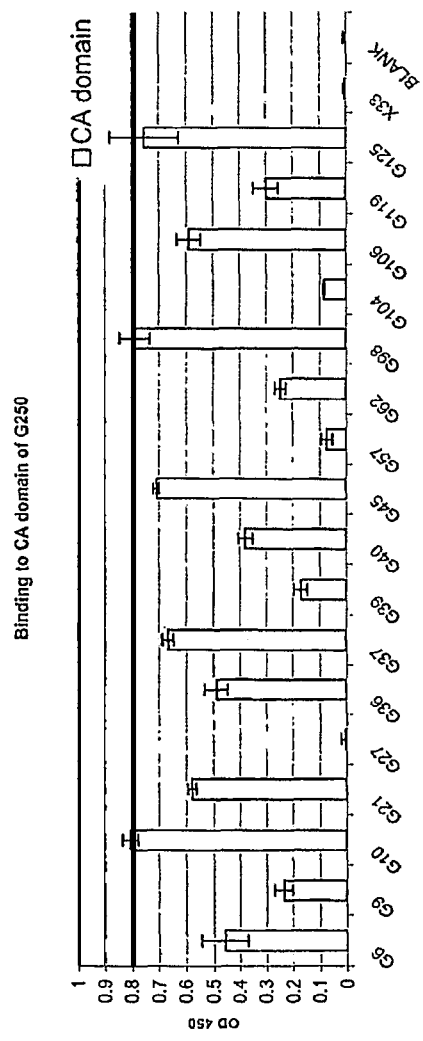
FIG. 10 is a bar graph showing epitope mapping results demonstrating the binding of various scFv antibodies to the CA domain of the CA IX protein.
Figure 11:
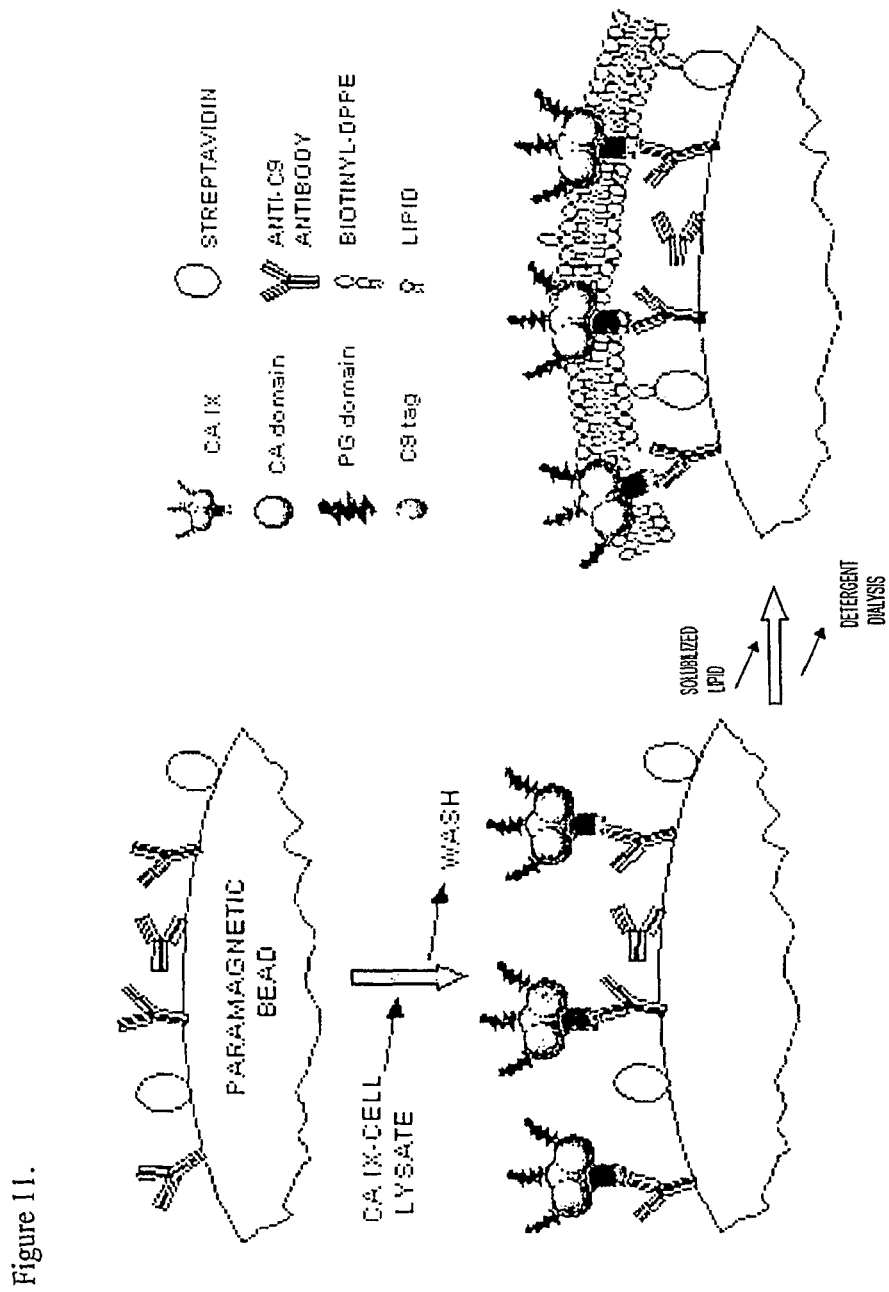
FIG. 11 is a schematic illustration of the construction of paramagnetic proteoliposomes (PMPLs) containing CA IX (G250).
Figure 12:
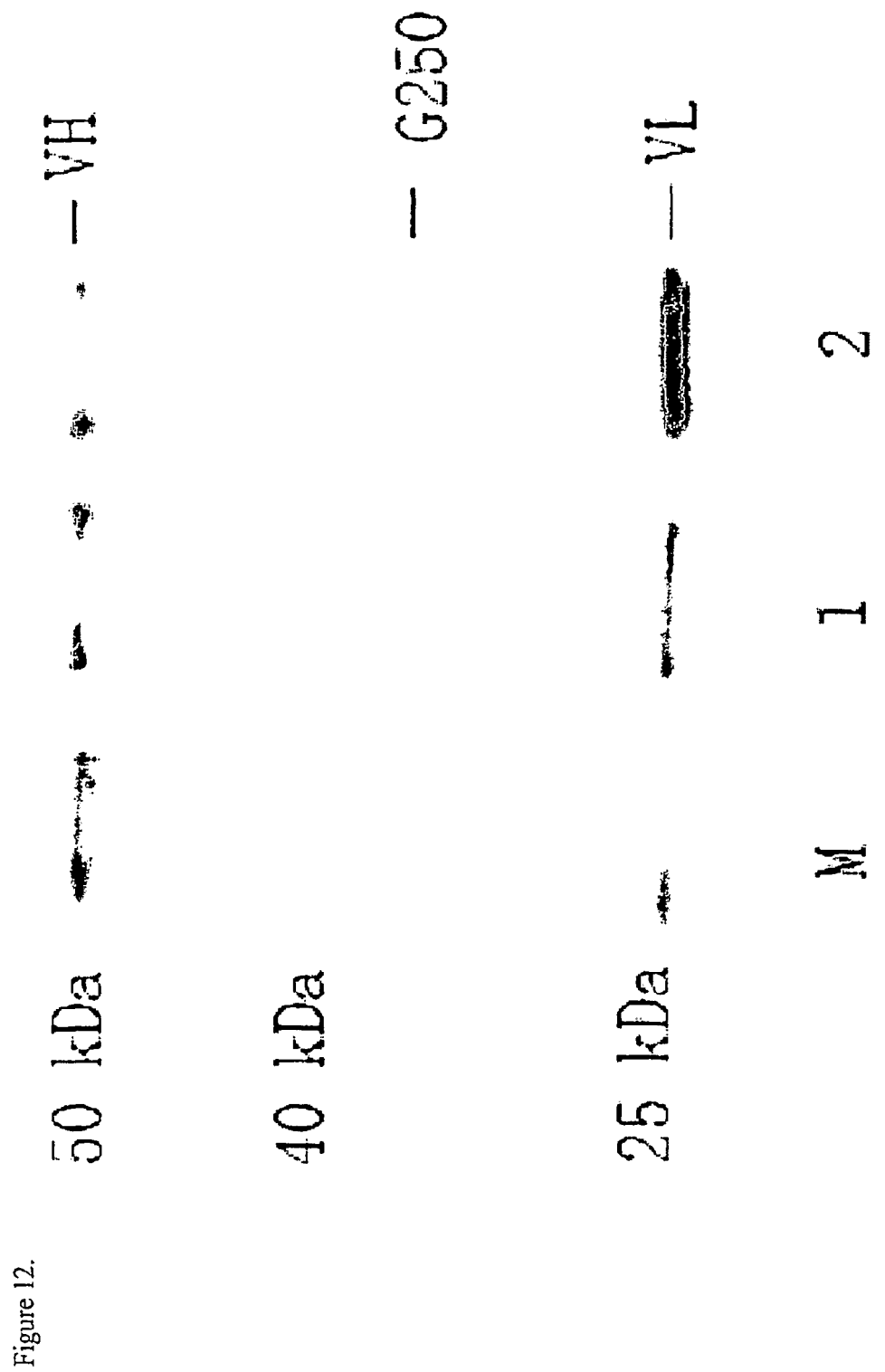
FIG. 12 is a photograph of a stained 12% SDS PAGE gel showing electrophoresed G250 PMPLs.

Design of Lentiviral Vectors. Previously constructed and characterized are lentiviral vectors that are engineered with bicistronic expression cassettes in which the first gene of interest (e.g. chimeric immune receptor) is under the control on an internal CMV promoter and the second gene (eGFP or other) is expressed from an internal ribosomal entry site (EMCV). This configuration reliably leads to uniform expression of both genes of interest (Ogueta, 2001; Zhu, 2004). Self-inactivating lentiviral vectors are used in these studies. The lentiviral vectors encode different anti-CA IX chimeric immune receptors and are transfected into 293T cells, along with a packaging vector and VSV-G envelope for production of virus particles (see Queta, 2002 and Zhu, 2004). The viral supernatants are harvested, the virus particles are then concentrated by ultracentrifugation and titers are determined by FACS analysis of eGFP expression on freshly transduced 293T cells and PBMCs. Highly enriched transduced T-cells are readily selected for eGFP (or surface C9) expression by FACS sorting (see FIG. 5). As shown in FIG. 9, a C9 tag sequence is introduced to quantitate chimeric receptor expression levels in the transduced cells.

Isolation and transduction of human peripheral blood T-lymphocytes. All blood samples are obtained either as buffy coat cells (isolated from leukopacs (a leukophoresis product) through the Kraft Blood Bank at DFCI from anonymous donors) or from healthy volunteers after giving written informed consent under an institutional review board-approved protocol. PBLs are generally isolated by low-density centrifugation on Lymphoprep (Accurate Chemical and Scientific Corporation). For retroviral transduction, T cells are activated overnight with 2 ug/ml phytohemagglutinin (Murex Diagnostics) and transduced in 6-well non-tissue culture plates (Falcon) coated with 15 µg/ml of retronectin (Takara Biomedicals) as per the manufacturer's instructions, with fresh viral supernatants daily at MOL 25 for 3 days by spinulation at 80 g at RT for 1 hr. The density of surface chimeric receptor expression is examined by FACS analysis with PE-labeled 1D4 Mab (anti-C9 tag) and by Western blotting of cell lysates.

Design of Artificial Antigen Presenting Cells (AAPCs) and expansion of transduced T-lymphocytes. To generate sufficient quantities of chimeric receptor expressing T-lymphocytes for in vivo studies, AAPCs are constructed by retroviral transduction of NIH-3T3 mouse fibroblasts with CA IX and the co-stimulatory molecule CD80 (137.1) molecule (3T3 ((CA IX+CD80+)). When the chimeric receptor expressing T-cells are incubated with AAPCs in the presence of IL-15, synergistically enhanced selective expansion of the transduced cells is expected (Brentjens, 2003). Specifically, for ex vivo expansion, transduced T-lymphocytes are co-cultured in 6-well tissue culture plates (Falcon) with 80% confluent AAPSs in medium supplemented with 20 U/ml IL-2 and 10 ng/ml IL-15. Expansion of the transduced cells within the population of cells is measured by the progressive rise in percentage of cells expressing eGFP during the culture period. In some studies, IL-2 production and fold-expansion of the transduced T-lymphocytes in the presence of unmodified NIH3T3 cells or AAPCs are measured. Three days after lentivral transduction, the transduced cells are plated at 106 PBLs/ml on the specified NIH3T3 monolayers. Supernatants are harvested after 24, 48 and 72 hrs and assayed for IL-2 content by ELISA.

Cytotoxicity assays. The cytotoxic activity of transduced T-lymphocytes is determined by standard $^{51}$Cr-release assays using RCC cell lines SK-RC-52 (high CA IX expression); SK-RC-09 (low CA IX expression) and normal kidney cell lines (no CAIX expression) as target cells. Effector cell number in all assays are calculated on the total number of transduced T-lymphocytes (calculated by eGFP or C9 surface expression). Effector to target cell ratios are varied from 25:1 to 0.7:1. In some cases (primary RCC cells), CTL assays are performed using a nonradioactive cytotoxicity detection kit (lactate dehydrogenase (LDH); Roche Diagnostics).

Example 12

Determination of Cytotoxicity of Anti-CA IX Antibodies In Vivo

An RCC tumor model is established to test the killing capacity of the chimeric receptor expressing T-lymphocytes to kill RCC tumor cells in vivo.

SCID-Beige mouse model of RCC—SCID-Beige mice (in groups of 5 mice) are inoculated with 5×10⁶ RCC positive and RCC negative tumor cell lines on each flank. One week later, transduced T-lymphocytes (10×10⁶ cells or 50×10⁶ cells) are injected by tail vein. In some animals, infusion of IL-2 (Alzet pump) are used to augment in vivo cell activation at a rate of 5×10⁵ units/hr over 7 days. The tumor bearing mice are examined daily for signs of distress and tumor size are recorded with calipers. Two to three different chimeric receptors are evaluated in vivo. Mock transduced T-lymphocytes and T-lymphocytes transduced to express an irrelevant chimeric receptor serve as controls.

After the in vivo specificity of the anti-tumor effects are documented (no effects on CA IX negative tumor cell growth) the experiments are repeated with only the CA IX+ RCC tumor cell inoculations. Mock transduced T-lymphocytes and T-lymphocytes transduced to express an irrelevant chimeric receptor serve as controls. Survival curves are examined for each group of mice. In separate tumor bearing mice, multiple weekly injections (up to three) of transduced cells are given. Statistical analysis of survival data log-rank analysis are performed using GB-STAT softward (Dynamics Microsystems). Kaplan-Meier survival curves are plotted for all groups of mice.

Contribution of CD4+ and CD8+ Transduced T-Lymphocytes to In Vivo Tumor Cell Killing.

The role of CD4+ and CD8+ T-lymphocytes in tumor eradication is analyzed by treating the RCC-bearing mice with highly purified CD4+ and CD8+ T-lymphocytes, or a 1:1 mixture of both. Survival curves are compared to mice inoculated with unfractionated transduced T-lymphocytes.

Survival of chimeric receptor expressing T-lymphocytes in vivo and tumor histochemical staining. To determine the circulating half-life of the transduced cells in vivo, mice are bled by tail vein at defined times and the cells are analyzed for chimeric receptor expression by FACS analysis. The number of cells and the density of the receptors as a function of time are quantitated after infusion into the tumor-bearing (and as controls non-tumor bearing) mice. Some mice showing tumor regression are sacrificed and the tumor tissue are examined by immunohistochemical staining for the presence of transduced cells

Example 14

Analysis of Transduced Chimeric Receptor Expressing T-Lymphocytes from RCC Patients for the Ability to Lyse Autologous Tumor Cells It is recognized that long-term passage of cell lines in some circumstances leads to genomic and gene expression changes that alter their behavior as CTL targets. Primary RCC cells are used. Alternatively, passaged immortal RCC cell lines are used. In some embodiments, the primary RCC provide a target that most closely resembles what T-lymphocytes generally encounter in vivo. Primary human RCC cells maintained in short term culture have been used successfully as targets of autologous CTLs (Liu, 1998; Kawai, 2003). Chimeric immune receptors recognize antigens in a non-MHC-restricted manner so MHC-compatible tumor and T cells are not necessary. However, peripheral blood are collected from subjects donating tumor tissue so that autologous lentiviral vector transduced T-lymphocytes are derived.

Transduction of RCC patient PBLs. Peripheral blood is generally obtained under standard protocols. Generally, cells are activated and transduced and optionally expanded as herein. Non-transduced and cells transduced with an irrelevant chimeric receptor serve as controls since it is possible that some degree of tumor cell killing are seen from endogenously primed cytotoxic T-lymphocytes. Quantitation of the percentage of transduced cells at the end of transduction and beginning of the cytoxicity assay are performed by FACS. Also quantitated is the density of chimeric receptors expressed on the transduced T-lymphocytes. Cells may be transduced once or a plurality of times (e.g., two, three, four, five or more times). One skilled in the art will recognize that in certain cases the level of chimeric receptor expression may be critical for cell killing. Therefore, the invention provides alternative promoters that increase expression on transduced T-lymphocytes. The design of the lentiviral vector system is flexible in the unique restriction sites flank the internal CMV promoter so that different promoters can be easily interchanged (e.g., SRα, EF1α, MMLV). Also, stable expression of a co-stimulator molecule (e.g. CD80 (B7.1)) is optionally introduced.

Cytotoxicity assay with autologous tumor cells. The surface density CA IX on the autologous RCC cells are quantitated by FACS analysis as described herein. For the cytotoxicity assay, varying effector to tumor cell ratios are tested and $^{51}$Cr or LDH release are quantitated after a 4 hr incubation.

Examination of tumor cell killing by transduced T-lymphocytes. Visualization of cell killing in metastases is visualized with positron emission tomography. For example, in an RCC mouse model a MicroPET imaging system (Concorde Microsystems) is used. Generally, the mouse is injected with about 200 µCi of $^{18}$F-fluorodeoxyglucose (FDG) injected intravenously, and imaged.

Example 15

Analysis of Human Renal Cell Carcinomas

Human Peripheral Blood. Buffy coat cells obtained from leukopacs (a leukophoresis product) are obtained through the Kraft Blood Bank at DFCI from anonymous donors. Alternatively, human peripheral blood mononuclear cells from healthy volunteers are used.

Acquisition of primary human tumor specimens. Tumor tissues are obtained from human subjects who have consented to participate in DFHCC protocol 01-130. pathologist will determine that adequate material has been reserved for clinical diagnosis. A fragment of fresh tumor tissue is collected into a sterile 50 cc conical tube containing tissue culture media. The specimen is delivered fresh on wet ice to the research laboratory. Peripheral blood is also obtained from these patients. RCC tissue and blood is obtained from male and female subjects, and from a plurality of subjects representing diverse ethnicities.

Example 16

Non-Human Vertebrate Animals

SCID-Beige mouse model. 8 to 12-week old Fox Chase C.B.-17 (SCID-Beige) mice (Tanconic, Germantown, N.Y.) are inoculated with tumor cells via subcutaneous injection. Tumor cells (5×10⁶) are collected and loaded into a needle (22-25 g) and injected subcutaneously above the hind flank regions creating a measurable induration. No suture is required. No anesthesia is considered necessary. After 7 days, transduced cells (1-5×10) are then injected by tail vein mixed in saline to a volume not exceeding 200 ul. All mouse studies are carried out under approved protocols. Administration of agents is accomplished by the use of subcutaneous pumps.

Pumps implanted subcutaneously are placed between the scapulae to minimize effect on mobility.

Example 17

Generation of Whole Human IgG1s: Fusion Proteins Containing Anti-Ca Ix Antibodies or scFvs and Immunoglobulin Domains Introduction of the anti-G250 scFv antibody G10 into TCAE6-LL2 whole IgG1 expression vector was performed as follows. Primers used were

```
G10 VH 5':  ATC GAC GCG TGC CTG AGC GAG GTG CAG CTG GTG CAG TC;  (SEQ ID NO: 47)

G10 VH 3':  CAA TGG TCA CCG TCT CTT CAG CTA GCA CCA GG;           (SEQ ID NO: 48)

G10 VL5':   ATC CCA AGC TTA AGC CAG TCT GTG CTG ACT CAG CC;       (SEQ ID NO: 49)

G10 VL3':   GGA GGG ACC AAA TTG ACC GTC CTA GGT CAG C.            (SEQ ID NO: 50)
```

VH and VL fragments of G 10 were amplified by PCR with these primers and G 10 scFv plasmid was used as template. The VH and VL PCR products were digested by Mlle/NheI and HindIII/AvrII, respectively, and inserted into corresponding sites of full length human IgG1 expression vector. After transformation and plasmid Maxi prep, sequence analysis was performed to confirm that this clone is completed correctly. These methods are also described in Sui et al., PNAS 101(8): 2536-41 (2004), the contents of which are incorporated by reference in their entirety.

Introduction of the anti-G250 scFv antibody G36 into TCAE6-LL2 whole IgG1 expression vector was performed as described above with the following primers.

```
G36 VH 5':  TAG GGC ACG CGT GTG CTG AGC GAG GTG CAG CTG GTG CAG TC  (SEQ ID NO: 51)

G36 VH 3':  TCT AGT GCT AGC TGA AGA GAC GGT GAC CAT TG               (SEQ ID NO: 52)

G36 VL5':   CTA GCA AGC TTA TCC CAG TCT GTG CTG ACT CAG CC           (SEQ ID NO: 53)

G36 VL3':   ATA GCA CCT AGG ACG GTC AGC TTG GT                       (SEQ ID NO: 54)
```

Example 18

Cross Competition of Anti-G250-Fcs for G250 Antigen Binding

Cross competition of anti-G250-Fcs for G250 Antigen binding was performed as follows:

Anti-G250-Fc antibody was labeled with Biotin (hot proteins) according to manufacturers instruction. 96 well microplates were coated with G250-Fc fusion proteins at 4° C. overnight, 50 µl of biotin-anti-G250-Fcs was added with/without cold anti-G250-Fcs at 5 µg/ml in PBS, and incubate at room temperature for 1 hr wash out unbound antibodies and add HRP-strepdavidin. Plates were developed and OD450 determined Calculate %=100*(OD450 of hot protein plus cold protein)/(OD450 of hot protein plus PBS)

Example 19

Inhibition of Carbonic Anhydrase Activity by CA IX Specific scFv-Fc Antibodies Inhibition of carbonic anhydrase activity by carbonic anhydrase specific scFv-Fc antibodies was determined as follows:

Material and Method:

The electrometric method to test the Carbonic Anhydrase (CA) activity in which the time required (in seconds) for a saturated CO2 solution to lower the pH of 0.012 M Tris HCl buffer from 8.3 to 6.3 at 0° C. is determined.

Blank Determination: Add 6.0 ml of chilled 0.02 M Tris HCl buffer, pH 8.0 to a 50 ml Falcon tube. Maintain temperature at 0-4° C. and record pH. Add 4 ml of chilled CO2 saturated water to Tris buffer and immediately start a stopwatch to record the time required for the pH to drop from 8.3 to 6.3. Record this time as $T_0$.

Enzyme Determination: Add 6.0 ml of chilled 0.02 M Tris HCl buffer, pH 8.0 to a 50 ml Falcon tube. Maintain temperature at 0-4° C. and record pH. Add 1 µg of Carbonic Anhydrase IX (CA IX), namely G250 (in the version of extracellular domain of G250 fused to human IgG1 Fc domain, G250-ECD-Fc) in 100 µl of PBS. Quickly add 4 ml of $CO_2$ saturated water and record the time required for the pH to drop from 8.3 to 6.3. Record this time as T. Calculate the Unit activity of Carbonic Anhydrase as the following formulation: Units/mg=$2\times(T_0-T)/(T\times mg$ enzyme in reaction mixture).

Inhibition Function of anti-G250 scFv-Fc Antibodies Determination: Mix anti-G250 scFv-Fc antibodies with 1 µg of G250-ECD-Fc at the molar ratio of Abs:Enzyme=1:1, 5:1 or 25:1 and incubated the mixture at room temperature for 50 minutes. Add 6.0 ml of chilled 0.02 M Tris HCl buffer, pH 8.0 to a 50 ml Falcon tube. Maintain the temperature at 0-4° C. and record pH. Add the mixture of antibody and G250-ECD-Fc, 4 ml of CO2 saturated water and record the time required for the pH to drop from 8.3 to 6.3. Record this time as $T_{Ab}$. Carbonic anhydrase small molecular inhibitor acetazolamide (Sigma) and anti-CXCR4 scFv-Fc antibody X33 are used as positive and negative control at the same molar ratio, respectively. Calculate the Units activity of Carbonic Anhydrase treated by scFv-Fc antibodies as the following formulation: Units$_{Ab}$/mg=$2\times(T_0-T_{Ab})/(T_{Ab}\times mg$ enzyme in reaction mixture). Calculate the percentage of Inhibition as the following formulation: % of Inhibition=$100\times(1-$Units$_{Ab}$/mg/Units/mg).

Figure 24:
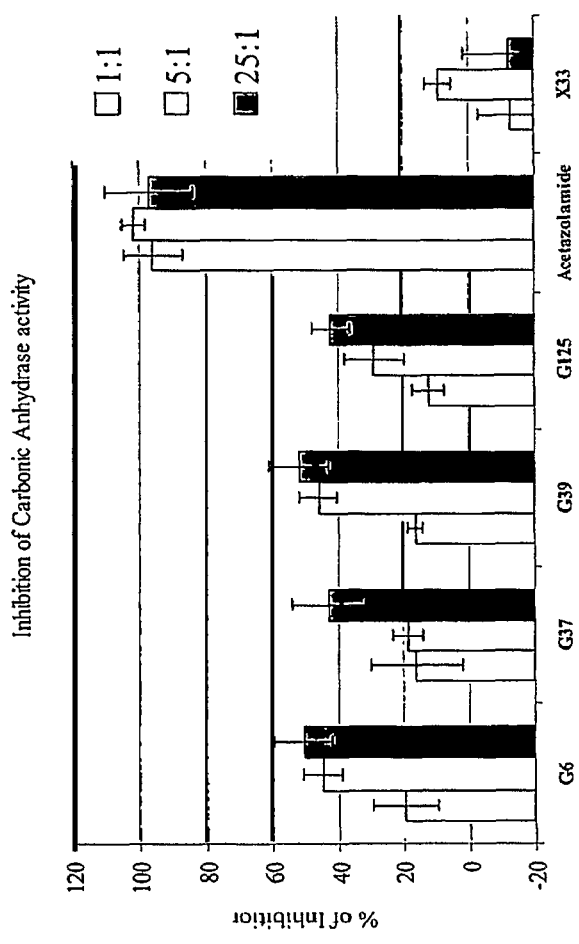
FIG. 24 is a bar chart showing inhibition of carbonic anhydrase activity with carbonic anhydrase scFV-Fc specific antibodies.
Figure 25:
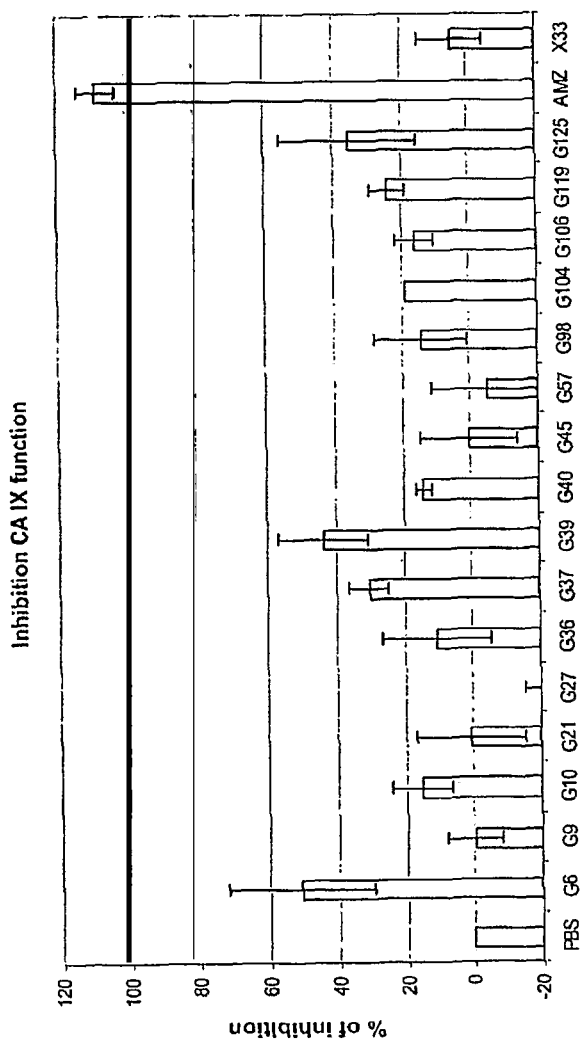
FIG. 25 is a bar chart showing inhibition of carbonic anhydrase activity with carbonic anhydrase scFV-Fc specific antibodies.
Figure 27:
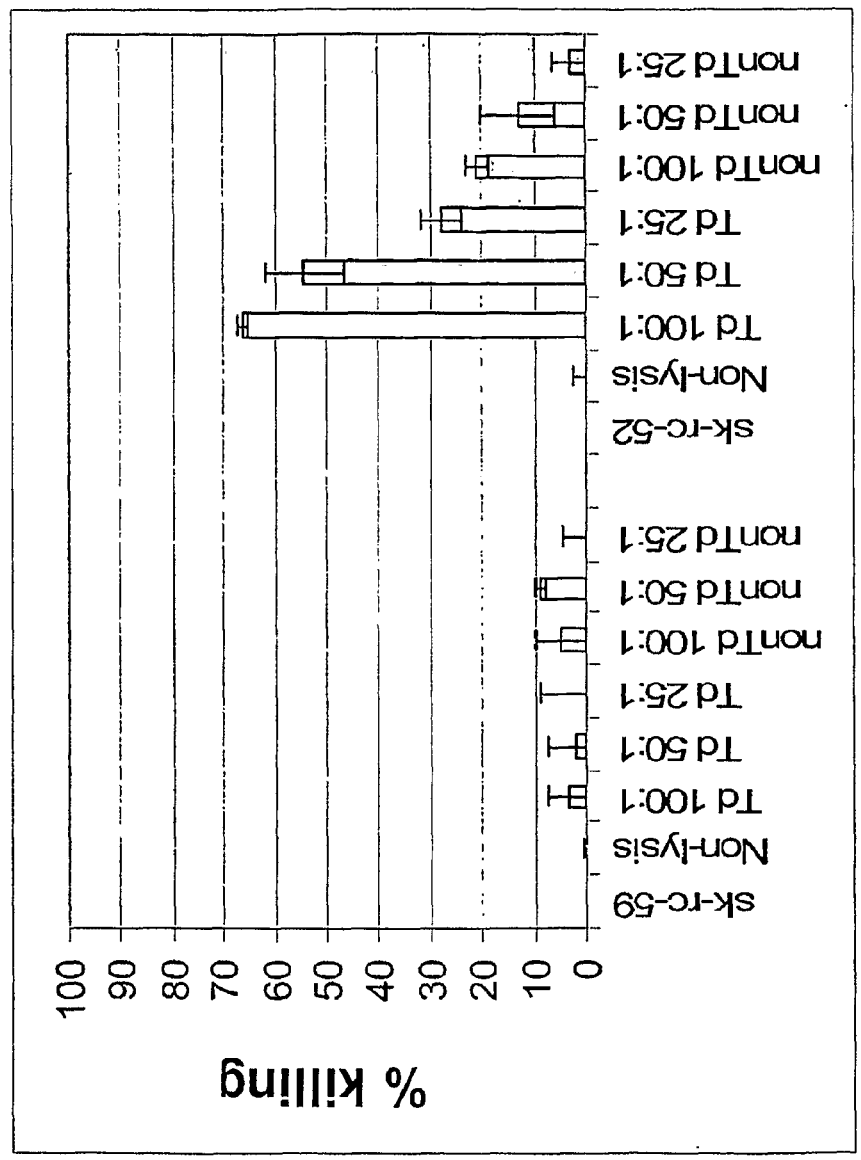
FIG. 27 is a bar chart showing the results of a Cytotoxicity assay using G36 scFv-chimeric T cell receptor transduced T cells. Cytotoxicity was preformed by incubating control non-transduced human T-cells (nonTd) or G36 anti-CA IX (G250) chimeric receptor transduced T cells (Td) with CAIX negative cells (Left panel—SK-RC-59) or CAIX positive cells (right panel—SK-RC-52 cells) at different effector to target cell ratios. As can be seen, these is highly efficient killing of the CAIX+ SK-RC-52 cells by transduced G36 anti-CA IX chimeric receptor expressing cells very poor killing of SK-RC-59 cells that do not express CAIX. Also as seen on the right panel, although there is some non-specific killing of the SK-RC-52 cells by non-transduced cells, the killing is much higher by the transduced cells.
Figure 28:
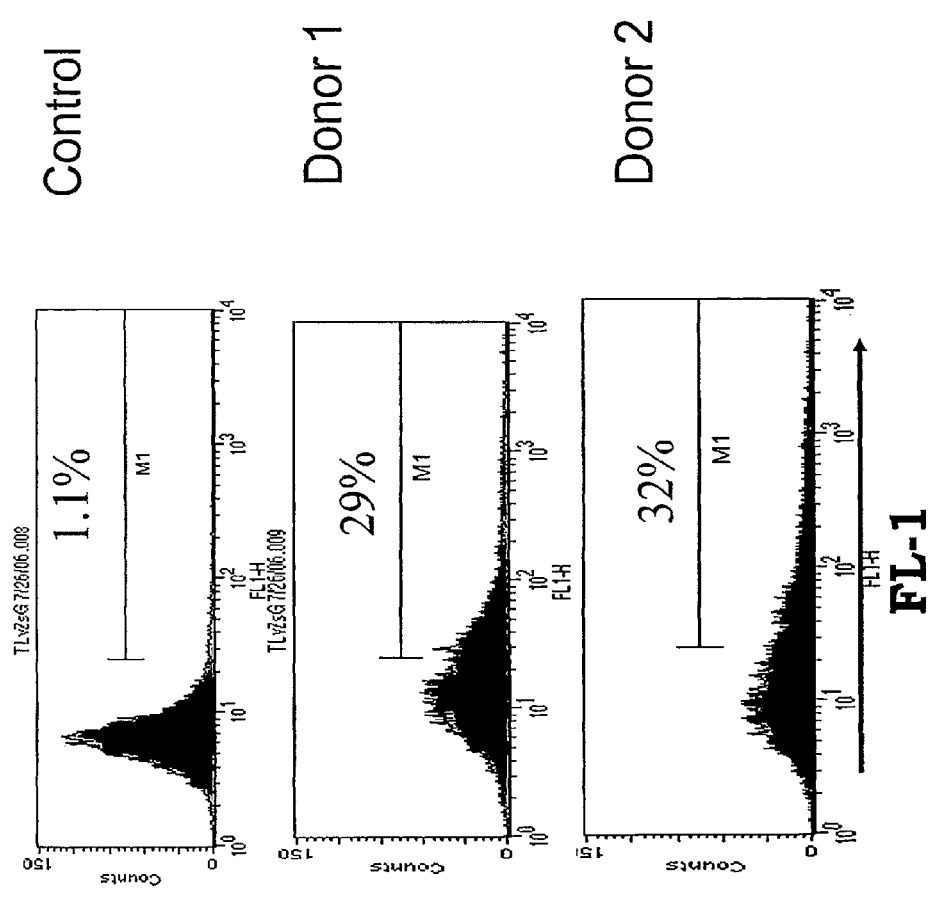
FIG. 28 is a series of graphs showing FACS analyses of transduced 293T cells with six self-inactivating lentiviral vectors encoding different anti-CA IX chimeric T cell receptors in the first cassette and GFP in the second cassette. Chimeric T cell receptors were identified by staining with Mab 1D4 against the C9 tag.
Figure 29:
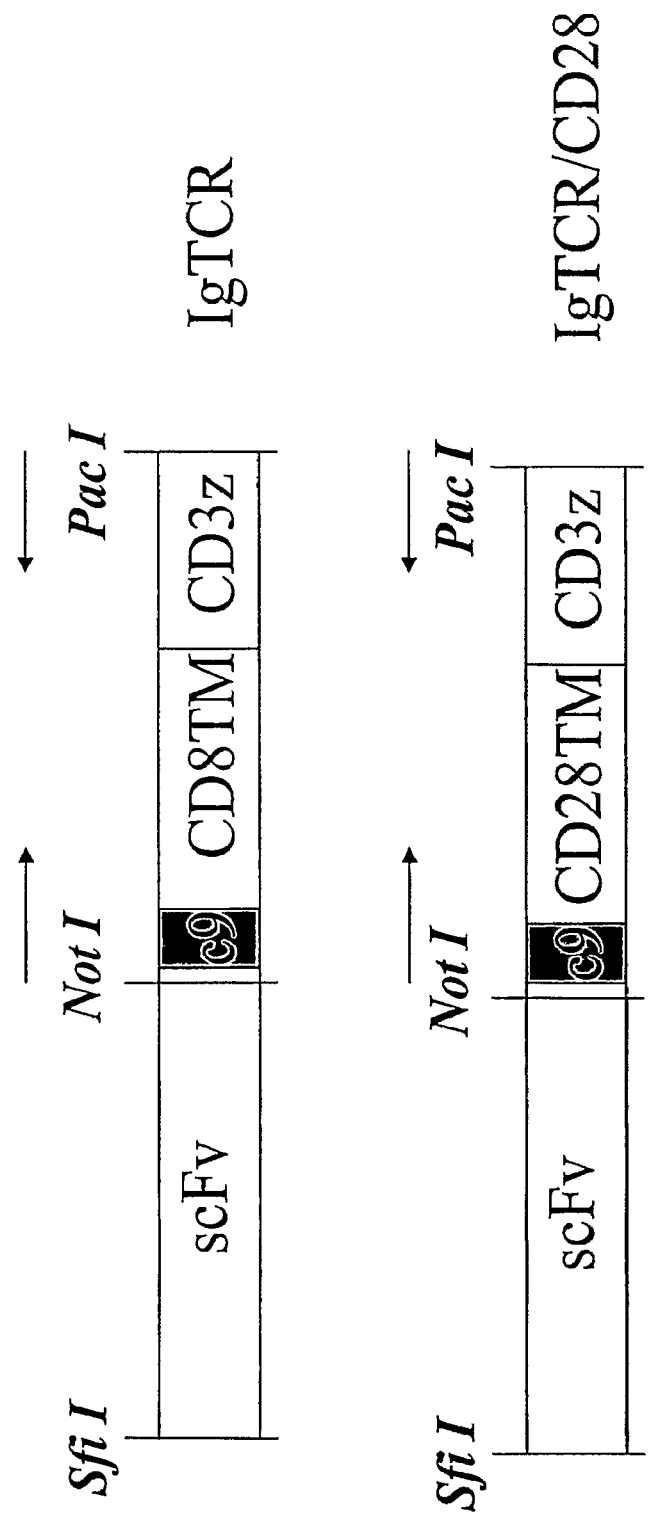
FIG. 29 is a schematic illustration of the insertion of C9 tag into the transmembrane region of TCR.

As shown in FIGS. 24 and 25, four of eighteen G250 specific scFv-Fc antibodies, which have been, tested show Carbonic Anhydrase inhibition function at a dose-dependent pattern. The maximal inhibitions of clone G6 and G39 reach about 50% while those for clone G37 and G125 are around 40%. CA inhibitor acetazolamide almost abolishes the function of G250-ECD-Fc at molar ratio of inhibitor:enzyme=1:1; on the other hand, the non-related antibody X33 doesn't have effect on the function of CA.

Example 20

PET Evaluation of RCC Metastases Using High-Affinity Human Anti-CAIX Monoclonal Antibodies with Optimized Pharmacokinetic Properties Renal cell carcinoma (RCC) accounts for 3% of all adult malignancies and there are 36,000 new cases diagnosed each year in the United States. RCC is resistant to virtually all conventional modes of treatment, such as radiotherapy and chemotherapy. RCC is one of the few tumors where spontaneous regression of metastatic disease has been documented after tumor nephrectomy, treatment with placebo in phase III trials or after inflammatory or infectious events. These observations have provided strong evidence of the importance of the immune system in the control of this cancer. Therefore, much attention has been focused on immunotherapeutic modalities for the treatment of RCC, including the treatment with high-dose IL-2 which remains the preferred therapy for select patients with metastatic RCC.

Carbonic anhydrase IX (CAIX) is a RCC-associated surface antigen that is not expressed in normal kidney or other tissue except for epithelial cells of the bile ducts and small intestine and mucous cells of the gastric epithelium where in contrast to RCC, expression is localized to the cytoplasm. CAIX (also known as G250 and MN) is a N-glycosylated transmembrane protein that binds zinc and has carbonic anhydrase (CA) activity. The extracellular portion is composed of two distinct domains, a region between the signal peptide and the CA domain (aa 53-111) shows significant homology with a keratin sulfate attachment domain of a human large aggregating proteoglycan, aggrecan and a carbonic anhydrase domain that is located close to the plasma membrane (aa 135-391). The CAIX antigen appears at malignant transformation and stains positive in about 95% of clear cell RCC specimens as well as in most renal cell metastases. CAIX is thought to promote tumor cell proliferation in response to hypoxic conditions.

Several recent studies have focused on identifying molecular markers that might predict the outcomes of patients with RCC. Immunohistochemical analysis of CAIX on paraffin embedded specimens from 224 patients treated with nephrectomy for RCC. In this study, >90% of tumors expressed CAIX and its expression decreased with advancing stage of disease. Importantly, overall expression of CAIX was found to decrease with development of metastasis; as demonstrated by the lower CAIX staining levels in metastatic lesions relative to matched primary tumor specimens. These findings were expanded by examining CAIX expression in pathology specimens from 66 RCC patients who had previously received IL-2 therapy. These results showed that high CAIX expression was an important predictor of response to IL-2 therapy and prolonged survival. These and other studies suggest that improved diagnostic strategies that incorporate CAIX expression may help to identify those patients that are most likely to benefit from IL-2 based therapy which is associated with considerable toxicity and expense, making it an impractical standard therapy Diagnostic and therapeutic Mabs against CAIX have been extensively studied by two groups in The Netherlands (murine G250 Mab and derived cG250, chimeric Mab licensed to Wilex) and Czech Republic (murine MAb M75, licensed to Chiron). Both of these antibodies are directed against the PG domain of CAIX. Interestingly, attempts to produce Mabs against other parts of CAIX through conventional immunization procedures in mice have been unsuccessful due to the immunodominance of the PG region and the fact that this is the only region of CAIX that significantly differs between human and mouse homologues. The murine M75 Mab has been used in radioimmunoscintigraphy studies only in mice however, these investigators have obtained similar pharmacokinetic, biodistribution and tumor localization results as have been reported in animal studies that have used murine G250 Mab and the derived chimeric cG250 Mab. The chimeric G250 mAb (WX-G250) is being developed by Wilex for both diagnostic and therapeutic purposes. The parental G250 and chimeric cG250 Mabs have demonstrated excellent tumor targeting in immunoscintigraphy studies in humans and limited clinical responses in radioimmunotherapy phase I trials of advanced RCC have been reported. Together, these studies clearly illustrate that CAIX is an excellent tumor-associated antigen for imaging of RCC in vivo and can provide important diagnostic and prognostic information that could markedly improve the clinical management of this disease.

MicroPET Evaluation of $[I^{124}]$-Labeled Antibody Fragments (scFvFc) in Non-Internalizing (CEA and CD20) Verses $[Cu^{64}]$-scFvFc Fragments for Internalizing (HER2 and PSCA) Tumor Antigen Systems.

The serum persistence of IgG1 and fragments with intact Fc region is controlled by the protective neonatal Fc receptor (FcRn) receptor. Essential for the FcRn binding, in both humans and rodents, are the residues Ile253 and His310 in the CH2 domain and H435 in the CH3 domain (Kabat numbering system). MicroPET imaging has been used to examine the pharmacokinetics of several mutants of bivalent single-chain antibody (scFv)-Fc (dimer of Hinge-CH$_2$-CH$_3$ human IgG1, 105 kDa) fusion proteins (scFvFc) for their blood clearance properties and tumor imaging properties. Specifically the double mutation H310A/H435Q (scFvFc DM) has been shown to have superior tumor imaging in vivo. In particular, the fastest clearing scFvFc DM variant also exhibited high-contrast microPET images in murine xenografts when labeled with $[I^{124}]$ (t1/2=4.2 d) as compared to wild-type and several single-mutant proteins (Kenanova, 2005)

Production, Purification and In Vitro Characterization of Human Anti-CAIX scFvFc DM Proteins.

scFvFc human IgG1 expression vectors have been constructed that contain the optimized H310A/H435Q double mutation as described above. This cassette accommodates all the human anti-CAIX scFvs described herein though unique in frame 5-Sfi1 and 3'-Not1 restriction sites after the IgG leader and before the doubly mutated Fc, respectively. Transient transfection of 293F or 293FT cells using the calcium chloride precipitation technique results in high levels of antibody secretion, sufficient to obtain several milligrams of antibody from cells seeded on 100 mm plates. Two or three of the highest affinity anti-CAIX scFvs that map to different regions (GP domain, carbonic anhydrase domain) will be used for production of scFvFc DM proteins.

Because the scFvFc DM proteins bind poorly to protein A (most likely because the FcRn binding region overlaps with protein A interactions a three-step purification scheme as described by Olafen, 2005 will be used. Briefly, culture supernatants will be dialyzed against 50 mmol/L acetic acid (ph 5.0) before being loaded onto a cation exchange column (Poros HS20, Perkin-Elmer, Foster City, Calif.). Bound protein are eluted with a NaCl gradient and the eluted fractions, containing the scFvFc DM proteins are pooled and following buffer adjustments are loaded onto a hydroxyapatite column (Macro-Prep type I, Bio-Rad Labs). Bound proteins are eluted with a Kpi gradient and again the eluted fractions containing the scFvFc DM proteins will be pooled, buffer adjustments made and loaded onto an anion exchange column (Source 15Q, Amersham Biosciences Corp.). Bound proteins are eluted with a NaCl gradient. The fractions with the scFvFc DM will be analyzed by SDS-PAGE and the fractions containing the purified antibodies will be pooled. Aliquots of purified proteins will be analyzed by SDS-PAGE under reducing and non-reducing conditions. Samples will also be subjected to size-exclusion high-pressure liquid chromatography (HPLC) pm a Superdex 200 HR 10/30 column (Amersham Biosciences). Retention times will be compared with standards. Binding of the purified proteins will be assessed by FACS analysis using CAIX(+)-SK-RC-52 and CAIX(−)-SK-59 human RCC cells (obtained from Memorial Sloan-Kettering, NY)

Establishment of Orthotopic and Metastatic Models of RCC in Athymic Mice.

Both spontaneous and experimental metastases model in female Ncr Nude mice (Taconic) will be established by intravenous and subcutaneous injection of luciferase expressing CAIX(+)-SK-RC-52 and CAIX(−)-SK-59 human RCC cells tumor cells, respectively. The presence of lung and other metastases will be assessed using the Xenogen imaging system. For both metastasis models, the experiments is expected to run for approximately four to six weeks and each animal will be imaged weekly (or more frequently if required) by Xenogen imaging. For the intravenous administration experiments, 0.3 ml of $10^6$ tumor cell suspension in PBS will be injected into the tail vein of mice. Mice will be injected with D-Luciferin before performing the Xenogen imaging. At a time when metastases are present, the animals will be sacrificed and tissues collected for histologically examination and immunohistology evaluation for expression of CAIX and other HIF-indicible proteins including CXCR4, Glut-1 and other markers that may be of interest. For the subcutaneous administration experiments, 0.3 ml of $10^7$ tumor cell suspension in PBS will be orthotopically injected into mammary fat pads. Mice will be monitored daily and when tumor diameter reach 1.5 cm, the primary tumor will be surgically removed. These mice will also be subjected to Xenogen imaging and upon sacrifice tissues examined for metastases as described above.

Perform microPET Imaging on Athymic Mice Bearing Luciferase Expressing G250(+)-SK-RC-52 Human Tumors Using Several Anti-G250 scFvFc DM Labeled with [$I^{124}$] and [$Cu^{64}$].

In vivo pharmacokinetic and biodistribution studies will first be carried out in non-tumor bearing mice. Both [$I^{124}$] and [$Cu^{64}$] imaging will be performed initially since it is not known at this time whether CAIX undergoes efficient internalization either spontaneously or after scFvFc DM antibody binding. As described in above [$I^{124}$] imaging is optimal for non-internalizing receptors whereas [$Cu^{64}$] is very useful for imaging receptors that undergo internalization. Labeling with $I^{124}$ (half-life, 4.2 d) is performed using the iodogen method (labile, goes onto tyrosines) whereas conjugation with DOTA is required to radiolabel with Cu-64 (half-life, 12.7 h).

The ability to detect the tumors both with bioluminescence and microPET imaging will provide a powerful system to examine the sensitivity of the radiolabeled scFvFc DM proteins as imaging agents for metastatic lesions. MicroCT imaging will be used to provide anatomical localization.

Establishment of Stably Transfected CHO Cell Lines Secreting High Levels of the Optimal Anti-CAIX scFvFc DM Proteins.

The imaging studies described above will provide important information as to the lead anti-CAIX scFvFc DM protein that should be moved forward for human clinical studies. Specifically, human IgG1 expression plasmids that encode the dihydrofolate reductase (DHFR) gene, and the dominant selectable marker neomycin phosphotransferase (Neo) gene have been constructed. Very high levels of scFvFc DM protein production are induced by forcing the antibody cassette to undergo gene amplification by selection in methotrexate (MIX) for the dihydrofolate reductase gene. Amplification is achieved by increasing concentrations of MTX (5 nM→50 nM→500 nM) to the CHO DG44 cells, the best amplificants from the 5 nM MTX stage are further amplified at the 50 nM and 500 nM stage. At this stage, the selected amplificants are readapted to grow in spinner flasks. During this time transfectoma antibody can be purified from the supernatant. When the cell is producing 50-100 pg/cell/day and has a doubling time of 36 hrs or less, it will be considered a production cell line and a Parent Seed Stock will be prepared.

REFERENCES

Baselga J, Norton L, Albanell J, Kim Y M and Mendelsohn. Recombinant humanized anti-HER2 antibody (Herceptin) enhances the anti-tumor activity of paclitaxel and doxorubicin against HER2/neu overexpressing human breast cancer xenografts. Cancer Res. 58:2825-2831, 1998.

Brentens R J, Latouche J-B, Santos E, Marti F, Gong M C, Lyddane C, King P D, Larson S, Weiss M, Riviere I and Sadelain M. Eradication of systemic B-cell tumors by genetically targeted huma T lymphocytes co-stimulated by CD80 and interleukin-15. Nature Med. 9:279-286, 2003.

Brion L P, Schwartz J H, Zavilowitz B J and Schwartz G J. Micro-method for the measurement of carbonic anhydrase activity in cellular homogenates. Anal. Biochem. 175:289-297, 1988.

Carnahan J, Wang P, Kendall R, Chen C, Hu S, Boone T, Juan T, Talvenheimo J, Montestruque S, Sun J, Elliott G, Thomas J, Ferbas J, Kern B, Briddell R, Leonard J P and Cesano A. Epratuzumab, a humanized monoclonal antibody targeting CD22: characterization of in vitro properties. Blood 9:3982s-3900s (Suppl.), 2003.

De Haard H J, Van Neer N, Reurs A, Hufton S E, Roovers R C, Henderikx P, De Bruine A P, Arends J W, Hoogenboom H R. A large non-immunized human fac fragment phage library that permits rapid isolation and kinetic analysis of high affinity antibodies. J Biol Chem 1999; 274(26): 18218-18230.

Dodgson S J, Tashian R E, Gross G and Carter N D. The carbonic anhydrases. Plenum, New-York-London, 1991.

Doege K J, Sasaki M, Kimura T and Yamada Y. Complete coding sequence and deduced primary structure of the human cartilage aggregating proteoglycan, aggrecan. J. Biol. Chem. 266:894-902, 1991.

Ebert T, Bander N H, Finstad C L, Ramsawak R D and Old L J. Establishment and characterization of human renal cancer and normal kidney cell lines. Cancer Res. 50:5531-5536, 1990.

Guilford P. E-cadherin downregulation in cancer: fuel or fire? Mol. Med. Today 5:172-177, 1999.

Grabmaier K, Vissers J L M, DeWeijert M C A, Oosterwijk-Wakka J C, van Bokhoven A, Bradenhiff R H, Noessner E, Mulders P A, Merkx G, Figdor C G, Adema G J and Oosterwijk E. Molecular cloning and immunogenicity of renal cell carcinoma-associated antigen G250. Int. J. Cancer 85:865-870, 2000.

Griffiths A D, Williams S C, Hartley O, Tomlinson I M, Waterhouse P, Crosby W L, Kontermann R E, Jones P T, Low N M, Allison T J, Prospero T D, Hoogenboom H R, Nissim A, Cox J P L, Harrison J L, Zaccolo M, Gherardi E and Winter G. Isolation of high affinity human antibodies directly from large synthetic repertoires. EMBO J. 1994; 13: 3245-3260.

Hanahan D. Folkman J. Paterns and emerging mechanisms of the angiogenic switch during tumorigenesis. Cell 86:353-364, 1996.

Hurwitz A A, Foster B A, Kwon E D, Truong T, Choi E M, Greenberg N M, Burg M B and Allison J P. Combination immunotherapy of primary prostate cancer in a transgenic mouse model using CTLA-4 blockade. Cancer Res. 60:2444-2448, 2000.

Ivanov S V, Kuzmin I, Wei M H, Pack S, Geil L, Johnson B E, Stanbridge E J and Lerman M I. Down-regulation of transmembrane carbonic anhydrases in renal cell carcinoma cell lines by wild-type Hippel-Landau transgenes. Proc. Nat'l. Acad. Sci. 95:12596-12601, 1998.

Ivanov S, Liao S-Y, Ivanova A, Danilkovitch-Miagkova A, Tarasova N, Weirich G, Merrill M J, Proescholdt M A, Oldfield E H, Lee J, Zavada J, Waheed A, Sly W, Lerman M I, and Stanbridge E J. Expression of hypoxia-inducible cell-surface transmembrane carbonic anhydrase in human cancer. Am. J. Pathol. 158:905-919, 2001.

Karlsson R, Michaelsson A, and Mattson L. Kinetic analysis of monoclonal antibody-antigen interactions with a new biosensor based analytical system. J Immunol Methods 1991; 145:229-240.

Kawai K, Saijo K, Oikawa T, Morishita Y, Noguchi M, Ohno T, Akaza H. Clinical course and immune response of a renal cell carcinoma patients to adaptive transfer of autologous cytotoxic T lymphocytes. Clin. Ex. Immunol 134: 264-269, 2003.

Kwon E D, Foster B A, Hurwitz A A, Madias C, Allison J P, Greenberg N M, and Burg M B. Elimination of residual metastatic prostate cancer after surgery and adjunctive cytotoxic T lymphocyte-associated antigen 4 (CTLA-4) blockade immunotherapy. Proc. Nat'l. Acad. Sci. 96:15074-15079, 1999.

Lamers C H J, Willemsen R A, Luider B A, Debets R, and Bolhuis R L H. Protocol for gene transduction and expansion of human T lymphocytes for clinical immunogene therapy of cancer. Cancer Gene Ther. 9:613-623, 2002.

Liao S Y, Brewer C, Zavada J, Pastorek J, Pastorekova S, Manetta A, Bermann M L, DiSaia P J and Stanbridge E J. Identification of the MN antigen as a diagnostic biomarker of cervical intraepithelial squamous and glandular neoplasm and cervical carcinomas. Am. J. Pathol. 145:598-609, 1994.

Liu S Q, Kawai K, Shiraiwa H, Hayashi H, Akaza H, Hashizaki K, Shiba R, Saijo K and Ohno T. High rate of induction of human autologous cytotoxic T lymphocytes against renal carcinoma cells cultured with an interleukin cocktail. Jpn. J. Cancer Res. 89:1195-1201, 1998.

Liu Z, Smyth F E, Renner C, Lee F-T, Oosterwijk E and Scott A M. Anti-renal cell carcinoma chimeric antibody G250: cytokine enhancement of in vitro antibody-dependent cellular cytotoxicity. Cancer Immunol. Immunother. 51:171-177, 2002.

Maher J, Brentjens R J, Gunset G, Rivière I and Sadelain M. Human T-lymphocyte cytotoxicity and proliferation directed by a single chimeric TCRζ/CD28 receptor. Nature Biotech. 20:70-75, 2002.

Maxwell P H, Wiesener M S, Chang G W, Clifford S C, Vaux E C, Cockman M E, Wykoff C C, Pugh C S, Maher E R, and Ratcliffe P J. The tumor suppressor protein VHL targets hypoxia-inducible factors for oxygen-dependent proteolysis. Nature 399:271-275, 1999.

Michael A and Pandha H S. Renal-cell carcinoma: tumour markers, T-cell epitopes, and potential for new therapies. The Lancet Oncol. 4:215-223, 2003.

Mirzabekov T, Kontos H, Farzan M, Marasco W, Sodroski J. Paramagnetic Proteoliposomes Containing a Pure, Native, and Oriented Seven-Transmembrane Segment Protein, CCR5. Nature Biotech. 2000; 18:649-654.

Mostfi F K and Davis C J. WHO international histological classification of tumors. Berlin: Springer, 1998.

Nissim A, Hoogenboom H R, Tomlinson I M, Flynn G, Midgley C, Lane D and Winter G. Antibody fragments from a 'single pot' phage display library as immunochemical reagents. EMBO J. 1994; 13:692-698.

Ogueta S B, Yao F, and Marasco W A. Design and in vitro characterization of a single regulatory module for efficient control of gene expression in both plasmid DNA and a self-inactivating lentiviral vector. Mol Med 2001; 7:569-71.

Ohh M, Kaelin W G. The von Hipple-Lindau tumor suppressor protein: New prospectives. Mol. Med. Today 6:257-263, 1999.

Oosterwijk E, Ruiter D J, Hoedemaeker Ph J, Pauwels E K J, Jonas U, Zwartendijk J and Warnaar S O. Monoclonal antibody G250 recognizes a determinant present in renal-cell carcinoma and absent from normal kidney. Int. J. Cancer 38:489-494, 1986.

Parkkila S, Rajaniemi H, Parkkila A-K, Kivela J, Waheed A, Pastorekova S, Pastorek J and Sly W S. Carbonic anhydrase inhibitor suppresses invasion of renal cancer cells in vitro. Proc. Nat'l. Acad. Sci. 97:2220-2224, 2000.

Pastorek J, Pastorekova S, Callebaut I, Momon J P, Zelnik V, Opavsky R, Zatovicova M, Liao S, Portelle D, Stanbridge E J, Zavada J, Burny A and Kettmann R. Cloning and characterization of MN, a human tumor-associated protein with a domain homologous to carbonic anhydrase and a putative helix-loop-helix DNA binding segment. Oncogene 9:2788-2888, 1994.

Pastoreková S, Závadová Z, Košt'ál M, Babušiková O and Závada J. A novel quasi-viral agent, MaTu, is a two-component system. Virology 187:620-626, 1992.

Pinthus J H, Waks T, Kaufman-Francis K, Schindler D G, Harmelin A, Kanety H, Ramon J and Eshhar Z. Immunogene therapy of established prostate tumors using chimeric receptor-redirected human lymphocytes. Cancer Res. 63:2470-2476, 2003.

Rivière I, Sadelain M and Brentjens R J. Novel strategies for cancer therapy: The potential of genetically modified T lymphocytes. Curr. Hematol. Reports. 3:290-297, 2004.

Salmon P, Kindler V, Ducrey O, Chapuis B, Zubler R H, Trono D. High-level transgene expression in human hematopoietic progenitors and differentiated blood lineages after transdcution with improved lentiviral vectors. Blood 96:3392-3398, 2000.

Semenza G L. Hypoxia, clonal selectin, and the role of HIF-1 in tumor progression. Crit. Rev. Biochem. Mol. Biol. 35:71-103, 2000.

Sheets M D, Amersdorfer P, Finnern R, Sargent P, Lindqvist E, Schier R, Hemingsen G, Wong C, Gerhart J C, and Marks J D. Efficient construction of a large nonimmune phage antibody library: The production of high-affinity human single-chain antibodies to protein antigens. Proc Natl Acad Sci USA 1998; 956:6157-6162.

Steffens M G, Boerman O C, Oosterwijk-Wakka J C, Oosterhof G O N, Witjes J A, Koenders E B, Oyen W J G, Buijs W C A M, Debruyne F M J, Corstens F H M and Oosterwijk E. Targeting of renal cell carcinoma with iodine-131-labeled chimeric monoclonal antibody G250. J. Clin. Oncol. 15:1529-1537, 1997.

Steffens M G, Boerman O C, de Mulder P H M, Oyen W J G, Buijs W C A M, Wites A, van den Broek W J M, Oosterwijk-Wakka J C, Debruyne F M J, Corstens F H M, and Oosterwijk E. Phase I radioimmunotherapy of metastatic renal cell carcinoma with $^{131}$I-labeled chimeric monoclonal antibody G250. Clin. Cancer Res. 5:3268s-3274s, 1999.

Sui J, Li W, Murakami A, Tamin A, Matthews L J, Wong S K, Moore M J, Tallrico A S, Olurinde M, Choe H, Anderson L J, Bellini W J, Farzan M, and Marasco W A. Potent Neutralization of SARS Coronavirus Infection by a Human Monoclonal Antibody Against the ACE2-Binding Domain of Spike Protein. Proc Natl Acad Sci USA. 2004 Feb. 24; 101(8):2536-41.

Svastova E, Zilka N, Zatovicova M, Gibadulinova A, Ciampor F, Pastorek J and Pastorekova S. Carbonic anhydrase IX reduces E-cadherin-mediated adhesion of MDCK cells via interaction with β-catenin. Exp. Cell Res. 290:332-345, 2003.

Tsui L V, Kelly M, Zayek N, Rojas V, Ho K, Ge Y, Moskalenko M, Mondesire J, Davis J, Van Roey M, Dull T and McArthur J G. Production of human clotting factor IX without toxicity in mice after vascular delivery of a lentiviral vector. Nature Biotech. 20:53-57, 2002.

Vaughan T J, Williams A J, Pritchard K, Osbourn J K, Pope A R, Earnshaw J C, McCafferty J, Hodits R A, Wilton J, and Johnson K S. Human antibodies with sub-nanomolar affinities isolated from a large non-immunized phage display library. Nature Biotech 1996; 14:309.

Walsh P C, Retik A B, Vaughan E D, Wein A J, Kavoussi L R, Novick A C, Partin A W, and Peters C A. Campbell's Urology 8$^{th}$ edition. Philadelphia, London, New York, St. Louis, Sydney, Toronto: Saunders; 2003.

Weijtens M E M, Willemsen R A, Valerio D, Stam K and Bolhuis R L H. Single chain Ig/γ gene-redirected human T lymphocytes produce cytokines, specifically lyse tumor cells, and recycle lytic capacity. J. Immunol. 157:836-843, 1996.

Yang J C, Haworth L, Sherry R M, Hwu P, Schwartzentruber D J, Topalian S L, Steinberg S M, Chen H X and Rosenberg S A. A randomized trial of bevacizumab, an anti-vascular endothelial growth factor antibody, for metastatic renal cancer. N. Eng'l. J. Med. 349:427-434, 2003.

Zatovicova M, Tarabkova K, Svastova E, Gibadulinova A, Mucha V, Jakubickova L, Biesova Z, Rafojova M, Gut M O, Parkkila S, Parkkila A-K, Waheed A, Sly W S, Horak I, Pastorek J and Pastorekova S. J. Immunol. Methods 282L117-134, 2003.

Závada J, Závadová Z, Machon O, Kutinova L, Nemeckova S, Opavsky R and Pastorek J. Transient transformation of mammalian cells by MN protein, a tumor-associated cell adhesion molecule with carbonic anhydrase activity. Int. J. Oncol. 10:857-863, 1997.

Závada J, Závadová Z, Pastoreková S, Caimpor F, Pastorek J and Zelnik V. Expression of MaTu-MN protein in human tumor cultures and in clinical specimens. Int. J. Cancer 54:268-274, 1993.

Závada J, Závadová Z, Pastorek J, Biesova Z, Jezek J and Velek J. Human tumour-associated cell adhesion protein MN.CA IX: identification of M75 epitope and of the region mediating cell adhesion. Brit. J. Cancer 82(11): 1808-1813, 2000.

Zhu Q, Ricardo R R, Zhang L, Ogueta S B, Agrawal R S, Dzau V J, and Marasco W A. Development of constitutive and inducible self-inactivating lentiviral vectors and their application in cardiovascular gene transfer. Gene Ther Mol. Biol., 2004; (8): 91-102.

Zufferey R, Dull T, Mandel R J, Bukovsky A, Quiroz D, Naldini L and Trono D. Self-inactivating lentivirus vector for safe and efficient in vivo gene delivery. J. Virol. 72:9873-9880, 1998.

OTHER EMBODIMENTS

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. Other aspects, advantages, and modifications considered to be within the scope of the following claims. The claims presented are representative of the inventions disclosed herein. Other, unclaimed inventions are also contemplated. Applicants reserve the right to pursue such inventions in later claims.

We claim:

1. An isolated human monoclonal antibody that immunospecifically binds to a carbonic anhydrase IX (G250) protein, wherein said antibody
    (a) has a heavy chain with a CDR1 comprising an amino acid sequence SYAMS (SEQ ID NO: 55);
    (b) has a heavy chain with a CDR2 comprising an amino sequence AISXXGGXTXXADSVKG (SEQ ID NO: 58);
    (c) has a heavy chain with a CDR3 comprising an amino sequence NGNYRGAFDI (SEQ ID NO: 65);
    (d) has a light chain with a CDR1 comprising an amino sequence TGSSSNIGAGYDVH (SEQ ID NO: 61);
    (e) has a light chain with a CDR2 comprising an amino sequence GNNNRPS (SEQ ID NO: 62); and
    (f) has a light chain with a CDR3 comprising an amino sequence QSYDSSLSAWVV (SEQ ID NO: 63),
    and wherein said antibody reduces carbonic anhydrase activity of said protein.

2. The antibody of claim 1, wherein said monoclonal antibody binds to the carbonic anhydrase (CA) domain of carbonic anhydrase IX (G250).

3. An isolated scFv antibody, wherein said scFv antibody binds to a carbonic anhydrase IX (G250) protein, wherein said scFv antibody has a heavy chain comprising an amino acid sequence SEQ ID NO: 7, and wherein said scFv antibody has a light chain comprising an amino acid sequence SEQ ID NO: 28.

4. The isolated scFv antibody of claim 3, wherein said scFv antibody binds to the carbonic anhydrase (CA) domain of a carbonic anhydrase IX (G250) protein.

5. The scFv antibody of claim 4, wherein said binding affinity is from about $10^{-6}$ M to about $10^{-12}$ M.

6. An antibody complex comprising:
    a) a first fully human monoclonal antibody that binds to a carbonic anhydrase IX (G250) protein, operably linked to
    b) a second fully human monoclonal antibody that binds to a carbonic anhydrase IX (G250) protein, wherein said antibody complex reduces carbonic anhydrase activity, and wherein the first fully human monoclonal antibody is the antibody of claim 1 or the scFv antibody of claim 4.

7. The antibody of claim 6, wherein said first and second antibodies do not bind to the same epitope.

8. The monoclonal antibody of claim 1, or a functional fragment thereof wherein said antibody contains a H310A and a H435Q mutation when numbered in accordance with the Wu and Kabat numbering system, and wherein said functional fragment binds the CA IX (G250) protein.

9. A fusion protein comprising the monoclonal antibody of claim 1, or a functional fragment thereof, operably linked to an IL-2 polypeptide, wherein said functional fragment binds CA IX(250) protein.

10. A fusion protein comprising the monoclonal antibody of claim 1, or a functional fragment thereof, operably linked to an IgG molecule, wherein said functional fragment binds the CA IX (G250) protein.

11. A fusion protein comprising the monoclonal antibody of claim 1, or a functional fragment thereof, operably linked to a zeta chain of the T-cell receptor complex, wherein said functional fragment binds CA IX(250) protein.

12. The fusion protein of claim 11, further comprising a CD28 polypeptide.

13. A minibody comprising the binding domain of the monoclonal antibody of claim 1, or a functional fragment thereof, and a constant region of an immunoglobulin or fragment thereof, wherein said functional fragment binds the CA IX (G250) protein.

14. A composition comprising the monoclonal antibody of claim 1 and a carrier.

15. The composition of claim 14, further comprising IL-2.

16. A kit comprising, in one or more containers, the composition of claim 14.

17. The isolated antibody of claim 4, wherein said antibody reduces carbonic anhydrase activity of said protein.

* * * * *

SEQUENCE LISTING

```
<160> NUMBER OF SEQ ID NOS: 65

<210> SEQ ID NO 1
<211> LENGTH: 121
<212> TYPE: PRT
<213> ORGANISM: Homo sapiens

<400> SEQUENCE: 1

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Gly Asn Tyr Arg Gly Ser Leu Ala Phe Asp Ile Trp Gly
            100                 105                 110

Gln Gly Thr Leu Val Thr Val Ser Ser
            115                 120

<210> SEQ ID NO 2
<211> LENGTH: 113
<212> TYPE: PRT
<213> ORGANISM: Homo sapiens

<400> SEQUENCE: 2

Gln Ser Val Leu Thr Gln Pro Pro Ser Val Ser Gly Ala Pro Gly Gln
  1               5                  10                  15

Arg Val Thr Ile Ser Cys Thr Gly Ser Ser Ser Asn Ile Gly Ala Gly
                 20                  25                  30

Tyr Asp Val His Trp Tyr Gln Gln Leu Pro Gly Thr Ala Pro Lys Leu
             35                  40                  45

Leu Ile Tyr Gly Asn Asn Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Ala Trp Val Val Phe Gly Gly Gly Thr Lys Leu Thr Val Leu
            100                 105                 110

Gly

<210> SEQ ID NO 3
<211> LENGTH: 119
<212> TYPE: PRT
<213> ORGANISM: Homo sapiens

<400> SEQUENCE: 3

Glu Val Gln Leu Val Gln Ser Gly Gly Val Val Gln Pro Gly Gly
  1               5                  10                  15

Ser Leu Arg Leu Ser Cys Ala Ala Ser Gly Phe Pro Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Ala Asn Gly Gly Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Asn Asn Gly Asn Tyr Arg Gly Ala Phe Asp Ile Trp Gly Gln Gly
            100                 105                 110

Thr Met Val Thr Val Ser Ser
            115

<210> SEQ ID NO 4
<211> LENGTH: 119
<212> TYPE: PRT
<213> ORGANISM: Homo sapiens
```

<400> SEQUENCE: 4

```
Gln Val Gln Leu Val Gln Ser Gly Gly Gly Leu Val Gln Pro Gly Gly
1               5                   10                  15
Ser Leu Arg Leu Ser Cys Ala Ala Ser Gly Phe Pro Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Ala Asn Gly Gly Thr Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Asn Asn Gly Asn Tyr Arg Gly Ala Phe Asp Ile Trp Gly Gln Gly
            100                 105                 110
Thr Met Val Thr Val Ser Ser
        115
```

<210> SEQ ID NO 5
<211> LENGTH: 119
<212> TYPE: PRT
<213> ORGANISM: Homo sapiens

<400> SEQUENCE: 5

```
Gln Val Gln Leu Val Gln Ser Gly Gly Gly Leu Val Gln Pro Gly Gly
1               5                   10                  15
Ser Leu Arg Leu Ser Cys Ala Ala Ser Gly Phe Pro Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Ala Asn Gly Gly Thr Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Asn Asn Gly Asn Tyr Arg Gly Ala Phe Asp Ile Trp Gly Gln Gly
            100                 105                 110
Thr Met Val Thr Val Ser Ser
        115
```

<210> SEQ ID NO 6
<211> LENGTH: 119
<212> TYPE: PRT
<213> ORGANISM: Homo sapiens

<400> SEQUENCE: 6

```
Gln Val Gln Leu Val Gln Ser Gly Gly Gly Leu Val Gln Pro Gly Gly
1               5                   10                  15
Ser Leu Arg Leu Ser Cys Ala Ala Ser Glu Phe Thr Phe Gly Thr Tyr
            20                  25                  30
Ala Met Thr Trp Val Arg Gln Ala Pro Gly Lys Gly Leu Glu Trp Val
        35                  40                  45
Ser Ala Val Ser Gly Ser Gly Gly Ser Thr Tyr Tyr Ala Asp Ser Val
    50                  55                  60
Lys Gly Arg Phe Thr Ile Ser Arg Asp Asn Ser Arg Asn Thr Leu Tyr
65                  70                  75                  80
```

```
Leu Gln Met Asn Ser Leu Arg Ala Asp Asp Thr Ala Val Tyr Tyr Cys
                85                  90                  95

Ala Arg Gly Pro Val Leu Arg Tyr Gly Phe Asp Ile Trp Gly Gln Gly
            100                 105                 110

Thr Met Val Thr Val Ser Ser
        115

<210> SEQ ID NO 7
<211> LENGTH: 119
<212> TYPE: PRT
<213> ORGANISM: Homo sapiens

<400> SEQUENCE: 7

Gln Val Gln Leu Val Gln Ser Gly Gly Val Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Met Val Thr Val Ser Ser
        115

<210> SEQ ID NO 8
<211> LENGTH: 118
<212> TYPE: PRT
<213> ORGANISM: Homo sapiens

<400> SEQUENCE: 8

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Ser Ala Tyr Ser Gly Tyr Asp Leu Trp Gly Gln Gly Thr
            100                 105                 110

Leu Val Thr Val Ser Ser
        115

<210> SEQ ID NO 9
<211> LENGTH: 119
<212> TYPE: PRT
<213> ORGANISM: Homo sapiens
```

```
<400> SEQUENCE: 9

Gln Val Gln Leu Val Gln Ser Gly Gly Gly Leu Val Arg Pro Gly Gly
 1               5                  10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Thr Val Thr Val Ser Ser
        115

<210> SEQ ID NO 10
<211> LENGTH: 119
<212> TYPE: PRT
<213> ORGANISM: Homo sapiens

<400> SEQUENCE: 10

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Met Val Thr Val Ser Ser
        115

<210> SEQ ID NO 11
<211> LENGTH: 119
<212> TYPE: PRT
<213> ORGANISM: Homo sapiens

<400> SEQUENCE: 11

Glu Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Thr Val Thr Val Ser Ser
        115

<210> SEQ ID NO 12
<211> LENGTH: 116
<212> TYPE: PRT
<213> ORGANISM: Homo sapiens

<400> SEQUENCE: 12

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ala Gly Phe Asp Tyr Trp Gly Gln Gly Thr Leu Val
            100                 105                 110

Thr Val Ser Ser
        115

<210> SEQ ID NO 13
<211> LENGTH: 119
<212> TYPE: PRT
<213> ORGANISM: Homo sapiens

<400> SEQUENCE: 13

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Arg Tyr Ser Ser Ser Leu Gly Tyr Trp Gly Gln Gly
            100                 105                 110

Thr Leu Val Thr Val Ser Ser
        115

<210> SEQ ID NO 14
<211> LENGTH: 122
<212> TYPE: PRT
<213> ORGANISM: Homo sapiens

```
<400> SEQUENCE: 14

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Tyr Ser Ser Leu Asp Ala Phe Asp Ile Trp
            100                 105                 110

Gly Gln Gly Thr Met Val Thr Val Ser Ser
        115                 120

<210> SEQ ID NO 15
<211> LENGTH: 118
<212> TYPE: PRT
<213> ORGANISM: Homo sapiens

<400> SEQUENCE: 15

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser His Ser Ser Gly Phe Asp Tyr Trp Gly Gln Gly Thr
            100                 105                 110

Leu Val Thr Val Ser Ser
        115

<210> SEQ ID NO 16
<211> LENGTH: 118
<212> TYPE: PRT
<213> ORGANISM: Homo sapiens

<400> SEQUENCE: 16

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Arg Ser His Ser Ser Gly Gly Phe Asp Tyr Trp Gly Gln Gly Thr
            100                 105                 110

Leu Val Thr Val Ser Ser
        115

<210> SEQ ID NO 17
<211> LENGTH: 116
<212> TYPE: PRT
<213> ORGANISM: Homo sapiens

<400> SEQUENCE: 17

Gln Val Thr Leu Lys Glu Ser Gly Gly Val Val Gln Pro Gly Thr
1               5                   10                  15

Ser Leu Arg Leu Ser Cys Ala Ala Ser Gly Phe Thr Phe Ser Asn Tyr
                20                  25                  30

Ala Met Thr Trp Val Arg Gln Ala Pro Gly Lys Gly Leu Glu Trp Val
            35                  40                  45

Gly Leu Ile Ser Tyr Asp Gly Ser Val Thr His Tyr Thr Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Ala Asp Asp Thr Ala Val Tyr Tyr Cys
                85                  90                  95

Ala Arg Gly Ser Gly Tyr Gln Glu His Trp Gly Gln Gly Thr Leu Val
            100                 105                 110

Thr Val Ser Ser
        115

<210> SEQ ID NO 18
<211> LENGTH: 118
<212> TYPE: PRT
<213> ORGANISM: Homo sapiens

<400> SEQUENCE: 18

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Tyr Gly Asp Tyr Gly Ser Leu Asp Tyr Trp Gly Gln Gly Thr
            100                 105                 110

Leu Val Thr Val Ser Ser
        115

<210> SEQ ID NO 19
<211> LENGTH: 122
<212> TYPE: PRT
<213> ORGANISM: Homo sapiens

<400> SEQUENCE: 19

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Cys Ser Ser Thr Ser Cys Tyr Arg Gly Met Asp Val Trp
                100                 105                 110

Gly Lys Gly Thr Leu Val Thr Val Ser Ser
            115                 120
```

<210> SEQ ID NO 20
<211> LENGTH: 119
<212> TYPE: PRT
<213> ORGANISM: Homo sapiens

<400> SEQUENCE: 20

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Arg Pro Pro Phe Asp Tyr Trp Gly Gln Gly
                100                 105                 110

Thr Leu Val Thr Val Ser Ser
            115
```

<210> SEQ ID NO 21
<211> LENGTH: 119
<212> TYPE: PRT
<213> ORGANISM: Homo sapiens

<400> SEQUENCE: 21

```
Gln Val Gln Leu Val Gln Ser Gly Gly Gly Val Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
            85                  90                  95

Ala Asn Asn Gly Asn Tyr Arg Gly Ala Phe Asp Ile Trp Gly Gln Gly
            100                 105                 110

Thr Met Val Thr Val Ser Ser
            115

<210> SEQ ID NO 22
<211> LENGTH: 121
<212> TYPE: PRT
<213> ORGANISM: Homo sapiens

<400> SEQUENCE: 22

Gln Val Gln Leu Val Gln Ser Gly Gly Gly Leu Val Gln Pro Gly Gly
1               5                   10                  15

Ser Leu Arg Leu Ser Cys Ala Ala Pro Glu Phe Thr Phe Ser Lys Tyr
            20                  25                  30

Ala Met Ser Trp Val Arg Gln Ala Pro Gly Lys Gly Leu Glu Trp Val
            35                  40                  45

Ser Gly Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ser Ser Arg Ser Gly Tyr Phe Leu Pro Leu Asp Tyr Trp Gly
            100                 105                 110

Gln Gly Thr Leu Val Thr Val Ser Ser
            115                 120

<210> SEQ ID NO 23
<211> LENGTH: 118
<212> TYPE: PRT
<213> ORGANISM: Homo sapiens

<400> SEQUENCE: 23

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ala Ala Val Thr Gly Gly Phe Asp Pro Trp Gly Gln Gly Thr
            100                 105                 110

Leu Val Thr Val Ser Ser
            115

<210> SEQ ID NO 24
<211> LENGTH: 112
<212> TYPE: PRT
<213> ORGANISM: Homo sapiens -continued

<400> SEQUENCE: 24

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Tyr Cys Gln Ser Tyr Asp Ser Arg
                85                  90                  95

Leu Ser Ala Trp Val Phe Gly Gly Gly Thr Lys Leu Thr Val Leu Gly
            100                 105                 110

<210> SEQ ID NO 25
<211> LENGTH: 111
<212> TYPE: PRT
<213> ORGANISM: Homo sapiens

<400> SEQUENCE: 25

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Ser Ser Ala Ser Leu Ala Ile Thr Gly Leu
65                  70                  75                  80

Gln Ala Glu Asp Glu Ala His Tyr Tyr Cys Gln Ser Tyr Asp Arg Ser
                85                  90                  95

Leu Ser Trp Val Phe Gly Gly Gly Thr Lys Leu Thr Val Leu Gly
            100                 105                 110

<210> SEQ ID NO 26
<211> LENGTH: 112
<212> TYPE: PRT
<213> ORGANISM: Homo sapiens

<400> SEQUENCE: 26

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Ala Asp Asp Glu Ala Asp Tyr Tyr Cys Gln Ser Tyr Asp Ser Thr
                85                  90                  95

Leu Arg Val Trp Met Phe Gly Gly Gly Thr Lys Leu Thr Val Leu Gly
            100                 105                 110

```
<210> SEQ ID NO 27
<211> LENGTH: 112
<212> TYPE: PRT
<213> ORGANISM: Homo sapiens

<400> SEQUENCE: 27

Gln Ser Val Leu Thr Gln Pro Pro Ser Val Gly Ala Pro Gly Gln
1               5                   10                  15

Arg Ile Thr Ile Ser Cys Thr Gly Ser Arg Ser Asn Ile Gly Ala Asp
            20                  25                  30

Tyr Asp Val His Trp Tyr Gln Gln Leu Pro Gly Thr Ala Pro Lys Leu
        35                  40                  45

Leu Ile Tyr Ala Asn Asn Arg Pro Ser Gly Val Pro Gly Arg Phe
    50                  55                  60

Ser Ala Ser Lys Ser Gly Thr Ser Ala Ser Leu Ala Ile Ser Gly Leu
65                  70                  75                  80

Gln Ala Glu Asp Glu Ala Asp Tyr Tyr Cys Gln Ser Tyr Asp Ser Ser
                85                  90                  95

Leu Arg Ala Trp Val Phe Gly Gly Gly Thr Lys Leu Ala Val Leu Gly
            100                 105                 110

<210> SEQ ID NO 28
<211> LENGTH: 112
<212> TYPE: PRT
<213> ORGANISM: Homo sapiens

<400> SEQUENCE: 28

Gln Ser Val Leu Thr Gln Pro Pro Ser Val Gly Ala Pro Gly Gln
1               5                   10                  15

Arg Ile Thr Ile Ser Cys Thr Gly Ser Arg Ser Asn Ile Gly Ala Asp
            20                  25                  30

Tyr Asp Val His Trp Tyr Gln Gln Leu Pro Gly Thr Ala Pro Lys Leu
        35                  40                  45

Leu Ile Tyr Ala Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Phe Cys Gln Ser Tyr Asp Ser Ser
                85                  90                  95

Leu Ser Ala Trp Val Phe Gly Gly Gly Thr Lys Val Thr Val Leu Gly
            100                 105                 110

<210> SEQ ID NO 29
<211> LENGTH: 111
<212> TYPE: PRT
<213> ORGANISM: Homo sapiens

<400> SEQUENCE: 29

Gln Ser Val Leu Thr Gln Pro Pro Ser Val Gly Ala Pro Gly Gln
1               5                   10                  15

Arg Val Thr Ile Ser Cys Thr Gly Ser Ser Ser Asn Ile Gly Arg Gly
            20                  25                  30

Tyr Asn Val His Trp Tyr Gln Gln Leu Pro Gly Thr Ala Pro Lys Leu
        35                  40                  45

Leu Ile Tyr Asp Asn Thr Asn Arg Pro Ser Gly Val Pro Ala Arg Phe
    50                  55                  60

Ser Gly Ser Lys Ser Ala Thr Ser Ala Ser Leu Thr Ile Thr Gly Leu
65                  70                  75                  80
```

```
Gln Ala Asp Asp Glu Ala Asp Tyr Tyr Cys Gln Ser Tyr Asp Ser Gly
                85                  90                  95

Leu Arg Trp Val Phe Gly Gly Gly Thr Lys Leu Thr Leu Leu Gly
            100                 105                 110

<210> SEQ ID NO 30
<211> LENGTH: 111
<212> TYPE: PRT
<213> ORGANISM: Homo sapiens

<400> SEQUENCE: 30

Gln Ser Val Leu Thr Gln Pro Pro Ser Val Ser Gly Ala Pro Gly Gln
1               5                   10                  15

Arg Ile Thr Ile Ser Cys Thr Gly Ser Ser Asn Ile Gly Ala Gly
            20                  25                  30

Tyr Asp Val His Trp Tyr Gln Gln Val Pro Gly Lys Ala Pro Lys Val
            35                  40                  45

Val Ile Tyr Gly Asn Asn Asn Arg Pro Ser Gly Val Pro Asp Arg Phe
        50                  55                  60

Ser Gly Ser Lys Ser Gly Ala Ser Ala Ser Leu Ala Ile Thr Gly Leu
65                  70                  75                  80

Gln Thr Glu Asp Glu Ala Asp Tyr Tyr Cys Gln Ser Tyr Asp Lys Ser
                85                  90                  95

Leu Thr Trp Val Phe Gly Gly Gly Thr Lys Val Thr Val Leu Gly
            100                 105                 110

<210> SEQ ID NO 31
<211> LENGTH: 111
<212> TYPE: PRT
<213> ORGANISM: Homo sapiens

<400> SEQUENCE: 31

Gln Ser Val Leu Thr Gln Pro Pro Ser Val Ser Gly Ala Pro Gly Gln
1               5                   10                  15

Arg Ile Thr Ile Ser Cys Thr Gly Thr Ser Asn Ile Gly Ala Gly
            20                  25                  30

Tyr Asp Val His Trp Tyr Gln Gln Leu Pro Gly Ala Ala Pro Arg Val
            35                  40                  45

Leu Ile Tyr Gly Asn Asn Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Gln Ser Tyr Asp Lys Ser
                85                  90                  95

Leu Ser Trp Val Phe Gly Gly Gly Thr Lys Leu Thr Val Leu Arg
            100                 105                 110

<210> SEQ ID NO 32
<211> LENGTH: 112
<212> TYPE: PRT
<213> ORGANISM: Homo sapiens

<400> SEQUENCE: 32

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Phe Asp Val His Trp Tyr Gln Gln Leu Pro Gly Thr Ala Pro Arg Leu
            35                  40                  45
```

Leu Ile Tyr Gly Asn Asn Arg Pro Ser Gly Val Pro Asp Arg Phe
            50                  55                  60

Ser Gly Ser Lys Ser Gly Thr Ser Ala Ser Leu Ala Ile Thr Gly Leu
 65                  70                  75                  80

Gln Ala Glu Asp Glu Thr Asp Tyr Phe Cys Gln Ser Tyr Asp Ser Ser
                 85                  90                  95

Leu Ser Ala Trp Val Phe Gly Gly Gly Thr Lys Val Thr Val Leu Arg
            100                 105                 110

<210> SEQ ID NO 33
<211> LENGTH: 112
<212> TYPE: PRT
<213> ORGANISM: Homo sapiens

<400> SEQUENCE: 33

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Arg Gly
             20                  25                  30

Tyr Asn Val His Trp Tyr Gln Gln Leu Pro Gly Thr Ala Pro Lys Leu
         35                  40                  45

Leu Ile Tyr Asp Asp Thr Asn Arg Pro Ser Gly Val Pro His Arg Phe
     50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Arg Ala Trp Val Phe Gly Gly Gly Thr Lys Leu Ala Val Leu Gly
            100                 105                 110

<210> SEQ ID NO 34
<211> LENGTH: 111
<212> TYPE: PRT
<213> ORGANISM: Homo sapiens

<400> SEQUENCE: 34

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Arg Gly
             20                  25                  30

Tyr Asn Val His Trp Tyr Gln Gln Leu Pro Gly Thr Ala Pro Lys Leu
         35                  40                  45

Leu Ile Tyr Asp Asn Thr Asn Arg Pro Ser Gly Val Pro Ala Arg Phe
     50                  55                  60

Ser Gly Ser Lys Ser Ala Thr Ser Ala Ser Leu Ala Ile Thr Gly Leu
 65                  70                  75                  80

Gln Ala Asp Asp Glu Ala Asp Tyr Tyr Cys Gln Ser Tyr Asp Ser Gly
                 85                  90                  95

Leu Arg Trp Val Phe Gly Gly Gly Thr Lys Leu Thr Leu Leu Arg
            100                 105                 110

<210> SEQ ID NO 35
<211> LENGTH: 111
<212> TYPE: PRT
<213> ORGANISM: Homo sapiens -continued

<400> SEQUENCE: 35

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Arg Gly
            20                  25                  30

Tyr Asn Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Ser Ser Gly Asn Thr Ala Ser Leu Thr Ile Thr Gly Ala
65              70                  75                  80

Gln Ala Glu Asp Glu Ala Asp Tyr Tyr Cys His Ser Arg Asp Asn Asn
                85                  90                  95

Gly His His Ile Phe Gly Gly Gly Thr Lys Leu Thr Val Leu Ser
            100                 105                 110

<210> SEQ ID NO 36
<211> LENGTH: 112
<212> TYPE: PRT
<213> ORGANISM: Homo sapiens

<400> SEQUENCE: 36

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Arg Gly
            20                  25                  30

Tyr Asn Val His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65              70                  75                  80

Gln Ala Glu Asp Glu Gly Asp Tyr Tyr Cys Gln Ser Tyr Asp Ser Ser
                85                  90                  95

Leu Ser Ala Trp Val Phe Gly Gly Gly Thr Lys Leu Thr Val Leu Gly
            100                 105                 110

<210> SEQ ID NO 37
<211> LENGTH: 112
<212> TYPE: PRT
<213> ORGANISM: Homo sapiens
<220> FEATURE:
<221> NAME/KEY: misc_feature
<222> LOCATION: (83)..(83)
<223> OTHER INFORMATION: Xaa can be any naturally occurring amino acid

<400> SEQUENCE: 37

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Arg Gly
            20                  25                  30

Tyr Asn Val His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65              70                  75                  80

```
Gln Ala Xaa Asp Glu Gly Asp Tyr Tyr Cys Gln Ser Tyr Asp Ser Ser
            85                  90                  95

Leu Ser Ala Trp Val Phe Gly Gly Gly Thr Lys Leu Thr Val Leu Gly
            100                 105                 110
```

<210> SEQ ID NO 38
<211> LENGTH: 110
<212> TYPE: PRT
<213> ORGANISM: Homo sapiens

<400> SEQUENCE: 38

```
Leu Pro Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

His Val Val Phe Gly Gly Gly Thr Lys Leu Thr Val Leu Gly
            100                 105                 110
```

<210> SEQ ID NO 39
<211> LENGTH: 112
<212> TYPE: PRT
<213> ORGANISM: Homo sapiens

<400> SEQUENCE: 39

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ala Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
            85                  90                  95

Leu Arg Ala Trp Val Phe Gly Gly Gly Thr Lys Leu Ala Val Leu Gly
            100                 105                 110
```

<210> SEQ ID NO 40
<211> LENGTH: 112
<212> TYPE: PRT
<213> ORGANISM: Homo sapiens

<400> SEQUENCE: 40

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45
```

```
Leu Ile Tyr Ala Asn Asn Arg Pro Ser Gly Val Pro Asp Arg Phe
        50                  55                  60
Ser Gly Ser Lys Ser Gly Thr Ser Ala Ser Leu Ala Ile Thr Gly Leu
 65                  70                  75                  80
Gln Ala Glu Asp Glu Ala Asp Tyr Tyr Cys Gln Ser Tyr Asp Ser Ser
                 85                  90                  95
Leu Arg Ala Trp Val Phe Gly Gly Gly Thr Lys Leu Ala Val Leu Gly
            100                 105                 110

<210> SEQ ID NO 41
<211> LENGTH: 111
<212> TYPE: PRT
<213> ORGANISM: Homo sapiens

<400> SEQUENCE: 41

Gln Pro Val Leu Thr Gln Pro Pro Ser Ala Ser Gly Thr Pro Gly Gln
 1               5                  10                  15
Arg Val Thr Ile Ser Cys Ser Gly Ser Ser Ser Asn Ile Gly Ser Asn
                20                  25                  30
Tyr Val Tyr Trp Tyr Gln Gln Leu Pro Gly Thr Ala Pro Lys Leu Pro
            35                  40                  45
Ile Tyr Arg Asn Asn Gln Arg Pro Ser Gly Val Pro Asp Arg Phe Ser
        50                  55                  60
Gly Ser Lys Ser Gly Thr Ser Ala Ser Leu Ala Ile Ser Gly Leu Arg
 65                  70                  75                  80
Ser Glu Asp Glu Ala Asp Tyr Tyr Cys Ala Ala Trp Asp Ser Leu
                 85                  90                  95
Asn Gly Val Val Phe Gly Gly Gly Thr Lys Leu Thr Val Leu Arg
            100                 105                 110

<210> SEQ ID NO 42
<211> LENGTH: 112
<212> TYPE: PRT
<213> ORGANISM: Homo sapiens

<400> SEQUENCE: 42

Gln Ser Val Leu Thr Gln Pro Pro Ser Val Ser Gly Ala Pro Gly Gln
 1               5                  10                  15
Arg Val Thr Ile Ser Cys Thr Gly Ser Ser Ser Asn Ile Gly Ala Gly
                20                  25                  30
Tyr Asp Val His Trp Tyr Gln His Leu Pro Gly Thr Ala Pro Lys Leu
            35                  40                  45
Leu Ile Tyr Gly Asn Ser Asn Arg Pro Ser Gly Val Pro Asp Arg Phe
        50                  55                  60
Ser Gly Ser Lys Ser Gly Thr Ser Ala Ser Leu Ala Ile Thr Gly Leu
 65                  70                  75                  80
Gln Ala Glu Asp Glu Thr Asp Tyr Phe Cys Gln Ser Tyr Asp Ser Ser
                 85                  90                  95
Leu Ser Ala Trp Val Phe Gly Gly Gly Thr Lys Val Thr Val Leu Gly
            100                 105                 110

<210> SEQ ID NO 43
<211> LENGTH: 109
<212> TYPE: PRT
<213> ORGANISM: Homo sapiens
```

```
<400> SEQUENCE: 43

Ser Ser Glu Leu Thr Gln Asp Pro Ala Val Ser Val Ala Leu Gly Gln
1               5                   10                  15

Thr Val Arg Ile Thr Cys Gln Gly Asn Ser Leu Arg Tyr Tyr Tyr Pro
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Thr Gln Ala Glu
65                  70                  75                  80

Asp Glu Ala Asp Tyr Tyr Cys Ser Ser Arg Asp Asn Thr Asp Asn Arg
                85                  90                  95

Val Val Phe Gly Gly Gly Thr Lys Leu Thr Val Leu Gly
                100                 105

<210> SEQ ID NO 44
<211> LENGTH: 109
<212> TYPE: PRT
<213> ORGANISM: Homo sapiens

<400> SEQUENCE: 44

Gln Pro Gly Leu Thr Gln Pro Pro Ser Val Ser Val Ala Pro Gly Gln
1               5                   10                  15

Thr Ala Arg Ile Thr Cys Gly Gly Asp Asn Ile Gly Arg Lys Ser Val
                20                  25                  30

His Trp Tyr Gln Gln Arg Pro Gly Gln Ala Pro Ile Leu Val Ile Arg
            35                  40                  45

Asp Asp Arg Asp Arg Pro Ser Gly Ile Pro Glu Arg Phe Ser Gly Ser
        50                  55                  60

Ser Ser Val Asn Thr Ala Thr Leu Ile Ile Ser Arg Val Glu Ala Gly
65                  70                  75                  80

Asp Glu Ala Asp Tyr Tyr Cys Gln Val Trp Asp Ser Ser Lys His
                85                  90                  95

Tyr Val Phe Gly Pro Gly Thr Lys Val Thr Ala Leu Gly
                100                 105

<210> SEQ ID NO 45
<211> LENGTH: 458
<212> TYPE: PRT
<213> ORGANISM: Homo sapiens

<400> SEQUENCE: 45

Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
                20                  25                  30

Met Pro Val His Pro Gln Arg Leu Pro Arg Met Gln Glu Asp Ser Pro
            35                  40                  45

Leu Gly Gly Gly Ser Ser Gly Glu Asp Asp Pro Leu Gly Glu Glu Asp
        50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95

Glu Val Lys Pro Lys Ser Glu Glu Glu Gly Ser Leu Lys Leu Glu Asp
                100                 105                 110
```

```
Leu Pro Thr Val Glu Ala Pro Gly Asp Pro Gln Pro Gln Asn Asn
        115                 120                 125

Ala His Arg Asp Lys Glu Gly Asp Gln Ser His Trp Arg Tyr Gly
    130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
                180                 185                 190

Leu Arg Leu Arg Asn Asn Gly His Ser Val Gln Leu Thr Leu Pro Pro
                195                 200                 205

Gly Leu Glu Met Ala Leu Gly Pro Gly Arg Glu Tyr Ala Leu Gln Leu
210                 215                 220

His Leu His Trp Gly Ala Ala Gly Arg Pro Gly Ser Glu His Thr Val
225                 230                 235                 240

Glu Gly His Arg Phe Pro Ala Glu Ile His Val Val His Leu Ser Thr
                245                 250                 255

Ala Phe Ala Arg Val Asp Glu Ala Leu Gly Arg Pro Gly Gly Leu Ala
                260                 265                 270

Val Leu Ala Ala Phe Leu Glu Glu Gly Pro Glu Glu Asn Ser Ala Tyr
275                 280                 285

Glu Gln Leu Leu Ser Arg Leu Glu Glu Ile Ala Glu Glu Gly Ser Glu
                290                 295                 300

Thr Gln Val Pro Gly Leu Asp Ile Ser Ala Leu Leu Pro Ser Asp Phe
305                 310                 315                 320

Ser Arg Tyr Phe Gln Tyr Glu Gly Ser Leu Thr Thr Pro Pro Cys Ala
                325                 330                 335

Gln Gly Val Ile Trp Thr Val Phe Asn Gln Thr Val Met Leu Ser Ala
                340                 345                 350

Lys Gln Leu His Thr Leu Ser Asp Thr Leu Trp Gly Pro Gly Asp Ser
                355                 360                 365

Arg Leu Gln Leu Asn Phe Arg Ala Thr Gln Pro Leu Asn Gly Arg Val
                370                 375                 380

Ile Glu Ala Ser Phe Pro Ala Gly Val Asp Ser Ser Pro Arg Ala Ala
385                 390                 395                 400

Glu Pro Val Gln Leu Asn Ser Cys Leu Ala Ala Gly Asp Ile Leu Ala
                405                 410                 415

Leu Val Phe Gly Leu Leu Phe Ala Val Thr Ser Val Ala Phe Leu Val
                420                 425                 430

Gln Met Arg Arg Gln His Arg Arg Gly Thr Lys Gly Gly Val Ser Tyr
                435                 440                 445

Arg Pro Ala Glu Val Ala Glu Thr Gly Ala
                450                 455

<210> SEQ ID NO 46
<211> LENGTH: 437
<212> TYPE: PRT
<213> ORGANISM: Mus musculus

<400> SEQUENCE: 46

Met Ala Ser Leu Gly Pro Ser Pro Trp Ala Pro Leu Ser Thr Pro Ala
1               5                   10                  15

Pro Thr Ala Gln Leu Leu Leu Phe Leu Leu Leu Gln Val Ser Ala Gln
                20                  25                  30
```

-continued

Pro Gln Gly Leu Ser Gly Met Gln Gly Glu Pro Ser Leu Gly Asp Ser
            35                  40                  45

Ser Ser Gly Glu Asp Glu Leu Gly Val Asp Val Leu Pro Ser Glu Glu
 50                  55                  60

Asp Ala Pro Glu Ala Asp Pro Pro Asp Gly Glu Asp Pro Pro Glu
 65                  70                  75                  80

Val Asn Ser Glu Asp Arg Met Glu Glu Ser Leu Gly Leu Glu Asp Leu
                85                  90                  95

Ser Thr Pro Glu Ala Pro Glu His Ser Gln Gly Ser His Gly Asp Glu
            100                 105                 110

Lys Gly Gly His Ser His Trp Ser Tyr Gly Gly Thr Leu Leu Trp
            115                 120                 125

Pro Gln Val Ser Pro Ala Cys Ala Gly Arg Phe Gln Ser Pro Val Asp
            130                 135                 140

Ile Arg Leu Glu Arg Thr Ala Phe Cys Arg Thr Leu Gln Pro Leu Glu
145                 150                 155                 160

Leu Leu Gly Tyr Glu Leu Gln Pro Leu Pro Glu Leu Ser Leu Ser Asn
                165                 170                 175

Asn Gly His Thr Val Gln Leu Thr Leu Pro Pro Gly Leu Lys Met Ala
            180                 185                 190

Leu Gly Pro Gly Gln Glu Tyr Arg Ala Leu Gln Leu His Leu His Trp
            195                 200                 205

Gly Thr Ser Asp His Pro Gly Ser Glu His Thr Val Asn Gly His Arg
            210                 215                 220

Phe Pro Ala Glu Ile His Val Val His Leu Ser Thr Ala Phe Ser Glu
225                 230                 235                 240

Leu His Glu Ala Leu Gly Arg Pro Gly Gly Leu Ala Val Leu Ala Ala
                245                 250                 255

Phe Leu Gln Glu Ser Pro Glu Glu Asn Ser Ala Tyr Glu Gln Leu Leu
            260                 265                 270

Ser His Leu Glu Glu Ile Ser Glu Glu Gly Ser Lys Ile Glu Ile Pro
            275                 280                 285

Gly Leu Asp Val Ser Ala Leu Leu Pro Ser Asp Phe Ser Arg Tyr Tyr
            290                 295                 300

Arg Tyr Glu Gly Ser Leu Thr Thr Pro Pro Cys Ser Gln Gly Val Ile
305                 310                 315                 320

Trp Thr Val Phe Asn Glu Thr Val Lys Leu Ser Ala Lys Gln Leu His
                325                 330                 335

Thr Leu Ser Val Ser Leu Trp Gly Pro Arg Asp Ser Arg Leu Gln Leu
            340                 345                 350

Asn Phe Arg Ala Thr Gln Pro Leu Asn Gly Arg Thr Ile Glu Ala Ser
            355                 360                 365

Phe Pro Ala Ala Glu Asp Ser Ser Pro Glu Pro Val His Val Asn Ser
            370                 375                 380

Cys Phe Thr Ala Gly Asp Ile Leu Ala Leu Val Phe Gly Leu Leu Phe
385                 390                 395                 400

Ala Val Thr Ser Ile Ala Phe Leu Leu Gln Leu Arg Arg Gln His Arg
                405                 410                 415

His Arg Ser Gly Thr Lys Asp Arg Val Ser Tyr Ser Pro Ala Glu Met
            420                 425                 430

Thr Glu Thr Gly Ala
            435

-continued

<210> SEQ ID NO 47
<211> LENGTH: 38
<212> TYPE: DNA
<213> ORGANISM: Artificial sequence
<220> FEATURE:
<223> OTHER INFORMATION: Chemically synthesized primer

<400> SEQUENCE: 47
atcgacgcgt gcctgagcga ggtgcagctg gtgcagtc                                  38

<210> SEQ ID NO 48
<211> LENGTH: 32
<212> TYPE: DNA
<213> ORGANISM: Artificial sequence
<220> FEATURE:
<223> OTHER INFORMATION: Chemically synthesized primer

<400> SEQUENCE: 48
caatggtcac cgtctcttca gctagcacca gg                                        32

<210> SEQ ID NO 49
<211> LENGTH: 35
<212> TYPE: DNA
<213> ORGANISM: Artificial sequence
<220> FEATURE:
<223> OTHER INFORMATION: Chemically synthesized primer

<400> SEQUENCE: 49
atcccaagct taagccagtc tgtgctgact cagcc                                     35

<210> SEQ ID NO 50
<211> LENGTH: 31
<212> TYPE: DNA
<213> ORGANISM: Artificial sequence
<220> FEATURE:
<223> OTHER INFORMATION: Chemically synthesized primer

<400> SEQUENCE: 50
ggagggacca aattgaccgt cctaggtcag c                                         31

<210> SEQ ID NO 51
<211> LENGTH: 41
<212> TYPE: DNA
<213> ORGANISM: Artificial sequence
<220> FEATURE:
<223> OTHER INFORMATION: Chemically synthesized primer

<400> SEQUENCE: 51
tagggcacgc gtgtgctgag cgaggtgcag ctggtgcagt c                              41

<210> SEQ ID NO 52
<211> LENGTH: 32
<212> TYPE: DNA
<213> ORGANISM: Artificial sequence
<220> FEATURE:
<223> OTHER INFORMATION: Chemically synthesized primer

<400> SEQUENCE: 52
tctagtgcta gctgaagaga cggtgaccat tg                                        32

<210> SEQ ID NO 53
<211> LENGTH: 35
<212> TYPE: DNA
<213> ORGANISM: Artificial sequence
<220> FEATURE:
<223> OTHER INFORMATION: Chemically synthesized primer -continued

<400> SEQUENCE: 53
ctagcaagct tatcccagtc tgtgctgact cagcc                                     35

<210> SEQ ID NO 54
<211> LENGTH: 26
<212> TYPE: DNA
<213> ORGANISM: Artificial sequence
<220> FEATURE:
<223> OTHER INFORMATION: Chemically synthesized primer

<400> SEQUENCE: 54
atagcaccta ggacggtcag cttggt                                               26

<210> SEQ ID NO 55
<211> LENGTH: 5
<212> TYPE: PRT
<213> ORGANISM: Artificial sequence
<220> FEATURE:
<223> OTHER INFORMATION: Portion of CDR1 heavy chain sequence

<400> SEQUENCE: 55

Ser Tyr Ala Met Ser
1               5

<210> SEQ ID NO 56
<211> LENGTH: 5
<212> TYPE: PRT
<213> ORGANISM: Artificial sequence
<220> FEATURE:
<223> OTHER INFORMATION: Portion of CDR1 heavy chain sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 56

Xaa Tyr Ala Met Xaa
1               5

<210> SEQ ID NO 57
<211> LENGTH: 5
<212> TYPE: PRT
<213> ORGANISM: Artificial sequence
<220> FEATURE:
<223> OTHER INFORMATION: Portion of CDR1 heavy chain sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 57

Ser Tyr Xaa Met Xaa
1               5

<210> SEQ ID NO 58
<211> LENGTH: 17
<212> TYPE: PRT
<213> ORGANISM: Artificial sequence
<220> FEATURE:
<223> OTHER INFORMATION: Portion of CDR2 heavy chain sequence

```
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 58

Ala Ile Ser Xaa Xaa Gly Gly Xaa Thr Xaa Xaa Ala Asp Ser Val Lys
1               5                   10                  15

Gly

<210> SEQ ID NO 59
<211> LENGTH: 17
<212> TYPE: PRT
<213> ORGANISM: Artificial sequence
<220> FEATURE:
<223> OTHER INFORMATION: Portion of CDR2 heavy chain sequence

<400> SEQUENCE: 59

Ala Ile Ser Gly Ser Gly Gly Ser Thr Thr Thr Ala Asp Ser Val Lys
1               5                   10                  15

Gly

<210> SEQ ID NO 60
<211> LENGTH: 13
<212> TYPE: PRT
<213> ORGANISM: Artificial sequence
<220> FEATURE:
<223> OTHER INFORMATION: Portion of CDR3 heavy chain sequence
<220> FEATURE:
<221> NAME/KEY: misc_feature
<222> LOCATION: (9)..(9)
<223> OTHER INFORMATION: Xaa can be any naturally occurring amino acid

<400> SEQUENCE: 60

Asn Gly Asn Tyr Arg Gly Ser Leu Xaa Ala Phe Asp Ile
1               5                   10

<210> SEQ ID NO 61
<211> LENGTH: 14
<212> TYPE: PRT
<213> ORGANISM: Artificial sequence
<220> FEATURE:
<223> OTHER INFORMATION: Portion of CDR1 light chain sequence

<400> SEQUENCE: 61

Thr Gly Ser Ser Ser Asn Ile Gly Ala Gly Tyr Asp Val His
1               5                   10

<210> SEQ ID NO 62
<211> LENGTH: 7
<212> TYPE: PRT
<213> ORGANISM: Artificial sequence
<220> FEATURE:
<223> OTHER INFORMATION: Portion of CDR2 light chain sequence

<400> SEQUENCE: 62

Gly Asn Asn Asn Arg Pro Ser
1               5
```

```
<210> SEQ ID NO 63
<211> LENGTH: 12
<212> TYPE: PRT
<213> ORGANISM: Artificial sequence
<220> FEATURE:
<223> OTHER INFORMATION: Portion of CDR3 light chain sequence

<400> SEQUENCE: 63

Gln Ser Tyr Asp Ser Ser Leu Ser Ala Trp Val Val
1               5                   10

<210> SEQ ID NO 64
<211> LENGTH: 6
<212> TYPE: PRT
<213> ORGANISM: Artificial sequence
<220> FEATURE:
<223> OTHER INFORMATION: Consensus sequence

<400> SEQUENCE: 64

Glu Glu Asp Leu Pro Glu
1               5

<210> SEQ ID NO 65
<211> LENGTH: 10
<212> TYPE: PRT
<213> ORGANISM: Artificial Sequence
<220> FEATURE:
<223> OTHER INFORMATION: Portion of the CDR3 heavy chain sequence

<400> SEQUENCE: 65

Asn Gly Asn Tyr Arg Gly Ala Phe Asp Ile
1               5                   10
```